(12) United States Patent
Nanduri et al.

(10) Patent No.: US 6,576,662 B2
(45) Date of Patent: Jun. 10, 2003

(54) COMPOUNDS HAVING ANTICANCER ACTIVITY : PROCESS FOR THEIR PREPARATION AND PHARMACEUTICAL COMPOSITIONS CONTAINING THEM

(75) Inventors: Srinivas Nanduri, Andhra Pradesh (IN); Sriram Rajagopal, Andhra Pradesh (IN); Venkateswarlu Akella, Andhra Pradesh (IN)

(73) Assignee: Dr. Reddy's Laboratories Limited, Andhra Pradesh (IN)

( * ) Notice: Subject to any disclaimer, the term of this patent is extended or adjusted under 35 U.S.C. 154(b) by 67 days.

(21) Appl. No.: 09/849,584

(22) Filed: May 4, 2001

(65) Prior Publication Data

US 2002/0016324 A1 Feb. 7, 2002

(30) Foreign Application Priority Data

May 5, 2000 (IN) ..................................... 353/MAS/2000

(51) Int. Cl.⁷ ........................ A61K 31/34; C07D 305/12
(52) U.S. Cl. ...................................... 514/473; 549/323
(58) Field of Search ........................... 514/473; 549/323

(56) References Cited

U.S. PATENT DOCUMENTS 6,136,316 A * 10/2000 Mehrotra et al. ........ 424/195.1
6,410,590 B1 * 6/2002 Nanduri et al. ............. 514/462

FOREIGN PATENT DOCUMENTS

| JP | 6388124 | 4/1988 |
| WO | 9101742 | 2/1991 |
| WO | 9617605 | 6/1996 |

OTHER PUBLICATIONS

Basak, A. et al. "Inhibition of Proprotein Convertases—1, –7 and Furin by Diterpines of *Andrographis paniculata* and Their Succinoyl Esters" Biochemistry Journal, vol. 338, p. 107–113, (1999).

Chang, R.S. et al. "Dehydroandrographolide Succinic Acid Monoester as an Inhibitor Against the Human Immunodeficiency Virus" Proc. Soc. Exp. Biol. Med., vol. 197, p. 59–66, (1991).

Matsuda, T. et al. "Cell Differentiation–Inducing Diterpenes from *Andrographis paniculata* Nees" Chem. Pharm. Bull. vol. 42 (6), p. 1216–1225, (1994).

Siripong, P. et al. "Cytotoxic Diterpenoid Constituents From *Andrographis paniculara* Nees Leaves" J. Sci. Soc. Thailand, vol. 18, p. 187–194, (1992).

Choudhury, B.R. et al. "In Vivo and In Vitro Effects of Kalmegh (*Andrographis paniculata*) Extract and Andrographolide on Hepatic Microsomal . . . Enzymes" Planta Medica, vol. 53 (2), p. 135–140, (1987).

Puri, A. et al., "Immunostimulant Agents from *Andrographis paniculata*" Journal of Natural Product, vol. 56 (7), p. 995–999, (1993).

Rahman, N.N.N.A. et al. " Antimalarial Activity of Extracts of Malaysian Medicinal Plants" Journal of Ethanopharmacology, vol. 64, p. 249–254, (1999).

Misra, P. et al. Antimalarial Activity of *Andrographis paniculata* (Kalmegh) against *Plasmodium berghei* NK 65 i *Mastomys natalensis*, Int. J. Pharmacog., vol. 30 (4), p. 263–274, (1992).

Long, D.W. "Antiinfammatory Agents from Traditional Chinese Drugs" Drugs of the Future, vol. 15 (8), p. 809–816, (1990).

"The Useful Plants of India" Ed. S.B. Ambasta, p. 39, (1992).

"Glossary of Indian Medicinal Plants" Ed. R.N. Chopra et al. p. 18, (1956).

Gupta, S. et al. "Antidiarrhoeal Activity of Diterpenes of *Andrographis paniculata* (Kal–Megh) Against *Escherichia coli* Enterotoxin in in vivo Models" Int. J. Crude Drug Res., vol. 28 (4), p. 273–283, (1990).

Medicinal & Aromatic Plants Abstracts, Wang, D.W. et al. Chinese Medical Journal, vol. 107(6), p. 464–470, (1994).

Medicinal & Aromatic Plants Abstracts, Zhao, H. Y. et al. Chinese Medical Journal, vol. 104 (9), p. 770–775, (1991).

American Chemical Society, Meijer, L. Prog. Cell Cycle Research, vol. 1, p. 351–363, (1995).

Pharmaceutical Chemistry, K. Gorter, Rec. Trav. Chim. vol. 30, p. 151–160, (1911).

Cava, M.P. et al. "The Structure of Andrographolide" Tetrahedron, p. 397, (1962).

* cited by examiner

Primary Examiner—Deborah C. Lambkin
(74) Attorney, Agent, or Firm—Ladas & Parry

(57) ABSTRACT

The present invention relates to novel anticancer agents, their stereoisomers, their polymorphs, their pharmaceutically acceptable salts, and their pharmaceutically acceptable solvates. The present invention more particularly relates to novel derivatives of andrographolide, their stereoisomers, their polymorphs, their pharmaceutically acceptable salts, and their pharmaceutically acceptable solvates. The novel derivatives of andrographolide have the general formula (I).

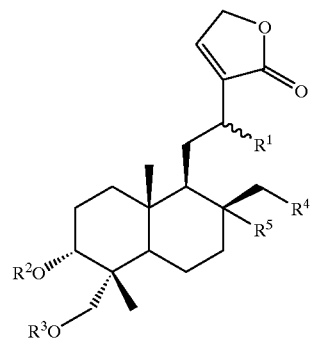

59 Claims, No Drawings

COMPOUNDS HAVING ANTICANCER ACTIVITY : PROCESS FOR THEIR PREPARATION AND PHARMACEUTICAL COMPOSITIONS CONTAINING THEM

FIELD OF THE INVENTION

The present invention relates to novel anticancer agents, their stereoisomers, their polymorphs, their pharmaceutically acceptable salts, and their pharmaceutically acceptable solvates. The present invention more particularly relates to novel derivatives of andrographolide, their stereoisomers, their polymorphs, their pharmaceutically acceptable salts, and their pharmaceutically acceptable solvates. The novel derivatives of andrographolide have the general formula (I),

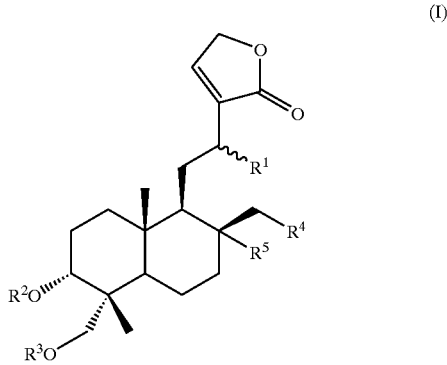

(I)

where $R^1$ represents hydrogen, halogen, thio, or substituted or unsubstituted alkyl, alkylthio, heteroarylthio, acylthio, aralkylthio, arylthio, alkylseleno, acylseleno, aralkylseleno, arylseleno, $NR^aR^b$ where $R^a$, and $R^b$ may be same or different and independently represent hydrogen, substituted or unsubstituted alkyl, aryl, acyl, aralkyl, heteroaryl, haloalkyl, or haloacyl or $R^a$ and $R^b$ together with the nitrogen atom to which they are attached may form substituted or unsubstituted 5 or 6 membered cyclic ring system containing carbon atoms, at least one nitrogen atom and optionally one or more hetero atoms selected from oxygen, sulfur or nitrogen, the cyclic ring system may contain one or two double bonds or it may be aromatic or $R^1$ may represent $OR^6$ where $R^6$ represents hydrogen or substituted or unsubstituted groups selected from alkyl, aryl, aralkyl, alkenoyl, alkanoyl, aroyl, heteroaroyl, aralkenoyl, aralkanoyl, sulfonyl groups or a group —(CO)—NH—$R^7$ where $R^7$ represents substituted or unsubstituted groups selected from alkyl, aryl, or aralkyl; $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, aralkenoyl, aralkanoyl, sulfonyl group or a group —(CO)—W—$R^8$ where W represents O, S or $NR^9$, wherein $R^9$ represents hydrogen or $(C_1-C_6)$alkyl group, $R^8$ represents substituted or unsubstituted groups selected from alkyl, aryl, aralkyl or aroyl or $OR^2$ and $OR^3$ together form a substituted or unsubstituted 6 or 7 membered cyclic structure containing carbon and oxygen atoms; and $R^4$ and $R^5$ together represents =$CH_2$ or an epoxide group.

The andrographolide derivatives represented by general formula (I) defined above of the present invention and general formulas (IX), (X) and (XI) as defined below are useful for treating cancer and other proliferative diseases including but not limited to herpes simplex virus types I and II (HSV I and HSV II) and human immunodeficiency (HIV). The compounds of the present invention are also useful in the treatment of psoriasis, restonosis, atherosclerosis and other cardiovascular disorders. The compounds of the present invention are also useful as antiviral, antimalarial, antibacterial, hepatoprotective, immunomodulating agents and for treatment of metabolic disorders. The anticancer activity exhibited may be through cytotoxic activity, antiproliferation, cell cycle kinase inhibition or may be through cell differentiation.

The compounds of this invention are also useful for the treatment and/or prophylaxis of insulin resistance (type II diabetes), leptin resistance, impaired glucose tolerance, dyslipidemia, body weight reduction, disorders related to syndrome X such as hypertension, obesity, insulin resistance, coronary heart disease and other cardiovascular disorders.

The present invention also relates to pharmaceutical compositions containing compounds of general formula (I), formula (IX), formula (X), or formula (XI), or their stereoisomers, their polymorphs, their salts, or their solvates or mixtures thereof.

The present invention also relates to a process for the preparation of the compounds of general formula (I), formula (IX), formula (X), and formula (XI), and their stereoisomers, their polymorphs, their pharmaceutically acceptable salts, and their pharmaceutically acceptable solvates.

BACKGROUND OF THE INVENTION

The plant andrographis paniculata is extensively used in medicine as a bitter tonic, febrifuge and in bowel complaints (Glossary of Indian Medicinal Plants., Ed. R. N. Chopra, S. L. Nayar, I. C. Chopra, p18, 1996; The useful plants of India, Ed. By S. B. Ambasta, p39, 1992). The plant is useful in the treatment of bacterial infections (Int. J. Crude Drug Res. 1990, 28(4), p273–283; Drugs of the Future. 1990, 15(8) p809–816). It is reported to possess antimalarial (Int. J. Pharmacognosy, 1992, 30(4), p263–274; J. Ethnopharmocol., 1999, 64(3), p249–254) and immunostimulant activity (J. Nat. Prod., 1993, 56(7), p995–999). The plant has also been shown to be antithrombotic (Chinese Medical Journal 1991, 104(9), p770–775) and inhibit stenosis and restenosis after angioplasty in the rat (Chinese Medical Journal, 1994, 107(6), p464–470). It is also known that the plant extract and its constituents exhibit promising hepatoprotective activity (Planta Medica, 1987, 53(2), p135–140). Significant attention has been paid by several research groups on A. paniculata in recent years due to its cytotoxic, antitumorogenic, cell differentiation inducing activities and anti-HIV activities.

Andrographolide having the formula (II),

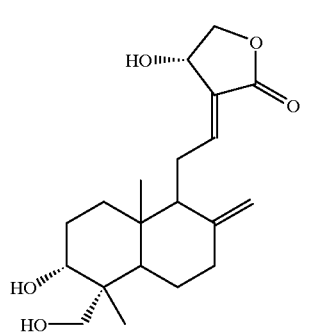

II the major constituent of the plant A. paniculata was first isolated by Gorter (Rec. trav. chim., 1911, 30, p151–160).

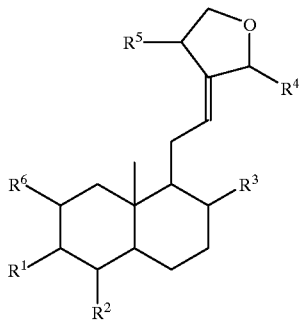

(III)

The extracts of the dried plant, which contains compounds of formula (III), have been assayed for the ability to decrease expression and phosphorylation of p34$^{cdc2}$ kinase, cyclin B and c-Mos for treating or preventing pathogenecity of diseases such as AIDS, Alzheimer's disease and hepatitis (WO 96/17605).

Cell cycle kinases are naturally occurring enzymes involved in regulation of the cell cycle (Progress in *Cell Cycle Research*, 1995, 1, p351–363). Typical enzymes include the cyclin-dependent kinases (cdk) cdk1, cdk2, cdk4, cdk5, cdk6 and wee-1 kinase. Increased activity or temporarily abnormal activation of these kinases has been shown to result in development of tumors and other proliferative disorders such as restenosis. Compounds that inhibit cdks, either by blocking the interaction between a cyclin and its kinase partner or by binding to and inactivating the kinase, cause inhibition of cell proliferation and are thus useful for treating tumors or other abnormally proliferating cells.

The extract of *A. paniculata* was found to show significant cytotoxic activity against KB and P388 cells. Interestingly, Andrographolide of the formula II, has been shown for the first time to have potent cytotoxic activity against KB as well as P388 lymphocytic leukemia, where as 14-deoxy-11,12-didehydroandrographolide and neoandrographolide having the formulae IV & V

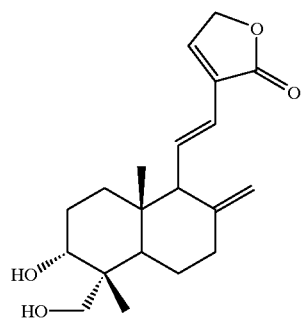

(IV)

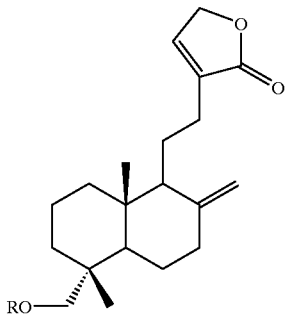

(V)

where R represents β-D-glucose moiety, have shown no cytotoxic activity in tumor cell lines (*J. Sci. Soc. Thailand*, 1992, 18, p187–194).

The methanolic extract of the aerial parts of *A. paniculata* Nees showed potent cell differentiation inducing activity on mouse myeloid leukemia (M1) cells (*Chem. Pharm. Bull.* 1994, 42(6) 1216–1225).

Japanese patent application JP 63-88124, discloses a mixture of at least two compounds of formula VIa, VIb,

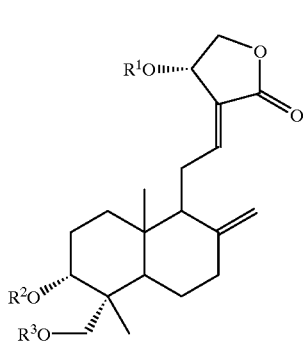

VIa

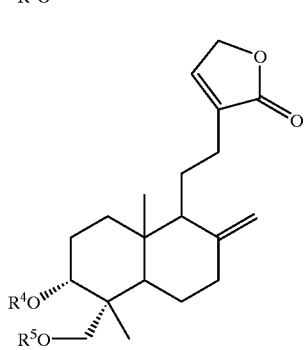

VIb where $R^1$, $R^2$, $R^3$, $R^4$ and $R^5$ represent hydrogen or lower alkanoyl group and discloses their activity as antitumorogenic agents.

DASM (dehydroandrographolide succinic acid monoester) prepared from andrographolide of the formula II is found to be inhibiting HIV virus and nontoxic to the H9 cell at the concentrations of 50–200 μg/ml and was inhibitory to HIV-1(IIIB) at the minimal concentration of 1.6–3.1 μg/ml (*Proc. Soc. Exp. Biol. Med.*, 1991, 197, p59–66).

The plant *Andrographis paniculata* is also reported to inhibit proprotein convertases-1, -7 and furin possibly bysuppressing the proteolytic cleavage of envelops glycoprotein gp 160 of HIV, which is known to be PC-mediated, particularly by furin and PC (*Biochem. J.,* 1999, 338, 107–113)

In International patent application WO 91/01742, compositions containing one or more ingredients obtained from the plants *Valeariana officinalis* and/or *A. paniculata* were disclosed to have antiviral, antineoplastic, antibacterial and immunomodulatory activity.

Although several novel andrographolide derivatives have been prepared, screened and reported in the above said prior-art literature for their anticancer activity, they are not showing interesting activity.

OBJECTIVE OF THE INVENTION

With an objective of preparing novel andrographolide derivatives useful for treating cancer, diseases and infections caused by HSV and HIV, psoriasis, restenosis, atherosclerosis, cardiovascular disorders, also useful as antiviral, antimalarial, antibacterial, hepatoprotective, immunomodulating agents and for treatment of metabolic disorders, which are potent at lower doses and having better efficacy with lower toxicity, we focussed our research efforts in preparing the novel andrographolide derivatives of the formula (I) as defined above.

The main objective of the present invention is, therefore, to provide novel andrographolide derivatives of the formula (J) as defined above, and formulas (IX), (X) and (XI) as defined below, their stereoisomers, their polymorphs, their pharmaceutically acceptable salts, their pharmaceutically acceptable solvates and compositions containing them or their mixtures.

Another objective of the present invention is to provide pharmaceutical compositions containing compounds of the general formula (I), formula (IX), formula (X), formula (XI), their stereoisomers, their polymorphs, their pharmaceutically acceptable salts, or their pharmaceutically acceptable solvates or their mixtures in combination with suitable carriers, solvents, diluents and other media normally employed in preparing such compositions.

Still another objective of the present invention is to provide pharmaceutical compositions containing compounds of formula (I), formula (IX), formula (X), formula (XI), their stereoisomers, their polymorphs, their pharmaceutically acceptable salts, or their pharmaceutically acceptable solvates, their mixtures in combination with one or more pharmaceutically acceptable active compounds with suitable carriers, solvents, diluents and other media normally employed in preparing such compositions.

Still another objective of the present invention is to provide a process for the preparation of novel andrographolide derivatives of the formula (I), formula (IX), formula (X), and formula (XI), their stereoisomers, their polymorphs, their pharmaceutically acceptable salts, and their pharmaceutically acceptable solvates and pharmaceutical compositions containing them or their mixtures having enhanced activity, no toxic effect or reduced toxic effect.

DETAILED DESCRIPTION OF THE INVENTION

Accordingly, the novel derivatives of andrographolide of the present invention have the general formula (I)

(I)

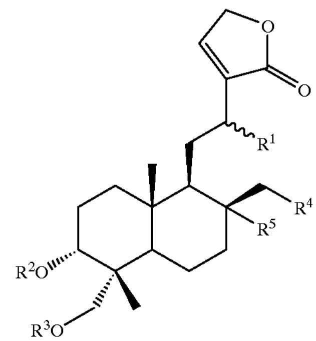

where $R^1$ represents hydrogen, halogen, thio, or substituted or unsubstituted alkyl alkylthio, heteroarylthio, acylthio, aralkylthio, arylthio, alkylseleno, acylseleno, aralkylseleno, arylseleno, $NR^aR^b$ where $R^a$, and $R^b$ may be same or different and independently represent hydrogen, substituted or unsubstituted alkyl, aryl, acyl, aralkyl, heteroaryl, haloalkyl, or haloacyl or $R^a$ and $R^b$ together with the nitrogen atom to which they are attached may form substituted or unsubstituted 5 or 6 membered cyclic ring system containing carbon atoms, at least one nitrogen atom and optionally one or more hetero atoms selected from oxygen, sulfur or nitrogen, the cyclic ring system may contain one or two double bonds or it may be aromatic or $R^1$ may represent $OR^6$ where $R^6$ represents hydrogen or substituted or unsubstituted groups selected from alkyl, aryl, aralkyl, alkenoyl, alkanoyl, aroyl, heteroaroyl, aralkenoyl, aralkanoyl, sulfonyl groups or a group —(CO)—NH—$R^7$ where $R^7$ represents substituted or unsubstituted groups selected from alkyl, aryl, or aralkyl; $R^2$ and $R^3$ may be same or different and independently represent hydrogen or substituted or unsubstituted groups selected from alkyl, aryl, or heteroaryl, aralkyl, heteroaralkyl, alkanoyl, alkenoyl, aroyl, heteroaroyl, aralkenoyl, aralkanoyl, sulfonyl group or a group —(CO)—W—$R^8$ where W represents O, S or $NR^9$, wherein $R^9$ represents hydrogen or $(C_1–C_6)$alkyl group, $R^8$ represents substituted or unsubstituted groups selected from alkyl, aryl, aralkyl or aroyl or $OR^2$ and $OR^3$ together form a substituted or unsubstituted 6 or 7 membered cyclic structure containing carbon and oxygen atoms; and $R^4$ and $R^5$ together represents $=CH_2$ or an epoxide group; their stereoisomers, their polymorphs, their pharmaceutically acceptable salts and their pharmaceutically acceptable solvates.

Suitable groups represented by $R^1$ may be selected from hydrogen, thio, halogen such as fluorine, chlorine or bromine and the like; linear or branched $(C_1–C_8)$ alkyl group such as methyl, ethyl, n-propyl, iso-propyl and the like; the alkyl group may be substituted; $(C_1–C_8)$alkylthio group such as methylthio, ethylthio, propylthio and the like, the alkylthio group may be substituted; heteroarylthio group such as pyridylthio, furylthio, thiophenylthio, benzothiazolethio, purinethio, benzimidazolethio, pyrimidinethio and the like, the heteroarylthio group may be substituted; acylthio group such as acetylthio, propanoylthio, butanoylthio and the like, the acylthio group may be substituted; aralkylthio group such as benzylthio, phenylethylthio, phenylpropylthio and the like, the aralkylthio group may be substituted; arylthio group such as phenylthio, napthylthio and the like, the arylthio group may be substituted; $(C_1-C_8)$alkylseleno such as methylseleno, ethylseleno, propylseleno, iso-propylseleno and the like, the alkylseleno group may be substituted; acylseleno such as acylamino group such as acetylseleno, propionylseleno and the like, the acylseleno group may be substituted; aralkylseleno such as benzylseleno, phenylethylseleno, phenylpropylseleno and the like, the aralkylseleno group may be substituted; arylseleno such as phenylseleno, napthylseleno and the like, the aralkylseleno group may be substituted; $NR^aR^b$ or $OR^6$.

Suitable groups represented by $R^a$ and $R^b$ include hydrogen, substituted or unsubstituted, linear or branched $(C_1-C_8)$ alkyl group such as methyl, ethyl, n-propyl, iso-propyl and the like; aryl group such as phenyl, naphthyl and the like, the aryl group may be substituted; acyl group such as acetyl, propionyl and the like, the acyl group may be substituted; aralkyl such as benzyl, phenethyl and the like, the aralkyl group may be substituted; heteroaryl group such as pyridyl, furyl, thiophenyl, benzothiazoyl, purinyl, benzimidazoyl, pyrimidinyl, tetrazolyl and the like, the heteroaryl group may be substituted; halo$(C_1-C_8)$alkyl such as chloromethyl, bromoethyl and the like; haloacyl such as chloroacetyl and the like.

The cyclic ring system formed by $R^a$ and $R^b$ together with the nitrogen atoms may be selected from uracil, substituted uracil, imidazole, triazole, tetrazole, morpholine, piperazine, pyrazine, pyrimidinone, cytosine, pyrrolidine and the like.

Suitable substituents on the cyclic ring system formed by $R^a$ and $R^b$ together with nitrogen atoms may be selected from hydrogen, hydroxy, halogen atoms such as fluorine, chlorine, bromine and the like; linear or branched $(C_1-C_8)$ alkyl group such as methyl, ethyl, n-propyl, iso-propyl and the like; $(C_2-C_6)$alkenyl group such as ethenyl, propenyl, butenyl and the like; $(C_2-C_6)$alkylenyl such as acetylenyl, propylenyl, butylenyl and the like; amino, nitro, oxo, thio, and imino groups.

Suitable groups represented by $R^2$ and $R^3$ include hydrogen, substituted or unsubstituted, linear or branched $(C_1-C_8)$ alkyl group such as methyl, ethyl, n-propyl, iso-propyl and the like; aryl group such as phenyl, naphthyl and the like, the aryl group may be substituted; heteroaryl group such as pyridyl, furyl, thiophenyl and the like, the heteroaryl group may be substituted; aralkyl such as benzyl, phenethyl and the like, the aralkyl group may be substituted; heteroaralkyl group such as pyridylmethyl, pyridylethyl, furanmethyl, furanethyl and the like, the heteroaralkyl group may be substituted; $(C_2-C_8)$ alkanoyl group such as ethanoyl, propanoyl, butanoyl and the like, the $(C_2-C_8)$ alkanoyl group may be substituted; $(C_3-C_8)$ alkenoyl group such as propenoyl, butenoyl, pentenoyl and the like, $(C_3-C_8)$ alkenoyl group may be substituted; aroyl group such as benzoyl and the like, the aroyl group may be substituted; heteroaroyl group such as pyridyl carbonyl, furyl carbonyl and the like; the heteroaroyl group may be substituted; aralkenoyl group such as phenylpropenoyl, phenylbutenoyl, phenylpentenoyl and the like, the aralkenoyl group may be substituted; aralkanoyl group such as phenylpropanoyl, phenylbutanoyl, phenylpentanoyl and the like, the aralkanoyl group may be substituted; sulfonyl group such as methanesulfonyl, benzenesulfonyl, p-toluenesulfonyl and the like, the sulfonyl group may be substituted.

Suitable cyclic structures formed by $OR^2$ and $OR^3$ may be selected from $-O-(CR^{10}R^{11})_m-O-$ where $R^{10}$ and $R^{11}$ may be same or different and independently represent hydrogen, or unsubstituted or substituted groups selected from $(C_1-C_6)$ alkyl such as methyl, ethyl, n-propyl and the like; aryl group such as phenyl, naphthyl and the like, the aryl group may be substituted; heteroaryl group such as pyridyl, furyl, thiophenyl, pyrrolyl and the like; the heteroaryl group may be substituted or $R^{10}$ and $R^{11}$ together represent C=O; and m represents an integer 1 or 2. The substituents on $R^9$ and $R^{10}$ include hydroxy, halogen such as fluorine, chlorine, bromine and the like; nitro, cyano or amino groups.

Suitable groups represented by $R^6$ may be selected from hydrogen, linear or branched $(C_1-C_8)$ alkyl group such as methyl, ethyl, n-propyl, iso-propyl and the like, the $(C_1-C_8)$ alkyl group may be substituted; aryl group such as phenyl, naphthyl and the like, the aryl group may be substituted; aralkyl such as benzyl, phenethyl and the like, the aralkyl group may be substituted; $(C_2-C_8)$alkanoyl group such as ethanoyl, propanoyl, butanoyl and the like, the $(C_2-C_8)$ alkanoyl group may be substituted; $(C_3-C_8)$alkenoyl group such as propenoyl, butenoyl, pentenoyl and the like, $(C_3-C_8)$ alkenoyl group may be substituted; aroyl group such as benzoyl and the like, the aroyl group may be substituted; heteroaroyl group such as pyridyl carbonyl, furyl carbonyl and the like; the heteroaroyl group may be substituted; aralkenoyl group such as phenylpropenoyl, phenylbutenoyl, phenylpentenoyl and the like, the aralkenoyl group may be substituted; aralkanoyl group such as phenylpropanoyl, phenylbutanoyl, phenylpentanoyl and the like, the aralkanoyl group may be substituted; sulfonyl group such as methanesulfonyl, benzenesulfonyl, p-toluenesulfonyl and the like, the sulfonyl group may be substituted or a group $-(CO)-NH-R^7$ where $R^7$ represents linear or branched $(C_1-C_8)$alkyl group such as methyl, ethyl, n-propyl, iso-propyl and the like, $(C_1-C_8)$alkyl group may be substituted; aryl group such as phenyl, naphthyl and the like, the aryl group may be substituted; aralkyl such as benzyl, phenethyl and the like, the aralkyl group may be substituted.

The substituents on $R^1$, $R^a$, $R^b$, $R^2$, $R^3$ and $R^6$ may be selected from cyano, hydroxy, nitro, thio, halogen atom such as fluorine, chlorine, bromine and the like; substituted or unsubstituted groups selected from linear or branched $(C_1-C_8)$ alkyl group such as methyl, ethyl, n-propyl, iso-propyl and the like; amino, mono or disubstituted amino group, alkanoyl group such as ethanoyl, propanoyl, butanoyl and the like; thio$(C_1-C_8)$alkyl such as thiomethyl, thioethyl, thiopropyl and the like; $(C_1-C_6)$ alkoxy group such as methoxy, ethoxy, propyloxy, butyloxy and the like; aroyl group such as benzoyl and the like; acyloxy group such as acetyloxy, propanoyloxy, butanoyloxy and the like; aryl group such as phenyl, naphthyl and the like, the aryl group may be mono or disubstituted, heteroaryl group such as pyridyl, furyl, thienyl and the like; acylamino groups such as $CH_3CONH$, $C_2H_5CONH$, $C_3H_7CONH$, $C_4H_9CONH$ and $C_6H_5CONH$; aralkylamino group such as $C_6H_5CH_2NH$, $C_6H_5CH_2CH_2NH$, $C_6H_5CH_2NCH_3$ and the like; alkoxycarbonylamino group such as $C_4H_9OCONH$, $C_2H_5OCONH$, $CH_3OCONH$ and the like; aryloxycarbonylamino group such as $C_6H_5OCONH$, $C_6H_5OCONCH_3$, $C_6H_5OCONC_2H_5$, $C_6H_4(CH_3)OCONH$, $C_6H_4(OCH_3)OCONH$, and the like; aralkoxycarbonylamino group such as $C_6H_5CH_2OCONH$, $C_6H_5CH_2CH_2OCONH$, $C_6H_5CH_2OCON(CH_3)$, $C_6H_5CH_2OCON(C_2H_5)$, $C_6H_4(CH_3)CH_2OCONH$, $C_6H_4(OCH_3)CH_2OCONH$ and the like; $(C_1-C_8)$ alkylthio group such as methylthio, ethylthio, propylthio and the like; heteroarylthio group such as pyridylthio, furylthio, thiophenylthio, benzothiazolethio, purinethio, benzimidazolethio, pyrimidinethio and the like; acylthio group such as acetylthio, propanoylthio, butanoylthio and the like; aralkylthio group such as benzylthio, phenylethylthio, phenylpropylthio and the like; arylthio group such as phenylthio, napthylthio and the like; ($C_1$–$C_8$) alkylseleno such as methylseleno, ethylseleno, propylseleno, isopropylseleno and the like; acylseleno such as acetylseleno, propionylseleno and the like; aralkylseleno such as benzylseleno, phenylethylseleno, phenylpropylseleno and the like; arylseleno such as phenylseleno, napthylseleno and the like or COOR, where R represents hydrogen or ($C_1$–$C_6$) alkyl groups. The substituents are selected from halogen, hydroxy, nitro, cyano, amino, ($C_1$–$C_6$)alkyl, aryl or ($C_1$–$C_6$)alkoxy group.

The substituents on $R^7$ may be selected from hydroxy, halogen atom such as fluorine, chlorine or bromine, nitro, cyano, ($C_1$–$C_6$)alkyl, aryl, or aralkyl. These groups are as defined in $R^7$.

Suitable groups represented by $R^8$ include substituted or unsubstituted ($C_1$–$C_6$) alkyl such as methyl, ethyl, n-propyl and the like; aryl group such as phenyl, naphthyl and the like, the aryl group may be substituted; aralkyl such as benzyl, phenethyl and the like, the aralkyl group may be substituted; aroyl group such as benzoyl and the like, the aroyl group may be substituted. The substituents on the alkyl group, aromatic moiety of the aryl group, aralkyl group or aroyl group include halogen atom such as fluorine, chlorine and bromine; amino group, cyano, hydroxy, nitro, trifluoroethyl, ($C_1$–$C_6$) alkyl, or ($C_1$–$C_6$) alkoxy.

When the groups $R^1$, $R^a$, $R^b$, $R^2$, $R^3$, $R^6$, $R^7$ or $R^8$ represent disubstituted aryl, the two substituents on the adjacent carbon atoms form a linking group such as —X—$CH_2$—Y—, —X—$CH_2$—$CH_2$—Y, where X and Y may be same or different and independently represent O, NH, S or $CH_2$.

When the groups represented by $R^a$, $R^b$, $R^1$, $R^2$, $R^3$, $R^6$, $R^7$ or $R^8$ are multi substituted, the substituents present on the two adjacent carbons may form a linking group —X—($CR^{12}R^{13}$)$_n$—Y— where $R^{12}$ and $R^{13}$ represent ($C_1$–$C_8$) alkyl such as methyl, ethyl the like, X and Y may be same or different and independently represent $CH_2$, O, S, NH; and n=1 or 2.

Pharmaceutically acceptable salts forming part of this invention include salts derived from inorganic bases such as Li, Na, K, Ca, M, Fe, Cu, Zn, and Mn; salts of organic bases such as N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, ornithine, lysine, arginine, serine, threonine, and phenylalanine; unnatural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprise other solvents of crystallization such as alcohols.

Particularly useful compounds of the present invention include:

3,19-Diacetyl-12-(N-benzylamino)-14-deoxy andrographolide;
3,19-Diacetyl-12α-(N-benzylamino)-14-deoxy andrographolide;
3,19-Diacetyl-12β-(N-benzylamino)-14-deoxy andrographolide;
14-Deoxy-12-(O-methylphenylglycino)-3,19-O-(1-phenylethylidene)andrographolide;
14-Deoxy-12α-(O-methylphenylglycino)-3,19-O-(1-phenylethylidene)andrographolide;
14-Deoxy-12β-(O-methylphenylglycino)-3,19-O-(1-phenylethylidene)andrographolide;
3,19-Diacetyl-14-deoxy-12-(N-4-methoxybenzylamino) andrographolide;
3,19-Diacetyl-14-deoxy-12α-(N-4-methoxybenzylamino) andrographolide;
3,19-Diacetyl-14-deoxy-12β-(N-4-methoxybenzylamino) andrographolide;
3,19-Diacetyl-12-(N-2-chlorobenzylamino)-14-deoxy andrographolide;
3,19-Diacetyl-12α-(N-2-chlorobenzylamino)-14-deoxy andrographolide;
3,19-Diacetyl-12-β(N-2-chlorobenzylamino)-14-deoxy andrographolide;
3,19-Diacetyl-14-deoxy-12-(O-methylproino) andrographolide;
3,19-Diacetyl-14-deoxy-12α-(O-methylprolino) andrographolide;
3,19-Diacetyl-14-deoxy-12β-(O-methylprolino) andrographolide;
3,19-Diacetyl-14-deoxy-12-(O-methylphenylalano) andrographolide;
3,19-Diacetyl-14-deoxy-12α-(O-methylphenylalanino) andrographolide;
3,19-Diacetyl-14-deoxy-12β-(O-methylphenylalanino) andrographolide;
3,19-Diacetyl-14-deoxy-12-(O-methyl-3-phenylisoserino) andrographolide;
3,19-Diacetyl-14-deoxy-12α-(O-methyl-3-phenylisoserino) andrographolide;
3,19-Diacetyl-14-deoxy-12β-(O-methyl-3-phenylisoserino) andrographolide;
3,19-Diacetyl-14-deoxy-12-(O-methylmethionino) andrographolide;
3,19-Diacetyl-14-deoxy-12α-(O-methylmethionino) andrographolide;
3,19-Diacetyl-14-deoxy-12β-(O-methylmethionino) andrographolide;
3,19-Diacetyl-14-deoxy-12-(O-methylphenylglycino) andrographolide;
3,19-Diacetyl-14-deoxy-12α-(O-methylphenylglycino) andrographolide;
3,19-Diacetyl-14-deoxy-12β-(O-methylphenylglycino) andrographolide;
3,19-Diacetyl-14-deoxy-12-(O-methylalanino) andrographolide;
3,19-Diacetyl-14-deoxy-12α-(O-methylalanino) andrographolide;

3,19-Diacetyl-14-deoxy-12β-(O-methylalanino) andrographolide;
3,19-Diacetyl-14-deoxy-12-(O-methylglycino) andrographolide;
3,19-Diacetyl-14-deoxy-12α-(O-methylgycino) andrographolide;
3,19-Diacetyl-14-deoxy-12β-(O-methylglycino) andrographolide;
3,19-Diacetyl-14-deoxy-12-(O-methylselenomethionino) andrographolide;
3,19-Diacetyl-14-deoxy-12α-(O-methylselenomethionino) andrographolide;
3,19-Diacetyl-14-deoxy-12β-(O-methylselenomethionino) andrographolide;
3,19-Diacetyl-14-deoxy-12-N-imidazolyl)androgapholide;
3,19-Diacetyl-14-deoxy-12α-(N-imidazolyl) andrographolide;
3,19-Diacetyl-14-deoxy-12β-(N-imidazolyl) andrographolide;
3,19-Diacetyl-14-deoxy-12-(N-methypiperazino) andrographolide;
3,19-Diacetyl-14-deoxy-12α-(N-methypiperazino) andrographolide;
3,19-Diacetyl-14-deoxy-12β-(N-methylpiperazino) andrographolide;
3,19-Diacetyl-14-deoxy-12-morpholino andrographolide;
3,19-Diacetyl-14-deoxy-12α-morpholino andrographolide;
3,19-Diacetyl-14-deoxy-12β-morpholino andrographolide;
3,19-Diacetyl-12-(N-acetylpiperazino)-14-deoxy andrographolide;
3,19-Diacetyl-12α-(N-acetylpiperazino)-14-deoxy andrographolide;
3,19-Diacetyl-12β-(N-acetylpiperazino)-14-deoxy andrographolide;
12-(N-Benzylamino)-14-deoxy andrographolide;
12α-(N-Benzylamino)-14-deoxy andrographolide;
12β-(N-Benzylamino)-14-deoxy andrographolide;
14-Deoxy-12-(O-methylphenylglycino)andrographolide;
14-Deoxy-12α-(O-methylphenylglycino)andrographolide;
14-Deoxy-12β-(O-methylphenylglycino)andrographolide;
14-Deoxy-3,19-O-isopropylidene-12-(methylphenylalanino)andrographolide;
14-Deoxy-3,19-O-isopropylidene-12α-(methylphenylalanino)andrographolide;
14-Deoxy-3,19-O-isopropylidene-12β-(methylphenylalanino)andrographolide;
12-(N-Benzylamino)-14-deoxy-3,19-O-(1-phenylethylidene)andrographolide;
12α-(N-Benzylamino)-14-deoxy-3,19-O-(1-phenylethylidene)andrographolide;
12β-(N-Benzylamino)-14-deoxy-3,19-O-(1-phenylethylidene)andrographolide;
14-Deoxy-12-(O-methylphenylalanino)-3,19-O-(1-phenylethylidene)andrographolide;
14-Deoxy-12α-(O-methylphenylalanino)-3,19-O-(1-phenylethylidene)andrographolide;
14-Deoxy-12β-(O-methylphenylalanino)-3,19-O-(1-phenylethylidene)andrographolide;
14-Deoxy-12-(O-methylprolino)-3,19-O-(1-phenylethylidene)andrographolide;
14-Deoxy-12α-(O-methylprolino)-3,19-O-(1-phenylethylidene)andrographolide;
14-Deoxy-12β-(O-methylprolino)-3,19-O-(1-phenylethylidene)andrographolide;
3,19-O-Benzylidene-12-(N-benzylamino)-14-deoxy andrographolide;
3,19-O-Benzylidene-12α-(N-benzylamino)-14-deoxy andrographolide;
3,19-O-Benzylidene-12β-(N-benzylamino)-14-deoxy andrographolide;
3,19-Diacetyl-14-deoxy-8,17-epoxy-12-(O-methylnethionino)andrographolide;
3,19-Diacetyl-14-deoxy-8,17-epoxy-12α-(O-methylmethionino)andrographolide;
3,19-Diacetyl-14-deoxy-8,17-epoxy-12β-(O-methylmethionino)andrographolide;
3,19-Diacetyl-14-deoxy-8,17-epoxy-12-(O-methylphenylglycino)andrographolide;
3,19-Diacetyl-14-deoxy-8,17-epoxy-12α-(O-methylphenylglycino)andrographolide;
3,19-Diacetyl-14-deoxy-8,17-epoxy-12β-(O-methylphenylglycino)andrographolide;
3,19-Diacetyl-14-deoxy-12-(N-1,2,4-triazolyl) andrographolide;
3,19-Diacetyl-14-deoxy-12α-(N-1,2,4-triazolyl) andrographolide;
3,19-Diacetyl-14-deoxy-12β-(N-1,2,4-triazolyl) andrographolide;
14-Deoxy-12-(2,3-dimethylanilino)andrographolide;
14-Deoxy-12α-(2,3-dimethylanilino)andrographolide;
14-Deoxy-12β-(2,3-dimethylanilino)andrographolide;
3,19-Diacetyl-14-deoxy-12-(4-methoxy-2-methylanilino) andrographolide;
3,19-Diacetyl-14-deoxy-12α-(4-methoxy-2-methylanilino) andrographolide;
3,19-Diacetyl-14-deoxy-12β-(4-methoxy-2-methylanilino) andrographolide;
3,19-Diacetyl-14-deoxy-12-(4-hydroxy-2-methylanilino) andrographolide;
3,19-Diacetyl-14-deoxy-12α-(4-hydroxy-2-methylanilino) andrographolide;
3,19-Diacetyl-14-deoxy-12β-(4-hydroxy-2-methylanilino) andrographolide;
3,19-Diacetyl-14-deoxy-12-(2-mercaptoanilino) andrographolide;
3,19-Diacetyl-14-deoxy-12α-(2-mercaptoanilino) andrographolide;
3,19-Diacetyl-14-deoxy-12β-(2-mercaptoanilino) andrographolide;
3,19-Diacetyl-14-deoxy-12-(3,4-dimethoxyanilino) andrographolide;
3,19-Diacetyl-14-deoxy-12α-(3,4-dimethoxyanilino) andrographolide;
3,19-Diacetyl-14-deoxy-12β-(3,4-dimethoxyanilino) andrographolide;
3,19-Diacetyl-12-anilino-14-deoxy andrographolide;
3,19-Diacetyl-12α-anilino-14-deoxy andrographolide;
3,19-Diacetyl-12β-anilino-14-deoxy andrographolide;
3,19-Diacetyl-14-deoxy-12-(2,3-dimethylanilino) andrographolide;
3,19-Diacetyl-14-deoxy-12α-(2,3-dimethylanilino) andrographolide;
3,19-Diacetyl-14-deoxy-12β-(2,3-dimethylanilino) andrographolide;
3,19-Diacetyl-14-deoxy-12-(2-methyl-4-methylsulfonateanilino)andrographolide;
3,19-Diacetyl-14-deoxy-12α-(2-methyl-4-methylsulfonateanilino)andrographolide;
3,19-Diacetyl-14-deoxy-12β-(2-methyl-4-methylsulfonateanilino)andrographolide;
3,19-Diacetyl-14-deoxy-12-(2-tetrazolylamino) andrographolide;
3,19-Diacetyl-14-deoxy-12α-(N-tetrazolylamino) andrographolide;
3,19-Diacetyl-14-deoxy-12β-(N-tetrazolylamino) andrographolide;

14-Deoxy-12-(3,4-dimethoxyanilino)andrographolide;
14-Deoxy-12α-(3,4-dimethoxyanilino)andrographolide;
14-Deoxy-12β-(3,4-dimethoxyanilino)andrographolide;
14-Deoxy-3,19-O-isopropylidene-12-(2,3-dimethylanilino)andrographolide;
14-Deoxy-3,19-O-isopropylidene-12α-(2,3-dimethylanilino)andrographolide;
14-Deoxy-3,19-O-isopropylidene-12β-(2,3-dimethylanilino)andrographolide;
14-Deoxy-12-(2-methylanilino)-3,19-O-(1-phenylethylidene)andrographolide;
14-Deoxy-12α-(2-methylanilino)-3,19-O-(1-phenylethylidene)andrographolide;
14-Deoxy-12β-(2-methylanilino)-3,19-O-(1-phenylethylidene)andrographolide;
3,19-O-Benzylidene-14-deoxy-12-(2,3-dimethylanilino)andrographolide;
3,19-O-Benzylidene-14-deoxy-12α-(2,3-dimethylanilino)andrographolide;
3,19-O-Benzylidene-14-deoxy-12β-(2,3-dimethylanilino)andrographolide;
3,19-Diacetyl-12-anilino-14-deoxy-8,17-epoxy andrographolide;
3,19-Diacetyl-12α-anilino-14-deoxy-8,17-epoxy andrographolide;
3,19-Diacetyl-12β-anilino-14-deoxy-8,17-epoxy andrographolide;
3,19-Diacetyl-14-deoxy-8,17-epoxy-12-(2,3-dimethylanilino)andrographolide;
3,19-Diacetyl-14-deoxy-8,17-epoxy-12α-(2,3-dimethylanilino)andrographolide;
3,19-Diacetyl-14-deoxy-8,17-epoxy-12β-(2,3-dimethylanilino)andrographolide;
14-Deoxy-12-($N^1$-uracil)andrographolide;
14-Deoxy-12α-($N^1$-uracil)andrographolide;
14-Deoxy-12β-($N^1$-uracil)andrographolide;
3,19-Diacetyl-14-deoxy-12-[N-(1,2-dihydro-2-pyrimidinone)amino]-1-andrographolide;
3,19-Diacetyl-14-deoxy-12α-[N-(1,2-dihydro-2-pyrimidinone)amino]-1-andrographolide;
3,19-Diacetyl-14-deoxy-12β-[N-(1,2-dihydro-2-pyrimidinone)amino]-1-andrographolide;
3,19-Diacetyl-14-deoxy-12-($N^1$-uracil)andrographolide;
3,19-Diacetyl-14-deoxy-12α-($N^1$-uracil)andrographolide;
3,19-Diacetyl-14-deoxy-12β-($N^1$-uracil)andrographolide;
3,19-Diacetyl-14-deoxy-12-[$N^1$-(5-chlorouracil)]andrographolide;
3,19-Diacetyl-14-deoxy-12α-[$N^1$-(5-chlorouracil)]andrographolide;
3,19-Diacetyl-14-deoxy-12β-[$N^1$-(5-chlorouracil)]andrographolide;
3,19-Diacetyl-14-deoxy-12-[$N^1$-(5-bromouracil)]andrographolide;
3,19-Diacetyl-14-deoxy-12α-[$N^1$-(5-bromouracil)]andrographolide;
3,19-Diacetyl-14-deoxy-12β-[$N^1$-(5-bromouracil)]andrographolide;
3,19-Diacetyl-14-deoxy-12-[$N^1$-(5-fluorouracil)]andrographolide;
3,19-Diacetyl-14-deoxy-12α-[$N^1$-(5-fluorouracil)]andrographolide;
3,19-Diacetyl-14-deoxy-12β-[$N^1$-(5-fluorouracil)]andrographolide;
3,19-Diacetyl-14-deoxy-12-[$N^1$-(5-iodouracil)]andrographolide;
3,19-Diacetyl-14-deoxy-12α-[$N^1$-(5-iodouracil)]andrographolide;
3,19-Diacetyl-14-deoxy-12β-[$N^1$-(5-iodouracil)]andrographolide;
14-Deoxy-12-[N-(1,2-dihydro-2-pyrimidinone)amino]andrographolide;
14-Deoxy-12α-[N-(1,2-dihydro-2-pyrimidinone)amino]andrographolide;
14-Deoxy-12β-[N-(1,2-dihydro-2-pyrimidinone)amino]andrographolide;
14-Deoxy-12-[$N^1$-(5-fluorouracil)]andrographolide;
14-Deoxy-12α-[N-(5-fluorouracil)]andrographolide;
14-Deoxy-12β-[$N^1$-(5-fluorouracil)]andrographolide;
14-Deoxy-12-[$N^1$-(5-bromouracil)]andrographolide;
14-Deoxy-12α-[$N^1$-(5-bromouracil)]andrographolide;
14-Deoxy-12β-[$N^1$-(5-bromouracil)]andrographolide;
14-Deoxy-12-[$N^1$-(5-iodouracil)]andrographolide;
14-Deoxy-12α-[$N^1$-(5-bodouracil)]andrographolide;
14-Deoxy-12β-[$N^1$-(5-iodouracil)]andrographolide;
14-Deoxy-8,17-epoxy-12-phenylthio andrographolide;
14-Deoxy-8,17-epoxy-12α-phenylthio andrographolide;
14-Deoxy-8,17-epoxy-12β-phenylthio andrographolide;
3,19-Diacetyl-14-deoxy-12-phenylseleno andrographolide;
3,19-Diacetyl-14-deoxy-12α-phenylseleno andrographolide;
3,19-Diacetyl-14-deoxy-12β-phenylseleno andrographolide;
12-(C-Benzoylmethyl)-14-deoxy-13,19-O-(1-phenylethylidene)andrographolide;
12α-(C-Benzoylmethyl)-14-deoxy-13,19-O-(1-phenylethylidene)andrographolide;
12β-(C-Benzoylmethyl)-14-deoxy-13,19-O-(1-phenylethylidene)andrographolide;
14-Deoxy-3,19-O-isopropylidene-12-ethylthio andrographolide;
14-Deoxy-3,19-O-isopropylidene-12α-ethylthio andrographolide;
14-Deoxy-3,19-O-isopropylidene-12β-ethylthio andrographolide;
3,19-Diacetyl-14-deoxy-12-phenylthio andrographolide;
3,19-Diacetyl-14-deoxy-12α-phenylthio andrographolide;
3,19-Diacetyl-14-deoxy-12β-phenylthio andrographolide;
3,19-Diacetyl-14-deoxy-12-acetylthio andrographolide;
3,19-Diacetyl-14-deoxy-12α-acetylthio andrographolide;
3,19-Diacetyl-14-deoxy-12β-acetylthio andrographolide;
3,19-Diacetyl-14-deoxy-12-ethylthio andrographolide;
3,19-Diacetyl-14-deoxy-12α-ethylthio andrographolide;
3,19-Diacetyl-14-deoxy-12β-ethylthio andrographolide;
3,19-Diacetyl-12-benzyl-14-deoxy andrographolide;
3,19-Diacetyl-12α-benzyl-14-deoxy andrographolide;
3,19-Diacetyl-12β-benzyl-14-deoxy andrographolide;
3,19-Diacetyl-14-deoxy-12-(1,1'-diethyl dicarboxylate methyl)andrographolide;
3,19-Diacetyl-14-deoxy-12α-(1,1'-diethyl dicarboxylate methyl)andrographolide;
3,19-Diacetyl-14-deoxy-12β-(1,1'-diethyl dicarboxylate methyl)andrographolide;
14-Deoxy-12-phenylthio andrographolide;
14-Deoxy-12α-phenythio andrographolide;
14-Deoxy-12β-phenylthio andrographolide;
14-Deoxy-12-ethylthio andrographolide;
14-Deoxy-12α-ethylthio andrographolide;
14-Deoxy-12β-ethylthio andrographolide;
14-Deoxy-12-phenylseleno andrographolide;
14-Deoxy-12α-phenylseleno andrographolide;
14-Deoxy-12β-phenylseleno andrographolide;
14-Deoxy-3,19-O-isopropylidene-12-phenylthio andrographolide;
14-Deoxy-3,19-O-isopropylidene-12α-phenylthio andrographolide;

14-Deoxy-3,19-O-isopropylidene-12β-phenylthio andrographolide;
14-Deoxy-3,19-O-(1-phenylethylidene)-12-phenylthio andrographolide;
14-Deoxy-3,19-O-(1-phenylethylidene)-12α-phenylthio andrographolide;
14-Deoxy-3,19-O-(1-phenylethylidene)-12β-phenylthio andrographolide;
14-Deoxy-3,19-O-(1-phenylethylidene)-12-ethylthio andrographolide;
14-Deoxy-3,19-O-(1-phenylethylidene)-12α-ethylthio andrographolide;
14-Deoxy-3,19-O-(1-phenylethylidene)-12β-ethylthio andrographolide;
3,19-O-Benzylidene-14-deoxy-12-phenylthio andrographolide;
3,19-O-Benzylidene-14-deoxy-12α-phenylthio andrographolide;
3,19-O-Benzylidene-14-deoxy-12β-phenylthio andrographolide;
3,19-Diacetyl-14-deoxy-8,17-epoxy-12-phenylthio andrographolide;
3,19-Diacetyl-14-deoxy-8,17-epoxy-12α-phenylthio andrographolide;
3,19-Diacetyl-14-deoxy-8,17-epoxy-12β-phenylthio andrographolide;
12-Cinnamoyloxy-14-deoxy andrographolide;
12α-Cinnamoyloxy-14-deoxy andrographolide;
12β-Cinnamoyloxy-14-deoxy andrographolide;
12-Cinnamoyloxy-14-deoxy-8,17-epoxy andrographolide;
12α-Cinnamoyloxy-14-deoxy-8,17-epoxy andrographolide;
12β-Cinnamoyloxy-14-deoxy-8,17-epoxy andrographolide;
14-Deoxy-12-hydroxy andrographolide;
14-Deoxy-12α-hydroxy andrographolide;
14-Deoxy-12β-hydroxy andrographolide;
12-Acetoxy-3,19-diacetyl-14-deoxy andrographolide;
12α-Acetoxy-3,19-diacetyl-14-deoxy andrographolide;
12β-Acetoxy-3,19-diacetyl-14-deoxy andrographolide;
3,19-Diacetyl-14-deoxy-12-methoxy andrographolide;
3,19-Diacetyl-14-deoxy-12α-methoxy andrographolide;
3,19-Diacetyl-14-deoxy-12β-methoxy andrographolide;
3,19-Diacetyl-14-deoxy-12-(2-acetoxy-3-N-acetylamino-3-phenylpropionyloxy)andrographolide;
3,19-Diacetyl-14-deoxy-12α-(2-acetoxy-3-N-acetylamino-3-phenylpropionyloxy)andrographolide;
3,19-Diacetyl-14-deoxy-12β-(2-acetoxy-3-N-acetylamino-3-phenylpropionyloxy)andrographolide;
12-(N-Boc glycinyloxy)-14-deoxy-8,17-epoxy-3,19-dipropionyl andrographolide;
12α-(N-Boc glycinyloxy)-14-deoxy-8,17-epoxy-3,19-dipropionyl andrographolide;
12β-(N-Boc glycinyloxy)-14-deoxy-8,17-epoxy-3,19-dipropionyl andrographolide;
3,19-Diacetyl-14-deoxy-12-mercaptobenzothiazolyl andrographolide;
3,19-Diacetyl-14-deoxy-12α-mercaptobenzothiazolyl andrographolide;
3,19-Diacetyl-14-deoxy-12β-mercaptobenzothiazolyl andrographolide;
3,19-Diacetyl-12-(N,N-benzylchloroacetyl)amino-14-deoxy-12 andrographolide;
3,19-Diacetyl-12α-(N,N-benzylchloroacetyl)amino-14-deoxy-12-andrographolide; and
3,19-Diacetyl-12β-(N,N-benzylchloroacetyl)amino-14-deoxy-12-andrographolide.

The present invention also provides a process for the preparation of novel derivatives of andrographolide of the general formula (I), where $R^1$ represents hydrogen, halogen, thio, or substituted or unsubstituted alkyl, alkylthio, heteroarylthio, acylthio, aralkylthio, arylthio, alkylseleno, acylseleno, aralkylseleno, arylseleno, $NR^a R^b$ where $R^a$, and $R^b$ may be same or different and independently represent hydrogen, or substituted or unsubstituted alkyl, aryl, acyl, aralkyl, heteroaryl, haloalkyl, or haloacyl or $R^a$ and $R^b$ together with the nitrogen atom to which they are attached may form substituted or unsubstituted 5 or 6 membered cyclic ring system containing carbon atoms, at least one nitrogen and optionally one or more hetero atoms selected from oxygen, sulfur or nitrogen, the cyclic ring system may contain one or two double bonds or it may be aromatic or $R^1$ may represent $OR^6$ where $R^6$ represents hydrogen or substituted or unsubstituted groups selected from alkyl, aryl, aralkyl, alkenoyl, alkanoyl, aroyl, heteroaroyl, aralkenoyl, aralkanoyl, sulfonyl groups or a group —(CO)—NH—$R^7$ where $R^7$ represents substituted or unsubstituted groups selected from alkyl, aryl, or aralkyl; $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, aralkenoyl, aralkanoyl, sulfonyl group or a group —(CO)—W—$R^8$ where W represents O, S or $NR^9$, wherein $R^9$ represents hydrogen or $(C_1–C_6)$alkyl group, $R^8$ represents substituted or unsubstituted groups selected from alkyl, aryl, aralkyl or aroyl or $OR^2$ and $OR^3$ together form a substituted or unsubstituted 6 or 7 membered cyclic structure containing carbon and oxygen atoms; $R^4$ and $R^5$ together represents =$CH_2$ or an epoxide group; their stereoisomers, their polymorphs, their pharmaceutically acceptable salts or their pharmaceutically acceptable solvates, which comprises:

(i) protecting andrographolide derivative of the formula (VII), (VII)

where $R^4$ and $R^5$ are as defined earlier, to produce a compound of formula (VIII), (VIII)

where $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene and the like; and $R^4$ and $R^5$ are as defined earlier, (iii) converting the compound of formula (VIII) to a compound of formula (IX),

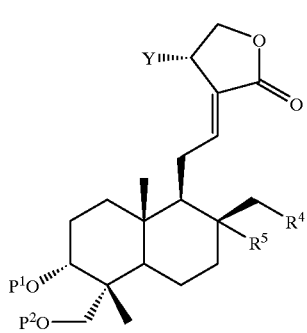

(IX)

where Y represents halogen atom such as fluorine, chlorine, bromine, iodine or esters such as sulfonyl chloride, acetate, propionate, benzoate and the like or sulfonyl esters such as mesylate, tosylate, triflate and the like; $P^1$ and $p^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene and the like; and $R^4$ and $R^5$ are as defined earlier, (iii) reacting andrographolide derivative of the formula (IX) with a suitable nucleophile to produce a compound of formula (X)

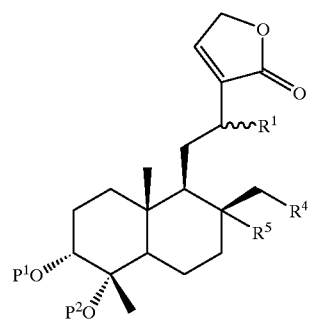

(X)

where all symbols are as defined earlier and if desired, (iv) deprotecting the compound of formula (X) by conventional methods to produce a compound of formula (XI),

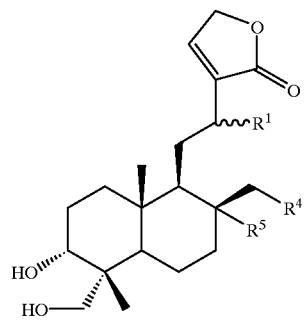

(XI)

where all symbols are as defined earlier and (v) reacting the compound of formula (XI) with $R^2$-L and/or $R^3$-L, where L represents a leaving group such as hydroxy, halogen atom like fluorine, chlorine, bromine, or iodine; p-toluenesulfonate, methanesulfonate, trifluoromethanesulfonate; or acyl groups such as acetate, propanoate, butanoate and the like; and $R^2$ and $R^3$ are as defined above to produce a compound of formula (I), and if desired, (vi) converting compound of formula (I) into its stereoisomers, and/or pharmaceutical salts by conventional methods.

The protection of a compound of formula (VII) may be carried out using trityl chloride, t-butyldimethylsilyl chloride, pivaloyl chloride, dimethylsulfoxide, acetone, 2,2-dimethoxy propane, trimethyl ortho acetate, benzaldehyde, p-methoxy benzaldehyde, acetophenone and the like. The reaction may be carried out in the presence of a suitable catalyst such as $SOCl_2$, $H_2SO_4$, $HClO_4$, pyridinium p-toluene sulphonate, pyridine, p-toluene sulfonic acid, dimethyl aminopyridine, and the like. The reaction may be carried out in the absence or presence of suitable solvent such as benzene, DMF, dimethylsulfoxide (DMSO), acetonitrile, dichloromethane (DCM), and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h.

The conversion of compound of formula (VIII) to compound of formula (IX) may be carried out using halogenating agents such as thionyl chloride, thionyl bromide, phosphonyl chloride, $PCl_5$, $PBr_3$, bromine trifluoride, N-bromosuccinimide-hydrogen fluoride (NBS-HF), cobalt (III) fluoride, lithium fluoride, potassium fluoride, sodium fluoride, cesium fluoride, potassium iodide, sodium, iodide, iodine, iodine cerium (IV) ammonium nitrate, or R-L where R is acetyl, propionyl, benzoyl, mesyl, tosyl, triflyl and the like and L is as defined above. The reaction may be carried out in the presence of solvents such as ether, dichloromethane, chloroform, DMF, DMSO and the like. The reaction may be carried out in the range of −40° C. to 160° C. The duration of the reaction may range from 1 to 6 h.

The reaction of compound of formula (IX) with nucleophiles such as aniline, benzylamine, arylthio, piperazine, morpholine, imidazole, aminotetrazole, triazole, esters of α-aminoacids, esters of β-amino acids, acetic acid, thioacetic acid, alkyl magnesium halide, aryl magnesium halide, methanol, ethanol, propanol and the like may be carried out in the presence of solvents such as ether, DCM, DMF, and the like. The reaction may be carried out in the absence or presence of alumina. The reaction temperature may range from 80° C. to 100° C. and the reaction time may range from 1–10 h.

The deprotection of a compound of formula (X) to produce a compound of formula (XI) may be carried out using deprotecting agent such as acetic acid, hydrochloric acid, formic acid, trifluoroacetic acid and the like. The reaction may be carried out in the presence of suitable solvent such as water, THF, dioxane, DCM, $CHCl_3$, methanol and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h.

The reaction of compound of formula (XI) with $R^2$-L and $R^3$-L, to produce a compound of formula (I) may be carried out in the presence of dicyclohexylcarbodiimide (DCC), diethyl azadicarboxylate (DEAD), diisopropyl azadicarboxylate (DIAD) and the like. The reaction may be carried out in the absence or presence of a base selected from triethylamine, pyridine, dimethyl aminopyridine and the like. The reaction may be carried out in the presence of solvents such as dichloromethane, chloroform, $C_6H_6$, dimethyl sulfoxide, methanol, ethanol and the like or mixtures thereof. The reaction may be carried out at a temperature in the range of 0° C. to 200° C., preferably at a temperature in the range of 20° C. to 160° C. and the reaction time may range from 2 to 12 h, preferably from 2 to 10 h.

In yet another embodiment of the present invention, there is provided a novel intermediate of formula (IX)

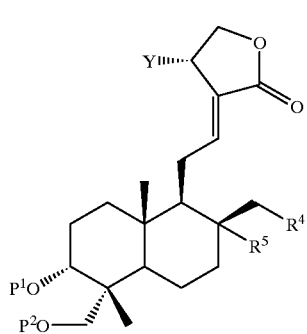

(IX)

where Y represents halogen atom such as fluorine, chlorine, bromine, iodine or esters such as sulfonyl chloride, acetate, propionate, benzoate and the like or sulfonyl esters such as mesylate, tosylate, triflate and the like; $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene and the like; and $R^4$ and $R^5$ together represent $=CH_2$ or an epoxide group.

The present invention also provides a process for the preparation of compound of formula (IX), their stereoisomers, their polymorphs, their pharmaceutically acceptable salts or their pharmaceutically acceptable solvates, which comprises:

(i) protecting andrographolide derivative of the formula (VII),

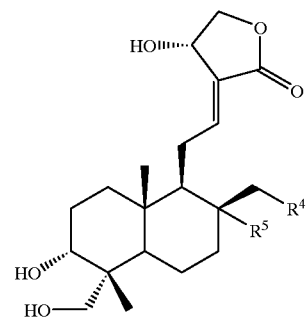

(VII)

where $R^4$ and $R^5$ are as defined earlier, to produce a compound of formula (VIII),

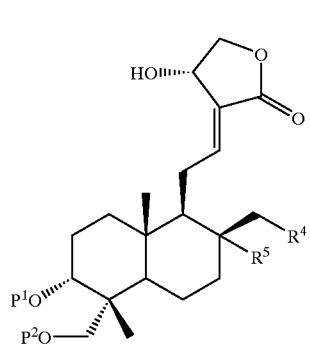

(VIII)

where $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene and the like; and $R^4$ and $R^5$ are as defined earlier, (ii) converting the compound of formula (VIII) to a compound of formula (IX),

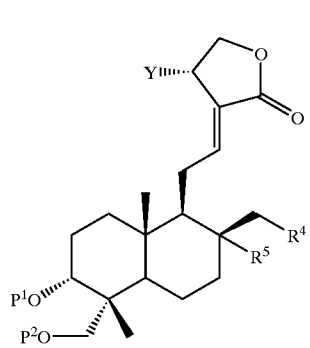

(IX)

where Y represents halogen atom such as fluorine, chlorine, bromine, iodine or esters such as sulfonyl chloride, acetate, propionate, benzoate and the like or sulfonyl esters such as mesylate, tosylate, triflate and the like; $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene and the like; and $R^4$ and $R^5$ are as defined earlier.

The protection of a compound of formula (VII) may be carried out using trityl chloride, t-butyldimethylsilyl chloride, pivaloyl chloride, dimethylsulfoxide, acetone, 2,2-dimethoxy propane, trimethyl ortho acetate, benzaldehyde, p-methoxy benzaldehyde, acetophenone and the like. The reaction may be carried out in the presence of a suitable catalyst such as $SOCl_2$, $H_2SO_4$, $HClO_4$, pyridinium p-toluene sulphonate, pyridine, p-toluene sulfonic acid, dimethyl aminopyridine, and the like. The reaction may be carried out in the absence or presence of suitable solvent such as benzene, DMF, dimethylsulfoxide (DMSO), acetonitrile, dichloromethane (DCM), and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h.

The conversion of compound of formula (VIII) to compound of formula (IX) may be carried out using halogenating agents such as thionyl chloride, thionyl bromide, phosphonyl chloride, PCl$_5$, PBr$_3$, bromine trifluoride, N-bromosuccinimide-hydrogen fluoride (NBS-HF), cobalt (III) fluoride, lithium fluoride, potassium fluoride, sodium fluoride, cesium fluoride, potassium iodide, sodium iodide, iodine, iodine cerium (IV) amnmonium nitrate, or R-L where R is acetyl, propionyl, benzoyl, mesyl, tosyl, triflyl and the like and L is as defined above. The reaction may be carried out in the presence of solvents such as ether, dichloromethane, chloroform, DMF, DMSO and the like; The reaction may be carried out in the range of −40° C. to 160° C. The duration of the reaction may range from 1 to 6 h.

In yet another embodiment of the present invention, there is provided a novel intermediate of formula (X)

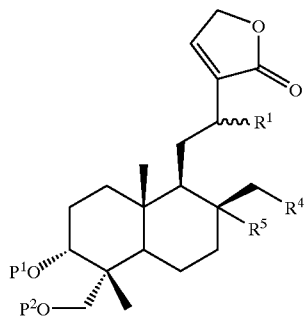

(X)

where $R^1$ represents hydrogen, halogen, thio, or substituted or unsubstituted alkyl, alkylthio, heteroarylthio, acylthio, aralkylthio, arylthio, alkylseleno, acylseleno, aralkylseleno, arylseleno, $NR^aR^b$ where $R^a$, and $R^b$ may be same or different and independently represent hydrogen, or substituted or unsubstituted alkyl, aryl, acyl, aralkyl, heteroaryl, haloalkyl, haloacyl or $R^a$ and $R^b$ together with the nitrogen atom to which they are attached may form substituted or unsubstituted 5 or 6 membered cyclic ring system containing carbon atoms, at least one nitrogen atom and optionally one or more hetero atoms selected from oxygen, sulfur or nitrogen, the cyclic ring system may contain one or two double bonds or it may be aromatic or $R^1$ may represent $OR^6$ where $R^6$ represents hydrogen or substituted or unsubstituted groups selected from alkyl, aryl, or aralkyl, alkenoyl, alkanoyl, aroyl, heteroaroyl, aralkenoyl, aralkanoyl, sulfonyl groups or a group —(CO)—NH—$R^7$ where $R^7$ represents substituted or unsubstituted groups selected from alkyl, aryl, or aralkyl; $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene and the like; $R^4$ and $R^5$ together represents =CH$_2$ or an epoxide group.

The present invention also provides a process for the preparation of novel intermediates of the formula (X), their stereoisomers, their polymorphs, their pharmaceutically acceptable salts or their pharmaceutically acceptable solvates, which comprises:

(i) protecting andrographolide derivative of the formula (VII),

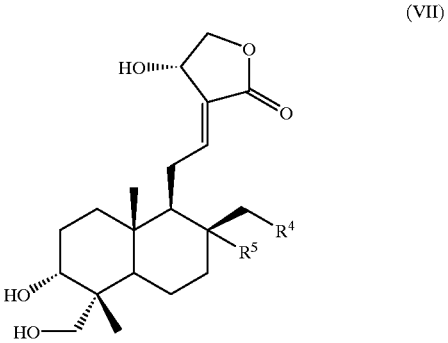

(VII)

where $R^4$ and $R^5$ are as defined earlier, to produce a compound of formula (VIII),

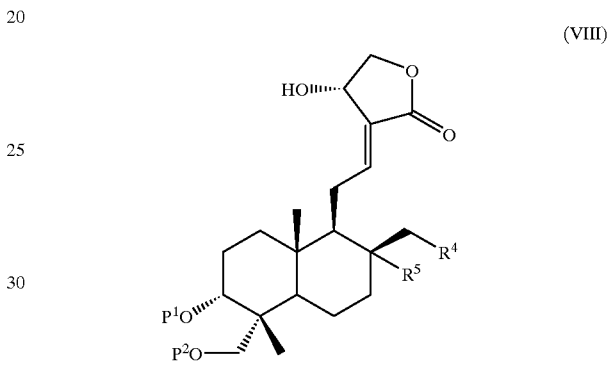

(VIII)

where $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene and the like; and $R^4$ and $R^5$ are as defined earlier, (ii) converting the compound of formula (VIII) to a compound of formula (IX),

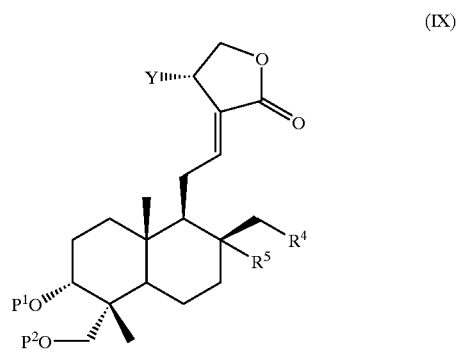

(IX)

where Y represents halogen atom such as fluorine, chlorine, bromine, iodine or esters such as sulfonyl chloride acetate, propionate, benzoate and the like or sulfonyl esters such as mesylate, tosylate, triflate and the like; $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene and the like; and $R^4$ and $R^5$ are as defined earlier, (iii) reacting andrographolide derivative of the formula (IX) with a suitable nucleophile to produce compound of formula (X).

The protection of a compound of formula (VII) may be carried out using trityl chloride, t-butyldimethylsilyl chloride, pivaloyl chloride, dimethylsulfoxide, acetone, 2,2-dimethoxy propane, trimethyl ortho acetate, benzaldehyde, p-methoxy benzaldehyde, acetophenone and the like. The reaction may be carried out in the presence of a suitable catalyst such as $SOCl_2$, $H_2SO_4$, $HClO_4$, pyridinium p-toluene sulphonate, pyridine, p-toluene sulfonic acid, dimethyl aminopyridine, and the like. The reaction may be carried out in the absence or presence of suitable solvent such as benzene, DMF, dimethylsulfoxide (DMSO), acetonitrile, dichloromethane (DCM), and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h.

The conversion of compound of formula (VIII) to compound of formula (IX) may be carried out using halogenating agents such as thionyl chloride, thionyl bromide, phosphonyl chloride, $PCl_5$, $PBr_3$, bromine trifluoride, N-bromosuccinimide-hydrogen fluoride (NBS-HF), cobalt (III) fluoride, lithium fluoride, potassium fluoride, sodium fluoride, cesium fluoride, potassium iodide, sodiumiodide, iodine, iodine cerium (IV) ammonium nitrate, or R-L where R is acetyl, propionyl, benzoyl, mesyl, tosyl, triflyl and the like and L is as defined above. The reaction may be carried out in the presence of solvents such as ether, dichloromethane, chloroform, DMF, DMSO and the like; The reaction may be carried out in the range of −40° C. to 160° C. The duration of the reaction may range from 1 to 6 h.

The reaction of compound of formula (IX) with nucleophiles such as aniline, benzylamine, arylthio, piperazine, morpholine, imidazole, aminotetrazole, triazole, ester of α-aminoacids, esters of β-amino acids, acetic acid, thioacetic acid, alkyl magnesium halide, aryl magnesium halide, methanol, ethanol, propanol and the like may be carried out in the presence of solvents such as ether, DCM, DMF, and the like. The reaction may be carried out in the absence or presence of alumina. The reaction temperature may range from 80° C. to 100° C. and the reaction time may range from 1–10 h.

In still another embodiment of the present invention, there is provided a novel intermediate of formula (XI)

(XI)

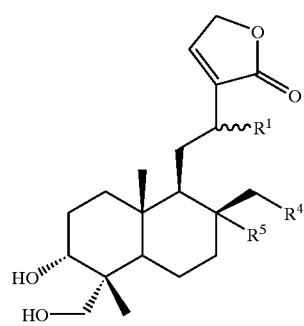

where $R^1$ represents hydrogen, halogen, thio, or substituted or unsubstituted alkyl, alkylthio, heteroarylthio, acylthio, aralkylthio, arylthio, alkylseleno, acylseleno, aralkylseleno, arylseleno, $NR^aR^b$ where $R^a$ and $R^b$ may be same or different and independently represent hydrogen, or substituted or unsubstituted alkyl, aryl, acyl, aralkyl, heteroaryl, haloalkyl, or haloacyl or $R^a$ and $R^b$ together with the nitrogen atom to which they are attached may form substituted or unsubstituted 5 or 6 membered cyclic ring system containing carbon atoms, at least one nitrogen atom and optionally one or more hetero atoms selected from oxygen, sulfur or nitrogen, the cyclic ring system may contain one or two double bonds or it may be aromatic or $R^1$ may represent $OR^6$ where $R^6$ represents hydrogen or substituted or unsubstituted groups selected from alkyl, aryl, aralkyl, alkenoyl, alkanoyl, aroyl, heteroaroyl, aralkenoyl, aralkanoyl, sulfonyl groups or a group —(CO)—NH—$R^7$ where $R^7$ represents substituted or unsubstituted groups selected from alkyl, aryl, or aralkyl; $R^4$ and $R^5$ together represents $=CH_2$ or an epoxide group, their stereoisomers, their polymorphs, their pharmaceutically acceptable salts and their pharmaceutically acceptable solvates.

The present invention also provides a process for the preparation of novel intermediate of formula (XI), their stereoisomers, their polymorphs, their pharmaceutically acceptable salts or their pharmaceutically acceptable solvates, which comprises:

(i) protecting andrographolide derivative of the formula (VII), (VII)

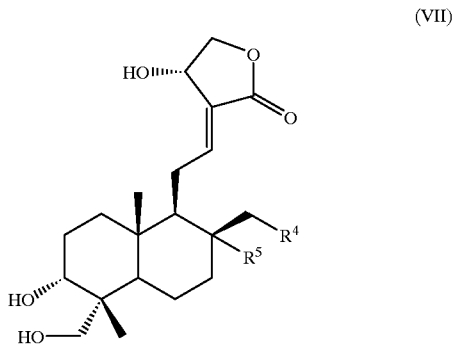

where $R^4$ and $R^5$ are as defined earlier, to produce a compound of formula (VIII), (VIII)

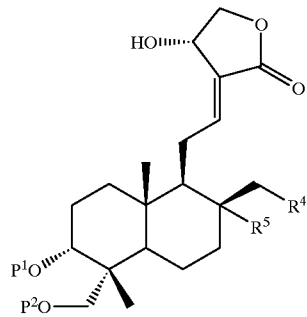

where $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene and the like; and $R^4$ and $R^5$ are as defined earlier, (ii) converting the compound of formula (VIII) to a compound of formula (IX),

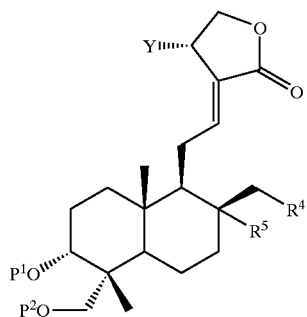

(IX)

where Y represents halogen atom such as fluorine, chlorine, bromine, iodine or esters such as sulfonyl chloride, acetate, propionate, benzoate and the like or sulfonyl esters such as mesylate, tosylate, triflate and the like; $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene and the like; $R^4$ and $R^5$ are as defined earlier, (iii) reacting andrographolide of the formula (IX) with a suitable nucleophile to produce a compound of formula (X)

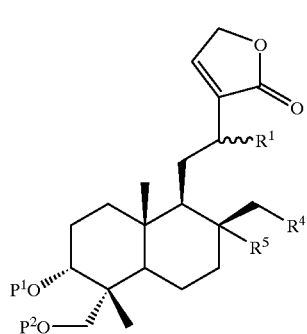

(X)

where all symbols are as defined earlier and if desired, (iv) deprotecting the compound of formula (X) by conventional methods to produce a compound of formula (XI),

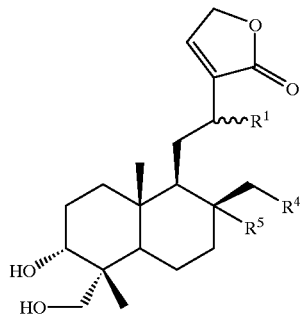

(XI)

where all symbols are as defined earlier.

The protection of a compound of formula (VII) may be carried out using trityl chloride, t-butyldimethylsilyl chloride, pivaloyl chloride, dimethylsulfoxide, acetone, 2,2-dimethoxy propane, trimethyl ortho acetate, benzaldehyde, p-methoxy benzaldehyde, acetophenone and the like. The reaction may be carried out in the presence of a suitable catalyst such as $SOCl_2$, $H_2SO_4$, $HClO_4$, pyridinium p-toluene sulphonate, pyridine, p-toluene sulfonic acid, dimethyl aminopyridine, and the like. The reaction may be carried out in the absence or presence of suitable solvent such as benzene, DMF, dimethylsulfoxide (DMSO), acetonitrile, dichloromethane (DCM), and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h.

The conversion of compound of formula (VIII) to compound of formula (IX) may be carried out using halogenating agents such as thionyl chloride, thionyl bromide, phosphonyl chloride, $PCl_5$, $PBr_3$ bromine trifluoride, N-bromosuccinimide-hydrogen fluoride (NBS-HF), cobalt (III) fluoride, lithium fluoride, potassium fluoride, sodium fluoride, cesium fluoride, potassium iodide, sodiumiodide, iodine, iodine cerium (IV) ammonium nitrate, or R-L where R is acetyl, propionyl, benzoyl, mesyl, tosyl, triflyl and the like and L is as defined above. The reaction may be carried out in the presence of solvents such as ether, dichloromethane, chloroform, DM, DMSO and the like; The reaction may be carried out in the range of −40° C. to 160° C. The duration of the reaction may range from 1 to 6 h.

The reaction of compound of formula (IX) with nucleophiles such as aniline, benzylamine, arylthio, piperazine, morpholine, imidazole aminotetrazole, triazole, esters of α-aminoacids, esters of β-amino acids, acetic acid, thioacetic acid, alkyl magnesium halide, aryl magnesium halide, methanol, ethanol propanol and the like may be carried out in the presence of solvents such as ether, DCM, DMF, and the like. The reaction may be carried out in the absence or presence of alumina. The reaction temperature may range from 80° C. to 100° C. and the reaction time may range from 1–10 h.

The deprotection of a compound of formula (X) to produce a compound of formula (XI) may be carried out using deprotecting agent such as acetic acid, hydrochloric acid, formic acid, trifluoroacetic acid and the like. The reaction may be carried in the presence of suitable solvent such as water, THF, dioxane, DCM, $CHCl_3$, methanol and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h.

The pharmaceutically acceptable salts are prepared by reacting the compounds of formula (I), formula (IX), formula (X), or formula (XI) wherever applicable with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, tromethamine, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds of formula (I), formula (IX), formula (X), and formula (XI) forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as brucine, cinchona alkaloids and their derivatives and the like.

Various polymorphs of compound of general formula (I), formula (IX), formula (X), and formula (XI), forming part of this invention may be prepared by crystallization of compound of formula (I), formula (IX), formula (X), or formula (XI), under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or slow cooling. The presence of polymorphs may be determined by solid probe NMR spectroscopy, IR spectroscopy, differential scanning calorimetry, powder X-ray data or such other techniques.

Pharmaceutically acceptable solvates of compounds of formula (I), formula (IX), formula (X), or formula (XI) forming part of this invention may be prepared by conventional methods such as dissolving the compounds of formula (I), formula (IX), formula (X) or formula (XI) in solvents such as water, methanol, ethanol etc., preferably water and recrystallizing by using different crystallization techniques.

The present invention also envisages pharmaceutical compositions containing compounds of the formulae (I), (IX), (X), (XI), their stereoisomers, their polymorphs, their pharmaceutically acceptable salts, or their pharmaceutically acceptable solvates or their mixtures in combination with the usual pharmaceutically employed carriers, solvents, diluents and other media normally employed in preparing such compositions.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 25%, preferably 1 to 15% by weight of active compound, the remainder of the composition being pharmaceutically acceptable carriers, diluents or solvents.

A compound of the formula (I), formula (IX), formula (X), and formula (XI) as defined above are clinically administered to mammals, including man, via either oral or parenteral routes. Administration by the oral route is preferred, being more convenient and avoiding the possible pain and irritation of injection. However, in circumstances where the patient cannot swallow the medication or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans.

The invention is explained in detail in the examples given below which are provided by way of illustration only and therefore should not be construed to limit the scope of the invention.

Preparation 1

Preparation of 14-acetyl-andrographolide & 14-acetyl-3,19-isopropylidene andrographolide.

Step 1

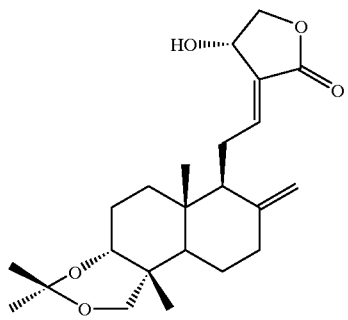

A mixture of andrographolide (15 g), 2,2-dimethoxypropane (20 ml) and catalytic amount of pyridinium p-toluene sulphonate (few crystals) in a solution of benzene/dimethyl suiphoxide (300 ml/40 ml) was refluxed for 30 min. After completion of the reaction (checked by TLC), the contents were cooled to room temperature and basified with excess triethylamine (10 ml) to quench the remaining catalyst. The mixture was diluted with benzene (200 ml) and washed with water (3×300 ml). The organic layer was dried over $Na_2SO_4$ and concentrated to obtain a yellow solid which on maceration with diethyl ether gave 3,19-isopropylidene andrographolide as a pale yellow product (15 g). m.p. 194.5° C.

$^1$H NMR ($CDCl_3$): δ7.0(t, 1H, H-12), 5.1(d, 1H, H-14), 4.95(s, 1H, H-17a), 4.65(s, 1H, H-17b), 4.5(m), 4.3(d, 1H), 4.0(d, 1H, H-19a), 3.5(dd, 1H, H-3), 3.2(d,1H, H-19b), 2.6(m), 1.45(s, 31H), 1.35(s, 3), 1.2(s, 3H), 1.0 (s, 3H).

Step 2

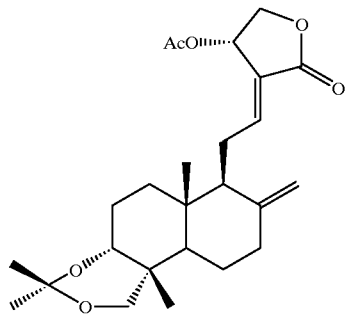

3,19-Isopropylidene andrographolide (15 g) obtained in step 1 was refluxed in distilled acetic anhydride (110 ml) for 45 min. After confirming the complete formation of the product (by TLC analysis), the contents were cooled to room temperature, diluted with water (500 ml) and extracted with dichloromethane (3×200 ml). The organic layer was separated and dried over $Na_2SO_4$ and concentrated to get a brown oily material. The crude material was purified by flash column chromatography (silica gel 230–400 mesh; 250 g, eluting system light petrol: ethyl acetate=85:15) to obtain pure 14-acetyl-3,19-isopropylidene andrographolide (13 g).

$^1$H NMR (CDCl$_3$): δ7.0(t, 1H , H-12), 5.9(d, 1H, H-14), 4.90(s, 1H, H-17a), 4.60(m), 4.3 (dd, 1H), 4.0(d, 1H, H-19a), 3.5(dd, 1H, H-3), 3.2(d, 1H, H-19b), 2.4(m), 2.1(s, 3H), 1.4(s, 3H), 1.3 (s, 3H), 1.2(s, 3H), 0.9(s, 3H).

Step 3

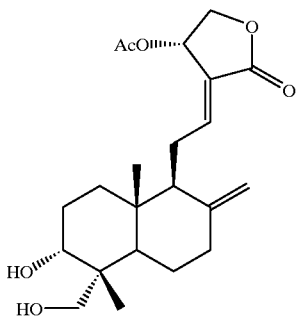

14-Acetyl-3,19-isopropylidene andrographolide (13 g) obtained in step 2 was treated with 75 ml of aq. acetic acid (aceticacid:water=7:3) and the contents stirred for 10 min at room temperature till a clear solution was obtained. The contents were diluted with dichloromethane (500 ml) and washed with water (3×300 ml) followed by aq sodium bicarbonate (2×300 ml). The organic layer was separated, dried over $Na_2SO_4$ and concentrated to get crude 14-acetyl andrographolide as a pale yellow coloured solid which was purified by crystallising in ethyl acetate/light petrol (11.2 g). m.p.169° C.

$^1$H NMR (CDCl$_3$): δ7.0(t, 1H, H-12), 5.9(d, 1H, H-14), 4.90(s, 1H, H-17a), 4.60(m), 4.2(dd), 3.9(d, 1H, H-19a), 3.5(t, 1H, H-3), 3.4(d, 1H, H-19), 2.1(s, 3H), 1.2(s, 3H), 0.8(s, 3H).

Preparation 2

Preparation of 14-acetyl-3,19-O-(1-phenyl ethylidene)andrographolide

Step 1

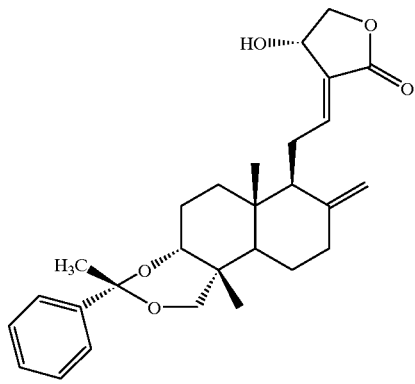

A mixture of andrographolide (5 g), 1,1-dimethoxy ethyl benzene (8 g) and catalytic amount of pyridinium p-toluene sulphonate (few crystals) in a solution of benzene/dimethyl sulphoxide (100 ml/10 ml) was refluxed for 2 h. After completion of the reaction (checked by TLC), the contents were cooled to room temperature and basified with excess triethylamine to quench the remaining catalyst. The mixture was diluted with benzene (75 ml) and washed with water (3×100 ml). The organic layer was dried over $Na_2SO_4$, concentrated and the crude material was purified by flash column chromatography (120 g of silica gel 230–400 mesh, light petrol:ethyl acetate=80:20) followed by recrystallisation with hexane/dichloromethane to obtain 3,19-O-(1-phenyl ethylidene)andrographolide (2.7 g) as a colourless product. m.p. 201.3° C.

$^1$H NMR (CDCl$_3$): δ7.6–7.2(m), 6.95(t, 1H, H-12), 5.0(d, 1H, H-14), 4.85(s, 1H, H-17a), 4.50(s, 1H, H-17b), 4.4(m), 4.2(dd, 1H), 4.1(d, 1H, H-19a), 3.6(dd, 1H, H-3), 3.3(d, 1H, H-19b), 2.4(m), 1.5(s, 3H), 1.4(s, 3H), 0.4(s, 3H).

Step 2

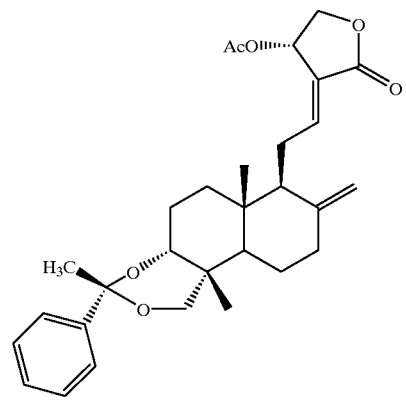

3,19-O-(1-Phenylethylidene)androgapholide (2 g) obtained in step 1 was refluxed in distilled acetic anhydride (15 ml) for 30 min. After confirming the complete formation of the product (by TLC analysis), the contents were cooled to room temperature and diluted with water (100 ml) and extracted with dichloromethane (3×50 ml). The organic layer was separated, dried over Na$_2$SO$_4$, concentrated to get a brown oily material. The crude material was purified by flash column chromatography (silica gel 230–400, light petrol:ethylacetate=85:15) to obtain 1.8 g of the pure 14-acetyl-3,19-O-(1-phenylethylidene)androgapholide.

$^1$H NMR (CDCl$_3$): δ7.6–7.2(m), 7.0(t, 1H, H-12), 5.9(d, 1H, H-14), 4.90(s, 1H, H-17a), 4.50(m) 4.30(dd), 4.1(d, 1H, H-19a), 3.6(dd, 1H, H-3), 3.3(d, 1H, H-19b), 2.4(m), 2.1(s, 3H), 1.55(s, 3H), 1.45(s, 3H), 0.5(s, 3H).

Preparation 3

Preparation of 14-acetyl-3,19-benzylidene androgapholide

Step 1

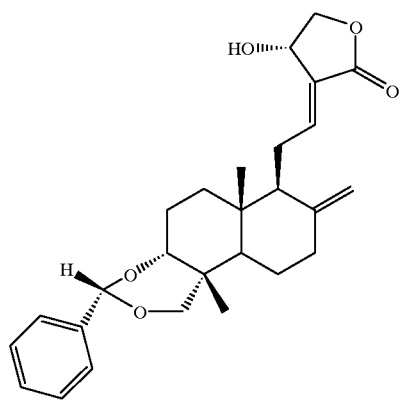

A mixture of androgapholide (5 g), freshly distilled benzaldehyde (20 ml) and a catalytic amount of zinc chloride was stirred at room temperature for 1 h. After completion of the reaction (checked by TLC), the contents were diluted with dichloromethane and washed with aqueous sodium bisulfite solution and water. The organic layer was dried over Na$_2$SO$_4$ and concentrated to get 5.5 g of crude 3,19-benzylidene androgapholide. m.p. 142–143° C.

$^1$H NMR (CDCl$_3$: δ7.6–7.3(m), 7.0(t, 1H, H-12), 5.8(s, 1H), 5.0(d, 1H, H-14), 4.85(s, 1H, H-17a), 4.6(s, 1H, H-17b), 4.4(m), 4.3(m), 3.7–3.5(m), 2.7–2.2(m), 1.5(s, 3H), 0.9(s, 3H).

Step 2

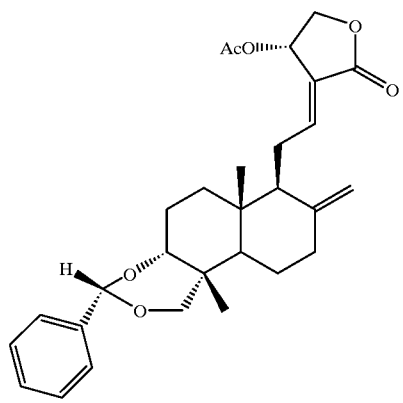

3,19-Benzylidene androgapholide (5 g) obtained in step 1 was refluxed in distilled acetic anhydride (15 ml) for 10 min. After confirming the complete formation of the product (by TLC analysis), the contents were cooled to room temperature and diluted with water (100 ml) and extracted with dichloromethane (3×50 ml). The organic layer was separated and dried over Na$_2$SO$_4$, concentrated to get a brown oily material. The crude material was purified by flash column chromatography (silica gel 230–400 mesh, eluting with light petrol:ethylacetate 90:10) to obtain 1.7 g of the pure 14-acetyl-3,19-benzylidene androgapholide.

$^1$H NMR (CDCl$_3$): δ7.6–7.2(m), 7.0(t, 1H, H-12), 5.9(d, 1H, H-14), 5.8(s, 1H), 4.95(s, 1H, H-17a), 4.5(m), 4.3(d, 1H, H-19a), 3.65(dd, 1H, H-3), 3.6(d, 1H, H-19b), 2.4(m), 2.1(s, 3H), 1.5(s, 3H), 0.9(s, 3H).

Preparation 4

Preparation of 14-acetyl-8,17-epoxy androgapholide

Step 1

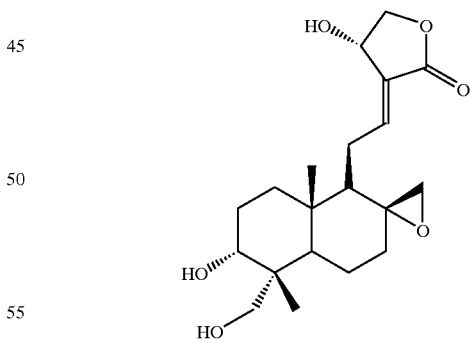

Androgapholide (500 mg) was dissolved in chloroform (50 ml with few drops of methanol) and to it was added meta chloro perbenzoic acid (980 mg) and the mixture stirred for 4 h. The reaction was monitored by TLC. After completion of the reaction, the reaction mixture was concentrated and chromatographed over a column of silica gel (60–120 mesh; 50 g) with chloroform:acetone (75:25) as solvent system to obtain 8,17-epoxy androgapholide as a colourless product (300 mg, 57%). m.p. 170° C.

¹H NMR (CDCl₃+DMSO): δ6.85(1H, t, J=10 Hz, C-12 H), 5.00 (1H, d, J=5.8 Hz, C-14 H), 4.40–4.00(m), 3.40(1H, t, C-3H), 3.25(1H, d, C-19 Hb), 2.75(2H, dd, J=12.4 Hz, C-17).

Step 2

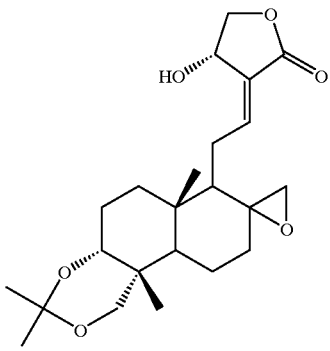

8,17-Epoxy andrographolide (2 g) was taken in a mixture of 2,2-dimethoxy propane (15 ml) and DMSO (2 ml). The mixture was heated to about 45° C. until a clear solution was obtained. Then the solution was cooled to room temperature, a catalytic amount of pyridinium p-toluene sulphonate (PPTS) was added and the contents were stirred for one hour at room temperature. After the reaction was complete, the reaction mixture was quenched with triethylamine (2 ml), poured into water (100 ml), extracted with DCM (3×200 ml). The organic layer was dried over sodium sulfate and concentrated to dryness. The residue was chromatographed over a column of silica gel with chloroform:acetone (95:5) as the eluent to obtain 8,17-epoxy-3,19-isopropylidene andrographolide (2 g, 90%). m.p. 179° C.

¹H NMR (CDCl₃): δ6.8(1H, m, C-12), 5.0(1H, d, C-14), 4.4–4.0(m), 3.95(1H, d, C-19Ha), 3.55 (1H, dd, C-33), 3.2(1H, d, C-19 Hb), 2.8(2H, dd, J=12, 4 Hz, C-17 H), 1.4 (3H, s), 1.35(3H, s).

Step 3

8,17-Epoxy-3,19-isopropylidene andrographolide (15 g) obtained in step 2 was refluxed in distilled acetic anhydride (110 ml) for 45 min. After confirming the complete formation of the product (by TLC analysis), the contents were cooled to room temperature and diluted with water (500 ml) and extracted with dichloromethane (3×200 ml). The organic layer was separated and dried over Na₂SO₄ and concentrated to get a brown oily material. The crude material was purified by flash column chromatography (silica gel 230–400 mesh; 250 g, eluting system light petrol:ethyl acetate=85:15) to obtain pure 14-acetyl-8,17-epoxy-3,19-isopropylidene andrographolide (13 g).

Step 4

14-Acetyl-8,17-epoxy-3,19-isopropylidene andrographolide (13 g) obtained in step 3 was treated with 75 ml of aq acetic acid (acetic acid:water 7:3) and the contents stirred for 10 min at room temperature till a clear solution was obtained. The contents were diluted with dichloromethane (500 ml) and washed with water (3×300 ml) followed by aq sodium bicarbonate (2×300 ml ). The organic layer was separated, dried over Na₂SO₄ and concentrated to get crude 14-acetyl-8,17-epoxy andrographolide as a pale yellow coloured solid which was purified by crystalising in ethyl acetate/light petrol (11.2 g). m.p. 117° C.

¹H NMR (CDCl₃): δ7.1(t, H, -12), 5.9(d, H, H-14), 4.5(m), 4.25(d), 4.15(d, 1H, H-19a), 3.5(dd, 1H, H-3), 3.35(d, 1H, H-19b), 2.6(d, 1H, H-17a), 2.5(d, 1H, H-17b), 2.1(s, 3H), 1.2(s, 3H), 0.8(s, 3H).

Preparation 5

Preparation of 3,14,19-triacetyl-8,17-epoxy andrographolide

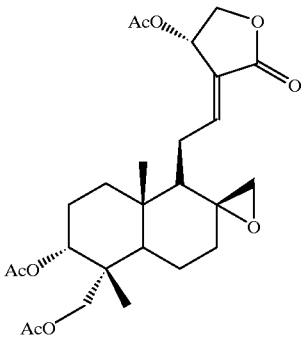

8,17-Epoxy andrographolide (100 mg) obtained in preparation 4 above was taken in 2 ml of acetic anhydride and refluxed for 5 min. The reaction was monitored by TLC. After completion of the reaction, the reaction mixture was diluted with solvent ether, washed with water, dried over Na₂SO₄ and concentrated. The residue obtained was chromatographed over a column of silica gel (60–120 mesh) with light petrol:ethyl acetate (65:35) as the solvent system to afford the title compound as a colourless solid (90 mg, 67%). m.p. 195° C.

¹H NMR: δ7.09(1H, t, J=10 Hz, C-12 H), 5.88(1H, d, J=5.8 Hz, C-14 H), 4.55(1H, C-3H), 4.5(1H, C-15Ha), 4.29(1H, C-19Ha), 4.21(1H, C-15 Hb), 4.16(1H, C-19Hb), 2.6(2H, dd, J=12.4 Hz, C-17H), 2.11(3H, S, OAc), 2.05(6H, s, OAc).

EXAMPLE 1

3,19-Diacetyl-12-(N-benzylamino)-14-deoxy andrographolide

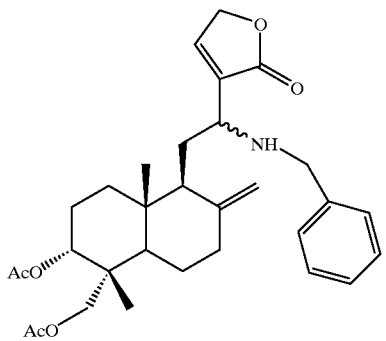

To a suspension of 3,14,19-triacetyl andrographolide (5 g, 10.5 mmols) (Ref: *Journal of Chemical Society,* 1952, p-1697–1700) in diethyl ether (200 ml), benzyl amine (3.37 g, 31.5 mmols) was added dropwise and the contents were stirred at room temperature for 30 min. The reaction was monitored by TLC. After completion of the reaction, the reaction mixture was diluted with diethyl ether, washed thoroughly with water and dried over Na₂SO₄. The crude solid obtained after removal of the solvent was purified by crystallization in ethyl acetate and hexane solvent mixture to get the title compound as a colourless crystalline solid (3.5 g). m.p. 122.7° C., m/z 523.

$^1$H NMR (CDCl$_3$): δ7.3(br s, 6H), 4.85(br s, 3H), 4.65(s, 1H, H-17b), 4.55 (dd), 4.3(d, 1H, H-19a), 4.1(d, 1H, H-19b), 3.8–3.4(m), 2.0(s, 6H), 1.0(s, 3H), 0.7(s, 3H).

EXAMPLE 2
14-Deoxy-12-(O-methylphenylglycino)-3,19-O-(1-phenylethylidene) androgrpaholide

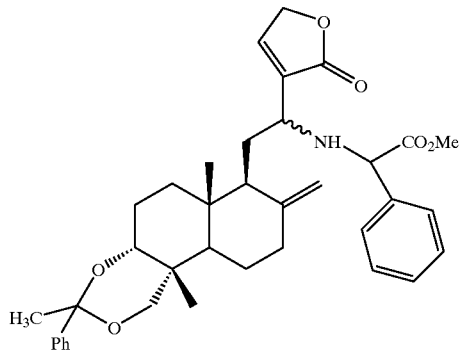

To a suspension of 14-acetyl-3,19-O-(1-phenylethylidene)andrographolide (2.2 g, 4.45 mmols) in diethyl ether (100 ml), methyl ester of phenyl glycine (1.84 g, 11.1 mmols) was added dropwise and the contents were stirred at room temperature for 5 h. The reaction was monitored by TLC. After completion of the reaction, the reaction mixture was diluted with diethyl ether, washed thoroughly with water, dried over Na$_2$SO$_4$ and concentrated. The residue was purified by flash chromatography over a column of silicagel (230–400 mesh) with light petrol:ethyl acetate (82:18) as solvent system to obtain the title compound as a colourless solid (1.6 g ). m.p. 91° C., m/z 599.

$^1$H NMR(CDCl$_3$): δ7.45–7.2(m), 7.1(s), 4.8(s, 2H), 4.65 (s, 1H, H-17a), 4.35(s, 1H, H-17b), 4.0(d, 1H, H-19a), 3.6(s, 3H), 3.45(dd), 3.2(dd, 1H), 1.45(s, 3H), 1.2(s, 3H), 0.3(s, 3H).

Examples 3–26 have been prepared by using similar procedures described in Examples 1 & 2.

| Example No. | Structure | Mol. Formula/ Mol. wt & melting point | Spectral data |
|---|---|---|---|
| 3 | 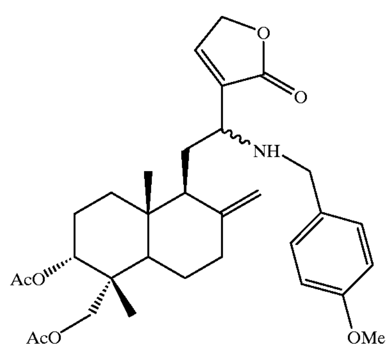 | C$_{32}$H$_{43}$O$_7$N<br>m/z 553<br>mp 113° C. | $^1$H NMR(CDCl$_3$):<br>δ 7.2(d, 2H), 6.8(d, 2H), 4.8(br s, 3H), 4.65(s, 1H, H-17b), 4.5(dd), 4.3(d, 1H, H-19a), 4.1(d, 1H, H-19b), 3.8(s, 3H), 3.7–3.4(m), 2.0(s, 6H), 1.0(s, 3H), 0.7(s, 3H). |
| 4 | 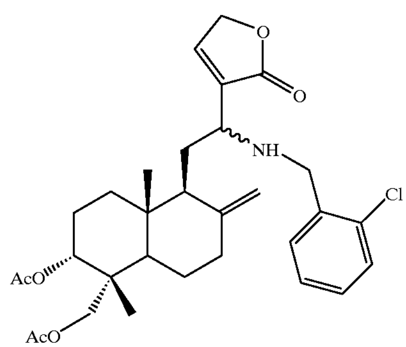 | C$_{31}$H$_{40}$O$_6$NCl<br>m/z 557<br>mp: 114.6° C. | $^1$H NMR(CDCl$_3$):<br>δ 7.4–7.1(m), (s, 1H), 4.85(s, 1H, H-17a), 4.80(s, 2H, H-15), 4.7(s, 1H, H-17b), 4.6(dd), 4.3(d, 1H, H-19a), 4.1(d, 1H, H-19b), 3.75(m), 3.5(m), 2.1(s, 6H), 1.0(s, 3H), 0.7(s, 3H). |

-continued

| Example No. | Structure | Mol. Formula/ Mol. wt & melting point | Spectral data |
|---|---|---|---|
| 5 | 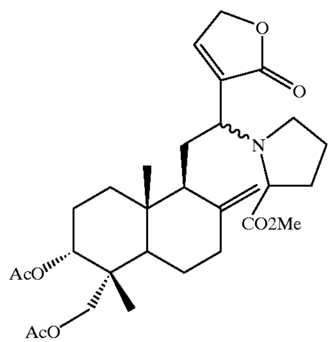 | C$_{30}$H$_{43}$O$_8$N m/z: 545 mp: 61–62° C. | $^1$H NMR(CDCl$_3$): δ 7.5(s, 1H), 4.9(s, 1H, H-17a), 4.85(d, 2H, H-15), 4.7(s, 1H, H-17b), 4.5(m), 4.35(d, 1H, H19a), 4.1(d, 1H, H-19b), 3.7(s, 3H), 3.4(m), 3.3(m), 2.0(s, 6H), 1.0(s, 3H), 0.7(s, 3H). |
| 6 | 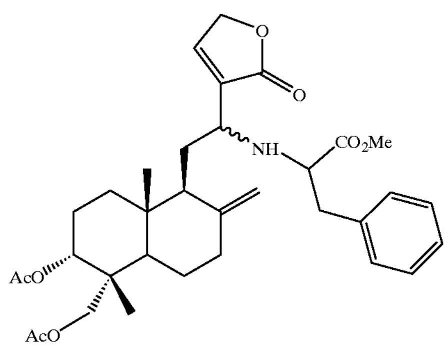 | C$_{34}$H$_{45}$O$_8$N m/z 595 mp: 59–61° C. | $^1$H NMR(CDCl$_3$): δ 7.4–7.1(m), 4.85(s, 1H, H-17a), 4.8(s, 2H, H-5), 4.55(m) 4.5(s, 1H, H-17b), 4.3(d, 1H, H19a), 4.1(d, 1H, H-19b), 3.6(s, 3H), 3.5(m), 2.8(m), 2.0(s, 6H), 1.0(s, 3H), 0.7(s, 3H). |
| 7 | 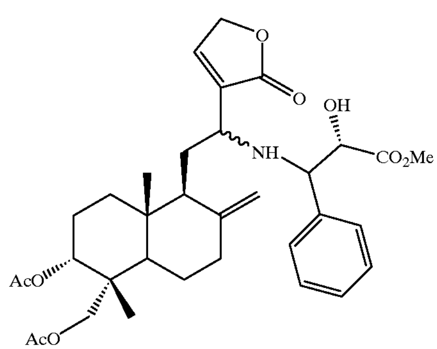 | C$_{34}$H$_{45}$O$_9$N m/z 611 mp: 71.7° C. | $^1$H NMR(CDCl$_3$): δ 7.3(m), 7.0(s, 1H), 6.8(s, 1H), 4.9(s, 1H, H-17a), 4.8(s, 2H, H-15), 4.6–4.4(m), 4.4–4.0(m), 3.75(s, 3H), 3.65(s, 3H), 3.5(m), 3.3(m), 2.0(s, 3H), 1.0(s, 3H), 0.7(s, 3H), 0.65(s, 3H). |
| 8 | 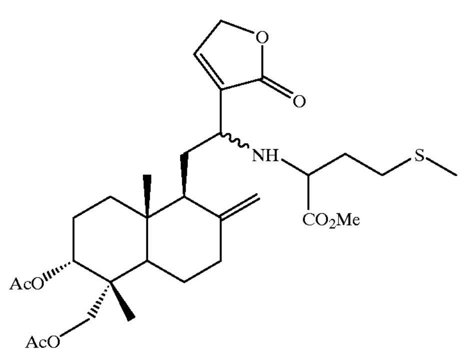 | C$_{30}$H$_{45}$O$_8$SN m/z 579 waxy solid | $^1$H NMR(CDCl$_3$): δ 7.1(s, 1H), 4.9(s, 1H, H-17a), 4.8(s, 2H, H-15), 4.65(s, 1H, H-17b), 4.5(dd), 4.3(d, 1H, H-19a), 4.05(d, 1H, H-19b), 3.6(s, 3H, OMe), 3.5(m), 3.3(t), 2.6(t), 2.1(s, 3H), 2.0(s, 3H), 1.0(s, 3H), 0.7(s, 3H). |

-continued

| Example No. | Structure | Mol. Formula/ Mol. wt & melting point | Spectral data |
|---|---|---|---|
| 9 | 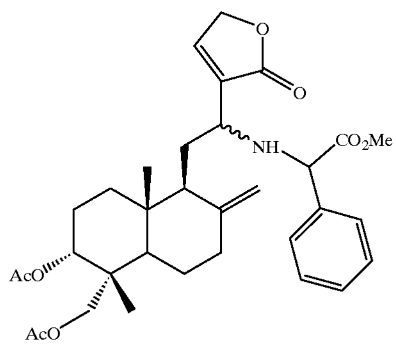 | $C_{33}H_{48}O_8N$<br>m/z 581<br>mp: 63–65° C. | $^1$H NMR(CDCl$_3$):<br>δ 7.3(s, 5H), 7.1(s, 1H), 4.85(s, 2H), 4.75(s, 1H, H-17a), 4.5(m), 4.42(s, 1H, H-17b), 4.3(d, 1H, H-19a), 4.05(d, 1H, H-19b), 3.6(s, 3H, OMe), 3.4(dd), 2.0(s, 6H), 1.0(s, 3H), 0.7(s, 3H). |
| 10 | 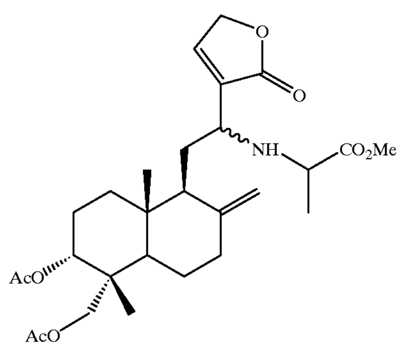 | $C_{28}H_{41}O_8N$<br>m/z 519 | $^1$H NMR(CDCl$_3$):<br>δ 7.2(s, 1H), 4.9(s, 1H), 4.85 (s, 2H), 4.7(s, 1H), 4.6–4.5(dd), 4.35(d, 1H), 4.1(d, 1H), 3.7(s, 3H), 3.3(m), 2.0(s, 6H), 1.0(s, 3H), 0.7(s, 3H). |
| 11 | 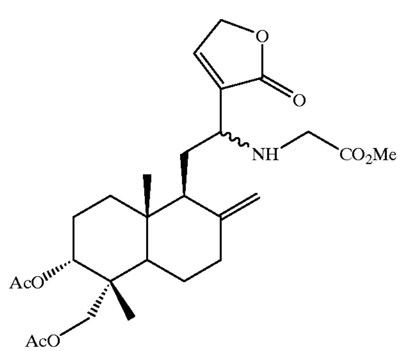 | $C_{27}H_{39}O_8N$<br>m/z 505<br>waxy solid | $^1$H NMR(CDCl$_3$):<br>δ 7.2(d, 2H), 4.9(s, 1H), 4.85 (s, 2H), 4.7(s, 1H), 4.6–4.5(dd), 4.3(d, 1H), 4.1(d, 1H), 3.7(s, 3H), 3.5(m, 1H), 3.3(d, 2H), 2.0(s, 6H), 1.0(s, 3H)), 0.7(s, 3H) |
| 12 | 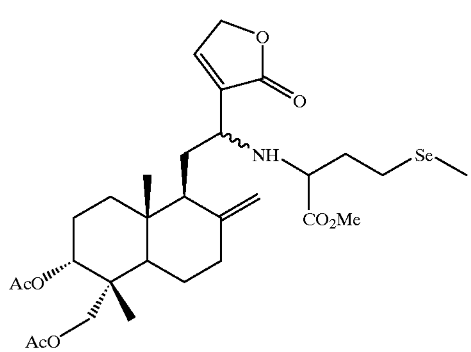 | $C_{30}H_{45}O_8NSe$<br>m/z 626<br>waxy solid | $^1$H NMR(CDCl$_3$):<br>δ 7.3(s, 1H), 4.9(s, 1H), 4.8(s, 2H), 4.65(s, 1H), 4.6–4.4(dd), 4.3(d, 1H, H-19a), 4.1(d, 1H, H-19b), 3.6(s, 3H), 3.5(dd), 3.3(t), 2.6(t), 2.15(s, 3H), 2.0 (s, H), 1.0(s, 3H), 0.7(s, 3H). |

-continued

| Example No. | Structure | Mol. Formula/ Mol. wt & melting point | Spectral data |
|---|---|---|---|
| 13 | 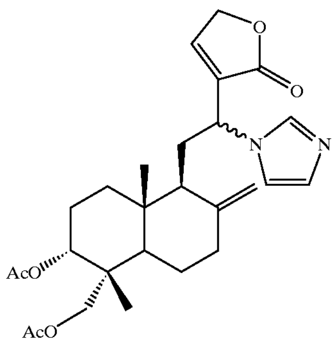 | $C_{27}H_{36}O_6N_2$<br>m/z 484<br>mp. 95° C. | $^1$H NMR(CDCl$_3$):<br>δ 7.5(s, 1H), 7.2(d), 7.0(d), 5.4(s, 2H, H-15), 5.2(d), 5.0 (s, 1H, H-17a), 4.8(s, 1H, H-17b), 4.5(dd), 4.4 (d, 1H, H-19a), 4.1(d, 1H, H-19b), 2.4(d), 2(s, 6H), 1.0(s, 3H), 0.7(s, 3H). |
| 14 | 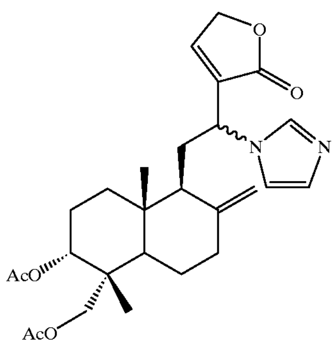 | $C_{27}H_{36}O_6N_2$<br>m/z 484<br>mp. 105° C. | $^1$H NMR(CDCl$_3$):<br>δ 7.7(s), 7.3(s), 7.1(s), 5.1 (dd), 5.0(s, 1H, H-17a), 4.8 (s, 2H, H-15), 4.6(s, 1H, H-17b), 4.4(d, 1H, H-19a), 4.1(d, 1H, H-19b), 2.6(t), 2.4(d), 2.0(s, 6H), 1.0(s, 3H), 0.7(s, 3H). |
| 15 | 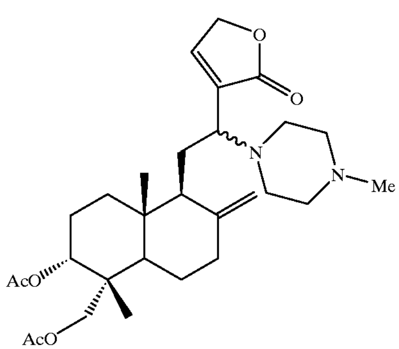 | $C_{29}H_{44}O_6N_2$<br>m/z 516<br>mp: 78.5° C. | $^1$H NMR(CDCl$_3$):<br>δ 7.2(s, 1H), 4.9(s, 1H, H-17a), 4.85(s, 2H, H-15), 4.7(s, 1H, H-17b), 4.35(d, 1H, H-19a), 4.1(d, 1H, H-19b), 3.6(d), 2.3(s, 3H), 2.0(s, 6H), 1.0(s, 3H), 0.7(s, 3H). |
| 16 | 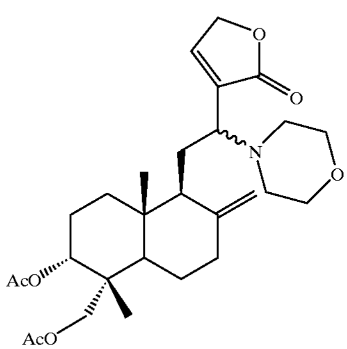 | $C_{28}H_{44}O_7N$<br>m/z 503<br>mp: 204° C. | $^1$H NMR(CDCl$_3$):<br>δ 7.3(s, 1H), 4.9(br s, 3H), 4.7(s, 1H, H-17b), 4.5(m), 4.35(d, 1H, H-19a), 4.1 (d, 1H, H-19b), 3.7(m), 2.5(m), 2.0(s, 6H), 1.0 (s, 3H), 0.7(s, 3H). |

-continued

| Example No. | Structure | Mol. Formula/ Mol. wt & melting point | Spectral data |
|---|---|---|---|
| 17 | 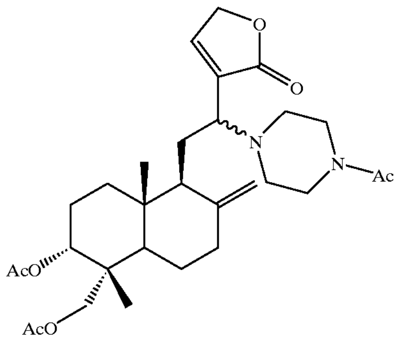 | $C_{30}H_{44}O_7N_2$<br>m/z 544<br>mp: 81° C. | $^1$H NMR(CDCl$_3$):<br>δ 7.2(s, 1H), 4.9(s, 3H, H-15 & H-17a), 4.75(s, 1H, H-17b), 4.6(m), 4.4(d, 1H, H-19a), 4.1 (d, 1H, H-19b), 3.3–3.7 (m), 2.1(s, 6H), 1.0(s, 3H), 0.7(s, 3H). |
| 18 | 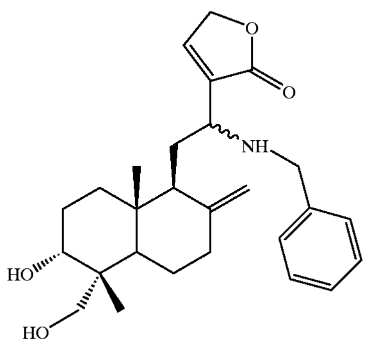 | $C_{27}H_{37}O_4N$<br>m/z 439<br>mp: 192° C. | $^1$H NMR(CDCl$_3$):<br>δ 7.3(s), 7.18(s), 4.8(br s, 2H), 4.6(s, 1H), 4.1(d, 1H, H-19a), 3.7(d), 3.5(m), 3.4(t), 3.25(d, 1H, H-19b), 1.2(s, 3H), 0.6(s, 3H). |
| 19 | 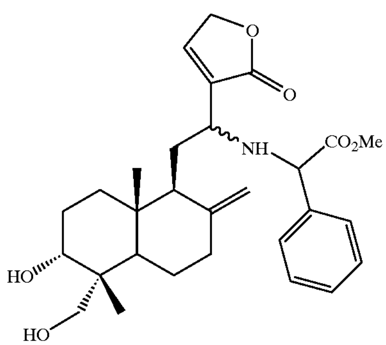 | $C_{29}H_{36}O_6N$<br>m/z 497<br>mp: 68° C. | $^1$H NMR(CDCl$_3$):<br>δ 7.4–7.2(m), 7.1(s), 4.85(s, 2H, H-15), 4.7(s, 1H, H-17a), 4.45(s, 1H, H-17b), 4.32–4.10(m), 3.7(s, 3H), 3.45–3.2(m), 1.2(s, 3H), 0.6(s, 3H). |
| 20 | 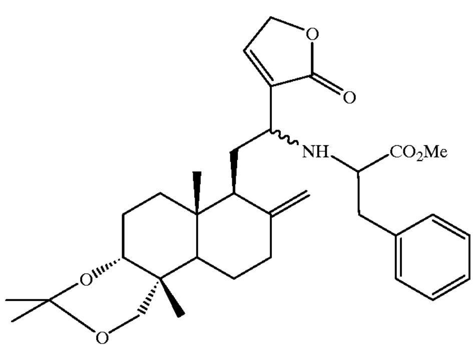 | $C_{33}H_{45}O_6N$<br>m/z 551<br>mp: 57° C. | $^1$H NMR(CDCl$_3$):<br>δ 7.35–7.05(m), 4.8(s, 1H, H-17a), 4.75(s, 2H, H-15), 4.45(s, 1H, H-17b), 3.8(d, 1H, H-19a), 3.6(s, 3H), 3.5–3.3(m), 3.18(d, 1H, H-19b), 2.9(m), 1.4(s, 3H), 1.38(s, 3H), 1.2(s, 3H), 0.8(s, 3H). |

-continued

| Example No. | Structure | Mol. Formula/ Mol. wt & melting point | Spectral data |
|---|---|---|---|
| 21 | 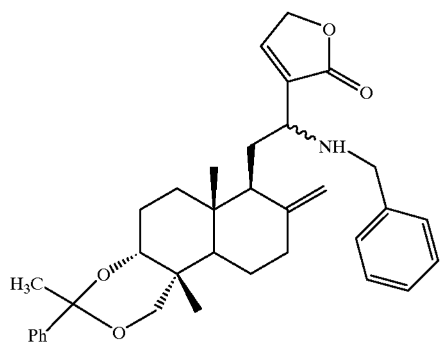 | $C_{35}H_{43}O_4N$<br>m/z 541<br>mp: 149.6° C. | $^1$H NMR(CDCl$_3$):<br>δ 7.42(d), 7.2(m), 7.1(s),<br>4.8(br s, 3H), 4.5(s, 1H),<br>4.0(d, 1H), 3.65(d), 3.45(dd),<br>3.28(d), 2.3(d), 1.45(s, 3H),<br>1.38(s, 3H), 0.4(s, 3H). |
| 22 | 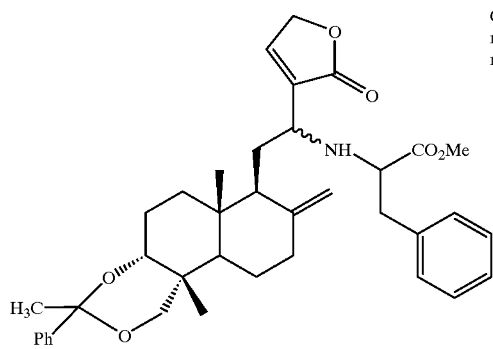 | $C_{38}H_{47}O_6N$<br>m/z 613<br>mp: 171.6–171.9° C. | $^1$H NMR(CDCl$_3$):<br>δ 7.45–7.05(m), 4.7(m, 3H),<br>4.4(s, 1H), 4.0(d, 1H), 3.6(s, 3H), 3.45–3.25(m), 2.85(m),<br>1.5(s, 3H), 1.4(s, 3H), 0.4(s, 3H) |
| 23 | 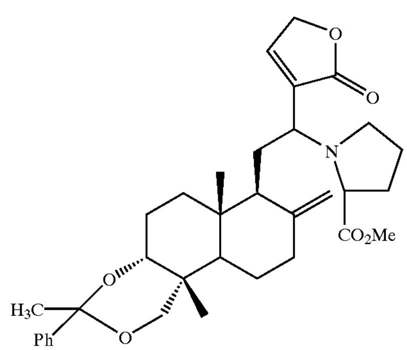 | $C_{34}H_{45}O_6N$<br>m/z 563<br>mp: 141–143° C. | $^1$H NMR(CDCl$_3$):<br>δ 7.6–7.2(m), 4.8(s, 2H),<br>4.7(d, 2H), 4.0(d, 1H), 3.6(s, 3H), 1.5(s, 3H), 1.4(s, 3H),<br>0.4(s, 3H). |
| 24 | 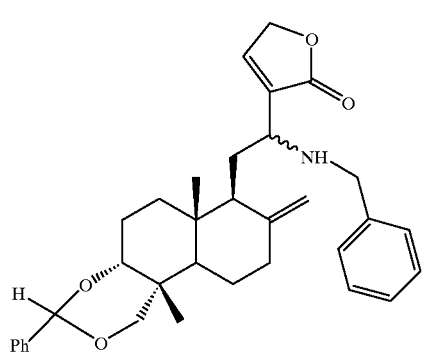 | $C_{34}H_{41}O_4N$<br>m/z 527<br>mp: 172–173° C. | $^1$H NMR(CDCl$_3$):<br>δ 7.45(m), 7.4–7.2(m), 5.78<br>(s, 1H), 4.82(s, 1H, H-17a),<br>4.8(s, 2H, H-15), 4.6(s, 1H, H-17b), 4.25(d, 1H, H-19a),<br>3.75(d, 1H, H-19b), 3.6–<br>3.45(m), 2.4(m), 1.45(s, 3H)<br>0.8(s, 3H) |

| Example No. | Structure | Mol. Formula/ Mol. wt & melting point | Spectral data |
|---|---|---|---|
| 25 | 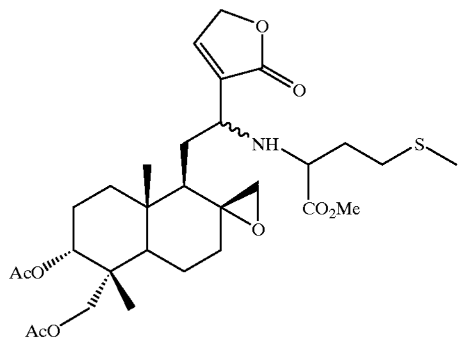 | $C_{30}H_{45}O_9NS$<br>m/z 595<br>waxy solid | $^1$H NMR(CDCl$_3$):<br>δ 7.3(s, 1H), 4.8(d, 2H), 4.6 (dd), 4.3(d, 1H, 19Ha), 4.1(d, 1H, 19Hb), 3.8(s, 3H, OMe), 3.5(t, 1H), 3.3(t, 1H), 2.8–2.4(m), 2.1(s, 3H), 2.0(s, 3H), 1.0(s, 3H), 0.8(s, 3H).<br>Mass: 596, 548, 536, 373 295, 258, 197, 164, 147, 104. |
| 26 | 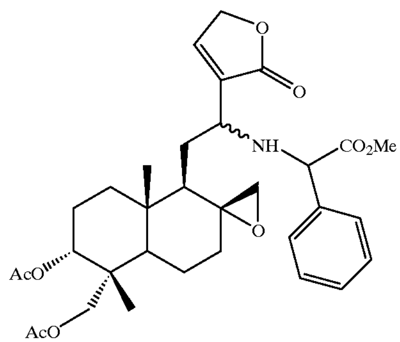 | $C_{33}H_{44}O_9N$<br>m/z 597<br>mp: 65° C. | $^1$H NMR(CDCl$_3$):<br>δ 7.4(br s, 6H), 4.8(s, 2H), 4.45(t), 4.3–4.0(m), 3.7(s, 3H, OMe), 3.2(dd), 2.65(d, 1H, 17Hb), 2.52(d, 1H, 17-Ha), 2.0(s, 6H), 1.0(s, 3H), 0.7(s, 3H) |

EXAMPLE 27

3,19-Diacetyl-14-deoxy-12-(N-1,2,4-triazolyl) androaapholide

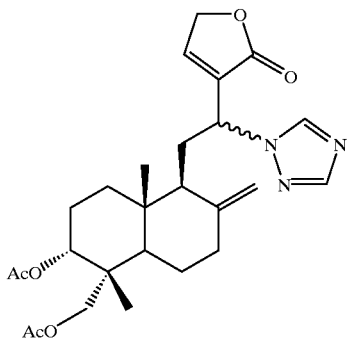

A mixture of 3,14,19-triacetyl andrographolide (500 mg, 1.05 mmol) (Ref: *Journal of Chemical Society*, 1952, p-1697–1700) and 1,2,4 triazole (220 mg, 3.18 mmol) in DMF(10 ml) were heated to 100° C. and the heating continued for 1 h. The reaction was monitored by TLC. After completion of the reaction, the reaction mixture was poured into water, extracted with diethyl ether and dried over Na$_2$SO$_4$. The residue obtained after removal of the solvent was flash chromatographed over a column of silica gel (230–400 mesh) with chloroform:methanol (99.5:0.5) as the eluting system to get the title compound as a colourless solid (200 mg). m.p. 129° C., m/z 485.

$^1$H NMR (CDCl$_3$): δ8.2(s), 7.9(s), 7.6(s), 5.3(dd), 4.9(m, 3H), 4.5(s, 2H) 4.4(d, 1H, H-19a), 4.1(d, 1H, H-19b), 2.6(t), 2.4(m), 2.0(s, 6H), 1.0(s, 3H), 0.7(s, 3H).

EXAMPLE 28

1-(2,3-Dimethylanilino)-14-deoxy andrographolide

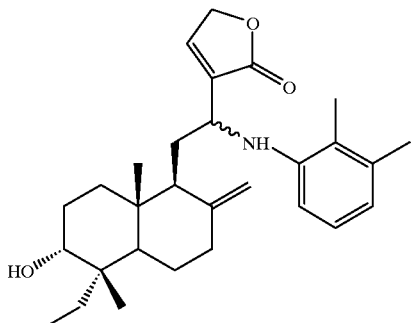

A mixture of 2,3-dimethyl aniline (4.93 ml, 40.4 mmol) and alumina in solvent ether was stirred for 10 min. 14-Acetyl andrographolide (4 g, 10.2 mmol) was added to the above slurry and the contents were stirred overnight. After completion of the reaction (monitored by TLC), the reaction mixture was diluted with methanol and filtered through Celite. The residue obtained after removal of the solvent was chromatographed over a column of silica gel (230–400 mesh) with light petrol:ethyl acetate (8:2- - -7:3- - -6.5:3.5). The product obtained is macerated with ethyl acetate to get the title compound as a colourless solid (2.5 g), m/z 453.

¹H NMR(CDCl₃)(CDCl₃): δ7.1(s, 1H), 6.9(t), 6.6(d), 6.25(d), 4.95(s, 1H, H-17a), 4.8(s, 1H, H-17b), 4.75(s, 2H, H-15), 4.3(t), 4.2(d, 1H, H-19a), 3.5(t), 3.3(d, 1H, H-19b), 2.3(s, 3H), 2.0(s, 3H), 1.2(s, 3H), 0.7(s, 3H).

Examples 29–41 have been prepared by using similar procedures described in Examples 27 & 28.

| Example No. | Structure | Mol. formula/ Mol. wt & melting point | Spectral data |
|---|---|---|---|
| 29 | 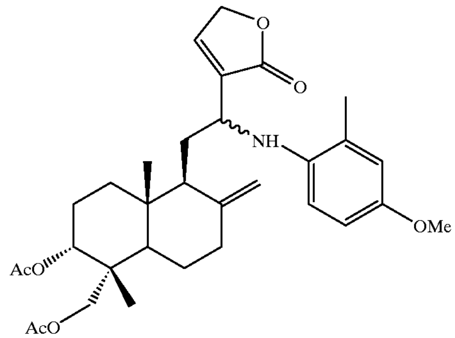 | C₃₂H₄₃O₇N m/z 553 mp 82.3° C. | ¹H NMR(CDCl₃): δ 7.15(s, 1H), 6.7–6.5(m), 6.35(d), 5.0(s, 1H, H-17a), 4.8(s, 1H, H-17b), 4.75(d, 2H, H-15), 4.65–4.5(m), 4.35(d, 1H, H-19a) 4.2(t), 4.1(d, 1H, H-19b), 3.7(s, 3H, OMe), 2.1(s, 3H), 2.0(s, 3H), 1.0(s, 3H), 0.7(s, 3H), |
| 30 | 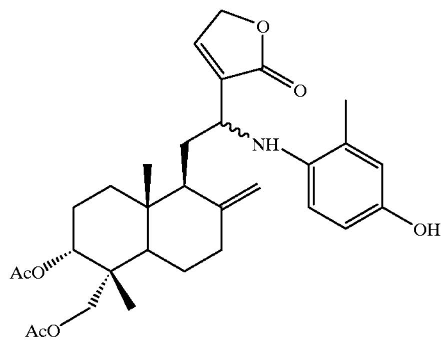 | C₃₁H₄₁O₇N m/z 539 mp 114.8° C. | ¹H NMR(CDCl₃): δ 7.15(s, 1H), 6.7–6.5(m), 6.3 (d), 5.0(s, 1H, H-17a), 4.8(br s, 3H), 4.7–4.5(m), 4.4(d, 1H, H-19a), 4.2(t), 4.1(d, 1H, H-19b), 2.1(s, 3H), 2.0(s, 3H), 1.0(s, 3H), 0.7(s, 3H). |
| 31 | 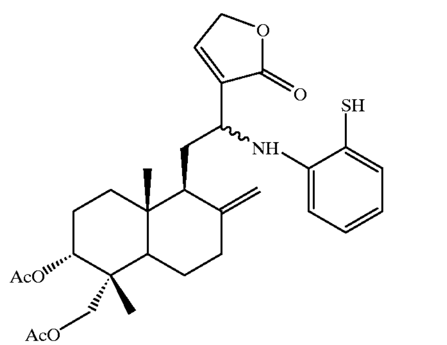 | C₃₀H₃₉O₆NS m/z 541 mp 90.1° C. | ¹H NMR(CDCl₃): δ 7.4–7.0(m), 6.8–6.5(m), 4.9–4.2(m), 3.9(d), 2.0(s, 6H), 1.0(s, 3H), 0.7(s, 3H). |
| 32 | 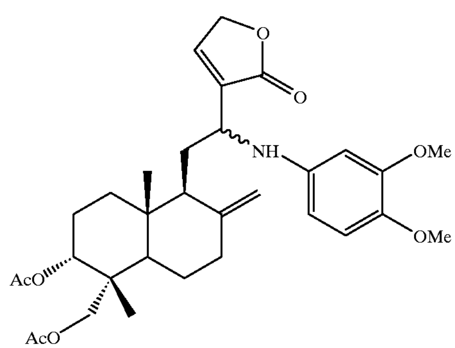 | C₃₂H₄₃O₈N m/z 569 mp 78.6° C. | ¹H NMR(CDCl₃): δ 7.15(s, 1H), 6.7(d), 6.2(s), 6.05 (d), 5.0(s, 1H, H-17a), 4.8(br s, 3H), 4.65–4.5(m), 4.35(d, 1H, H-19a), 4.25(t), 4.1(d, 1H, H-19b), 3.85(s, 3H, OMe), 3.80 (s, 3H, OMe), 2.0(s, 6H), 1.0(s, 3H), 0.7(s, 3H). |

-continued

| Example No. | Structure | Mol. formula/ Mol. wt & melting point | Spectral data |
|---|---|---|---|
| 33 | 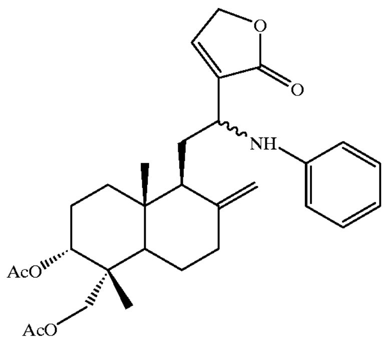 | $C_{30}H_{39}O_6N$<br>m/z 509<br>mp 114.3° C. | $^1$H NMR(CDCl$_3$):<br>δ 7.25–7.15(m), 6.75(t), 6.5(d), 5.0(s, 1H, H-17a), 4.8(s, 1H, H-17b), 4.7(s, 2H, H-15), 4.65–4.5(m), 4.4–4.2(m), 4.1(d, 1H, H-19b), 2.05(s, 6H), 1.0(s, 3H), 0.7 (s, 3H). |
| 34 | 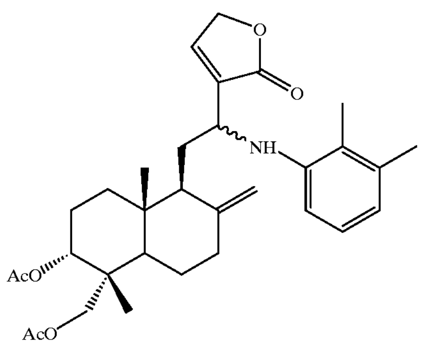 | $C_{32}H_{43}O_6N$<br>m/z 537<br>mp 87.7° C. | $^1$H NMR(CDCl$_3$):<br>δ 7.15(s, 1H), 6.9(m), 6.55(d), 6.3(d), 6.15(d), 5.0(s, 1H, H-17a), 4.8(s, 2H, H-15), 4.75(s, 1H, H-17b), 4.65–4.5(m), 4.4–4.0(m), 2.2(s, 3H), 2.0(s, 6H), 1.0(s, 3H), 0.9(s), 0.7(s, 3H). |
| 35 | 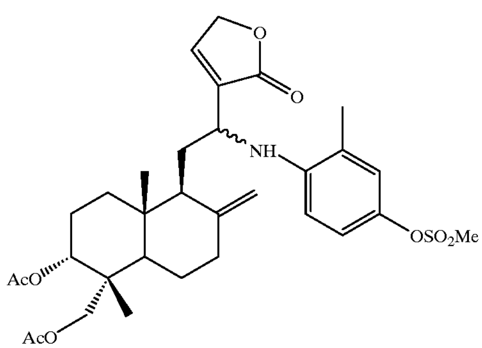 | $C_{32}H_{43}O_9NS$<br>m/z 617<br>mp 94.7° C. | $^1$H NMR(CDCl$_3$):<br>δ 7.2(s, 1H), 6.9(s), 6.3(d), 5.0(s, 1H, H-17a), 4.8(br s, 3H), 4.6(dd), 4.3(d, 1H, H-19a), 4.25(t), 4.05(d, 1H, H-19b), 3.1(s, 3H), 2.1(s, 3H), 2.0(s, 3H), 1.0 (s, 3H), 0.7(s, 3H). |
| 36 | 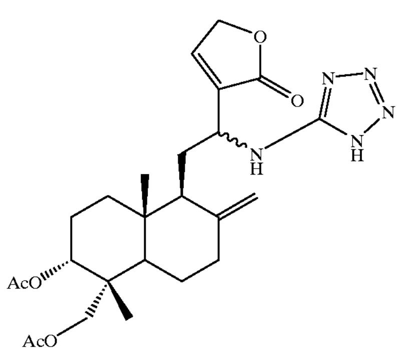 | $C_{25}H_{35}O_6N_5$<br>m/z 501<br>mp: 126° C. | $^1$H NMR(CDCl$_3$):<br>δ 7.7(s, 1H), 7.6(s), 5.1–5.3(m), 5.05(s, 2H, H-15) 4.6(m), 4.5(s, 1H, H-17b), 4.35(d, 1H, H-19a), 4.1(d, 1H, H-19b), 1(s, 6H), 1.0(s, 3H), 0.8(s, 3H). |

-continued

| Example No. | Structure | Mol. formula/ Mol. wt & melting point | Spectral data |
|---|---|---|---|
| 37 | 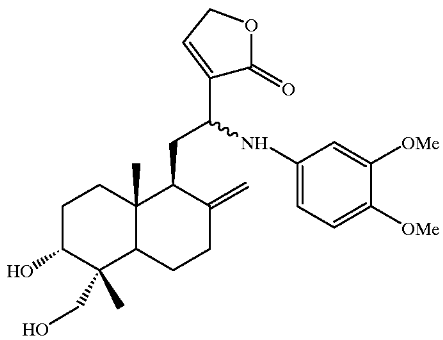 | $C_{28}H_{39}O_6N$<br>m/z 485<br>mp: 225–230° C. | $^1$H NMR(CDCl$_3$ + DMSO):<br>δ 7.2(s, 1H), 6.65(m), 6.2(s),<br>6.0(m), 4.9(s, 1H, H-17a),<br>4.75(s, 2H, H-15), 4.65(s, 1H,<br>H-17b), 3.8(s, 3H), 3.7(s, 3H),<br>1.2(s, 3H), 0.6(s, 3H). |
| 38 | 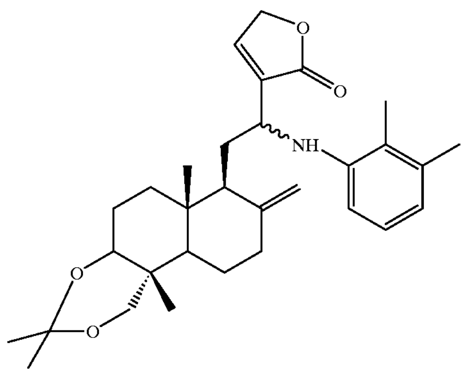 | $C_{31}H_{43}O_4N$<br>m/z 493<br>mp 192.5° C. | $^1$H NMR(CDCl$_3$):<br>δ 7.2(s, 1H), 6.9(t), 6.6(d), 6.3(d)<br>5.0(s, 1H, H-17a), 4.85(s, 1H,<br>H-17b), 4.75(s, 2H, H-15),<br>4.3(t), 4.0(d, 1H, H-19a), 3.5(dd,<br>1H, H-3), 3.2(d, 1H, H-19b),<br>2.3(s, 3H), 2.0(s, 3H), 1.5(s, 3H),<br>1.4(s, 3H), 1.2(s, 3H), 1.0(s, 3H). |
| 39 | 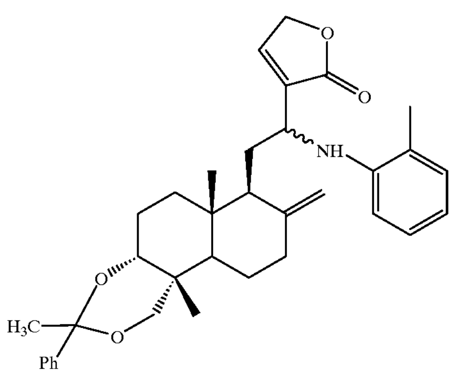 | $C_{36}H_{45}O_4N$<br>m/z 555<br>mp 224.4° C. | $^1$H NMR(CDCl$_3$):<br>δ 7.5–7.1(m), 6.9(t), 6.6(d),<br>6.2(d), 4.9(s, 1H, H-17a), 4.7(br<br>s, 3H), 4.2(t), 4.1(d, 1H, H-19a),<br>3.6(dd, 1H, H-3), 3.3(d, 1H, H-<br>19b), 2.3(s, 3H), 2.0(s, 3H),<br>1.6(s, 3H), 1.5(s, 3H), 1.4(s, 3H),<br>0.4(s, 3H). |
| 40 | 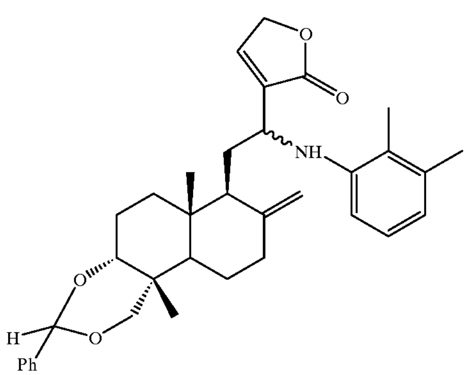 | $C_{35}H_{43}O_4N$<br>m/z 541<br>mp 118° C. | $^1$H NMR(CDCl$_3$):<br>δ 7.5–7.1(m), 6.9(t), 6.6(d),<br>6.3(d), 5.8(s), 5.0(s, 1H, H-17a),<br>4.8(s, 1H, H-17b), 4.75(s, 2H, H-<br>15), 4.3(m), 3.6(m), 2.3(s, 3H),<br>2.0(s, 3H), 1.4(s, 3H), 0.8(s,<br>3H). |

| Example No. | Structure | Mol. formula/ Mol. wt & melting point | Spectral data |
|---|---|---|---|
| 41 | 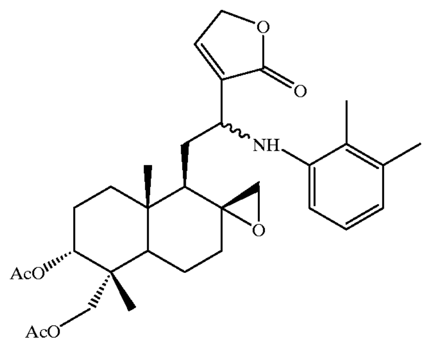 | $C_{32}H_{43}O_7N$<br>m/z 553<br>mp 125° C. | $^1H$ NMR(CDCl$_3$):<br>δ 7.15(s), 6.9(t), 6.6(d), 6.1(d),<br>4.7(s, H, H-15), 4.5(dd), 4.3<br>(d, 1H, H-19a), 4.2(d, 1H, H-19b), 3.9(d), 2.75(d, 1H, H-17a),<br>2.65(d, 1H, H-17b), 2.3(s, 3H),<br>2.2(s, 3H), 2.1(s, 3H), 2.0<br>(s, 3H), 1.0(s, 3H), 0.9(s, 3H). |

EXAMPLE 42

14-Deoxy-3,19-diacetyl-12-($N^1$-uracil) andrographolide

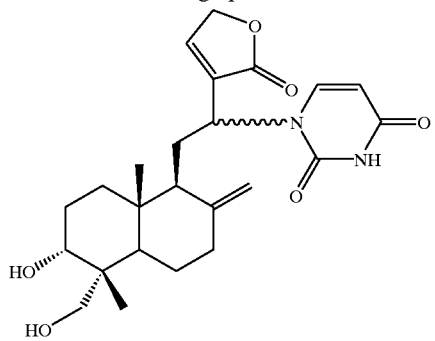

Step 1

A mixture of uracil (2 g; 0.022 moles), 1,1,1,3,3,3-hexamethyl disilazine (HMDS) (40 ml) along with catalytic amount of imidazole was refluxed for 4 hrs. After a clear solution was obtained, 1,1,1,3,3,3-hexamethyl disilazine is removed at 60° C. under low pressure to get an oily bis(trimethylsilyl) derivative of uracil.

Step 2

The above material was taken in dry dichloroethane (DCE) (60 ml), cooled to 0° C. and trimethylsilyltrifluoromethane sulphonate (4.2 ml, 0.015 moles) was added and the contents were stirred for another 15 min. 14-Acetyl andrographolide (1.0 g, 0.002 moles) in dry dichloroethane (5 ml) was added to the above and stirring continued for another 4 h at room temperature. The reaction was monitored by TLC. After the reaction was complete, the reaction mixture was quenched with methanol, diluted with aq. NaHCO$_3$ and extracted with dichloromethane. The organic layer was separated, dried and concentrated. The residue was flash chromatographed over a column of silica gel (230–400 mesh; 50 g) with chloroform:methanol (97:3) as the solvent system to get the title compound as a colourless solid (350 mg). m.p. 164° C., m/z 444.

$^1H$ NMR (CDCl$_3$): δ8.8(m, 1H), 8.6(m, 1H), 7.7(d, 1H), 7.6(d, 1H), 7.4(d, 1H), 5.7(d, 1H), 5.4(m, 1H), 5.0(s, 1H), 4.9(s, 2H), 4.6(d, 1H), 4.1(m, 2H), 3.5(m, 1H), 3.3(d, 1H), 2.8–2.4(m), 1.2(s, 3H), 0.7(s, 3H).

Examples 43–53 have been prepared by using similar procedures described in Examples 42.

| Example No. | Structure | Mol. formula/ Mol. wt & melting point | Spectral data |
|---|---|---|---|
| 43 | 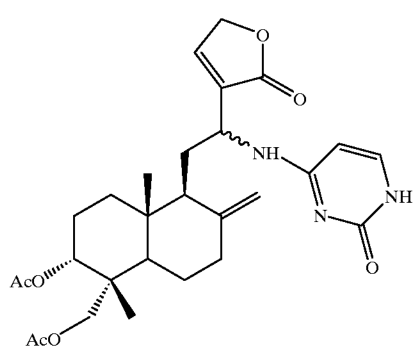 | $C_{28}H_{37}O_7N_3$<br>m/z: 527<br>mp: 229° C. | $^1H$ NMR(CDCl$_3$):<br>δ 7.7(m), 5.7(d, 1H), 5.3(d, 1H),<br>5.0(s, 1H, H-17a), 4.8(s, 2H,<br>H-15), 4.5(m), 4.3(d, 1H, H-19a), 4.1(d, 1H, H-19b), 2.8(t),<br>2.4(d), 2.0(s, 6H), 1.0(s, 3H),<br>0.7(s, 3H). |

-continued

| Example No. | Structure | Mol. formula/ Mol. wt & melting point | Spectral data |
|---|---|---|---|
| 44 | 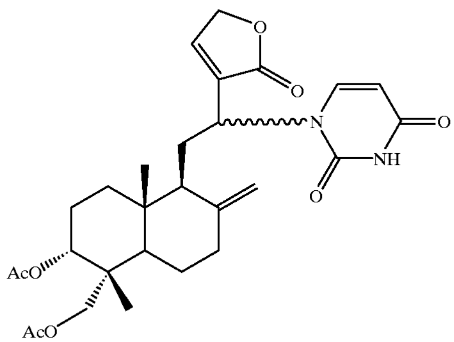 | $C_{28}H_{36}O_8N_2$ m/z 528 mp: 152° C. | $^1$H NMR(CDCl$_3$): δ 9.0(br s, 1H), 7.6(m), 7.5(s, 1H), 7.3(d, 1H), 5.7(m), 5.3(s), 5.0(s, 1H, H-17a), 4.85(s, 1H, H-17b), 4.8(s, 2H, H-15), 4.5 (m), 4.3(d, 1H, H-19a), 4.1 (d, 1H, H-19b), 2.8–2.3(m), 2.0 (s, 6H), 1.8–1.2(m), 1.0(s, 3H), 0.7(s, 3H). |
| 45 | 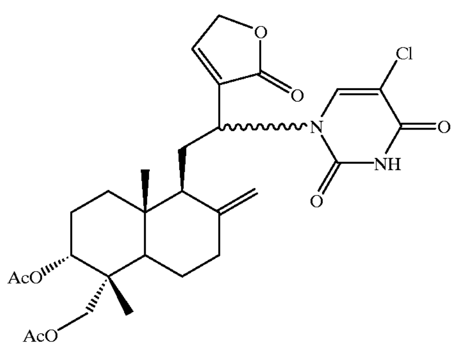 | $C_{28}H_{35}O_8N_2Cl$ m/z 562 mp: 198° C. | $^1$H NMR(CDCl$_3$): δ 8.7(s, 1H), 7.9(s, 1H), 7.6(s, 1H), 5.3(m), 5.0(s, 1H, H-17a), 4.9(s, 2H, H-15), 4.6(m, 2H), 4.3(d, 1H, H-19a), 4.1(d, 1H, H-19b), 2.8–2.4(m), 2.0(s, 6H) 1.8–1.2(m), 1.0(s, 3H), 0.7 (s, 3H). |
| 46 | 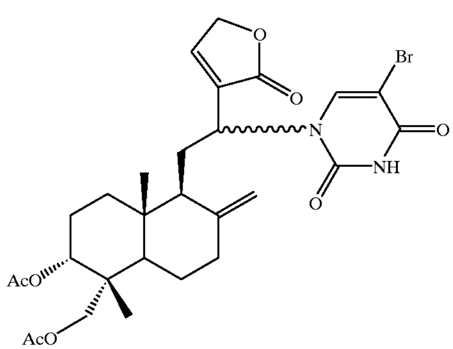 | $C_{28}H_{35}O_8N_2Br$ m/z 606 mp: 152° C. | $^1$H NMR(CDCl$_3$): δ 8.7(br s, 1H), 8.0(s, 1H), 7.6 (s, 1H), 5.3(m), 5.05(s, 1H, H-17a), 4.95(s, 2H, H-15), 4.6(m, 2H), 4.3(d, 1H, H-19a), 4.1(d, 1H, H-19b), (2.8–2.3(m), 2.0(s, 6H), 1.8–1.2(m), 1.0(s, 3H), 0.8(s, 3H). |
| 47 | 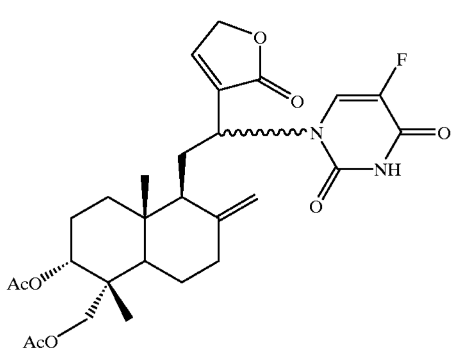 | $C_{28}H_{35}O_8N_2F$ m/z 546 mp: 149° C. | $^1$H NMR(CDCl$_3$): δ 8.7(s, 1H), 7.8(d, 1H), 7.6(d, 1H), 7.5(d, 1H), 5.3(d, 1H),5.0 (s, 1H, H-17a), 4.9(d, 2H, H-15), 4.6(s, 1H, H-17b), 4.3(d, 1H, H-19a), 4.1(d, 1H, H-19b), 2.8–2.4(m), 2.0(s, 6H), 1.8–1.2(m), 1.1(s, 3H), 0.7(s, 3H). |

| Example No. | Structure | Mol. formula/ Mol. wt & melting point | Spectral data |
|---|---|---|---|
| 48 | 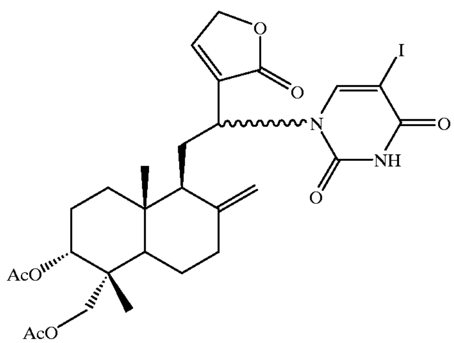 | $C_{28}H_{37}N_2O_8I$<br>m/z 656<br>mp: 170° C. | $^1$H NMR(CDCl$_3$):<br>δ 8.4(m, 1H), 8.1(s, 1H), 7.6(s, 1H), 5.3(m, 1H), 5.0(m, 3H), 4.6(m, 1H), 4.4(d, 1H, H-19a), 4.1(d, 1H, H-19b), 2.8(m), 2.5(m), 2.1(s, 6H), 1.0(s, 3H), 0.7(s, 3H). |
| 49 | 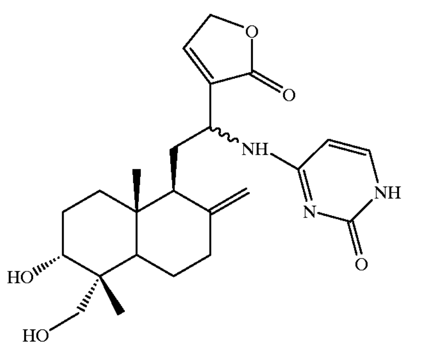 | $C_{24}H_{33}O_5N_3$<br>m/z 443<br>mp: 163° C. | $^1$H NMR(CDCl$_3$):<br>δ 8.3(s, 1H), 7.8(s, 1H), 7.6(d, 1H), 7.0(m, 1H), 5.7(d, 1H), 5.4(m, 1H), 4.9(s, 2H), 4.8(m, 2H), 3.8(d, 1H), 3.2(m, 2H), 2.6–2.2(m), 1.2(s, 3H), 0.6(s, 3H). |
| 50 | 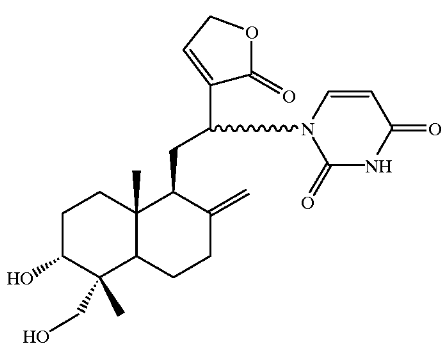 | $C_{24}H_{32}O_6N_2$<br>m/z 444<br>mp: 164° C. | $^1$H NMR(CDCl$_3$):<br>δ 8.8(m, 1H), 8.6(m, 1H), 7.7(d, 1H), 7.6(d, 1H), 7.4(d, 1H), 5.7(d, 1H), 5.4(m, 1H), 5.0(s, 1H), 4.9(s, 2H), 4.6(d, 1H), 4.1(m, 2H), 3.5(m, 1H), 3.3(d, 1H), 2.8–2.4(m), 1.2(s, 3H), 0.7(s, 3H). |
| 51 | 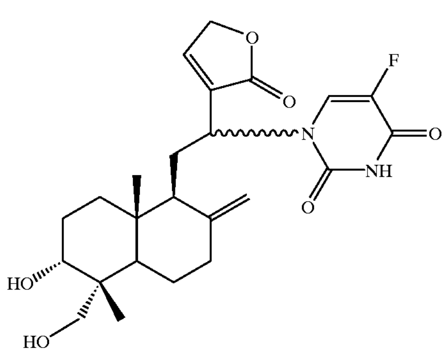 | $C_{24}H_{31}N_2O_6F$<br>m/z 462<br>mp: 155° C. | $^1$H NMR(CDCl$_3$):<br>δ 8.9(s), 8.8(s), 7.8(d, 1H), 7.5 (m, 2H), 5.4(d, 1H), 5.1(d, 1H), 5.05(s, 1H, H-17a), 5.0(s, 2H, H-15), 4.6(s, 1H, H-17b), 4.2 (d, 1H, H-19a), 3.5(m, 1H), 3.3(d, 1H, H-19b), 2.8–2.3(m), 1.2(s, 3H), 0.7(s, 3H). |

-continued

| Example No. | Structure | Mol. formula/ Mol. wt & melting point | Spectral data |
|---|---|---|---|
| 52 | 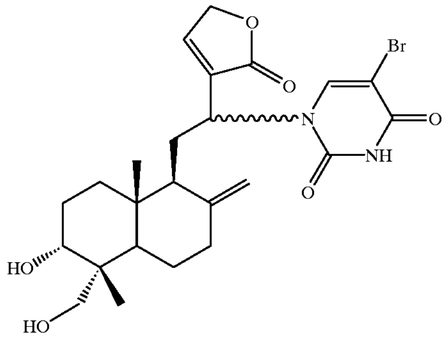 | $C_{24}H_{31}N_2O_6Br$<br>m/z 523<br>mp: 185° C. | $^1$H NMR(CDCl$_3$):<br>δ 8.8(s, 1H), 8.0(s, 1H), 7.6(m, 2H), 5.4(m, 1H), 5.05(s, 1H, H-17a), 5.0(s, 2H, H-15), 4.6 (s, 1H, H-17b), 4.2(m), 3.5 (m, 1H), 3.3(m, 1H), 2.7–2.2(m), 1.2(s, 3H), 0.7(s, 3H). |
| 53 | 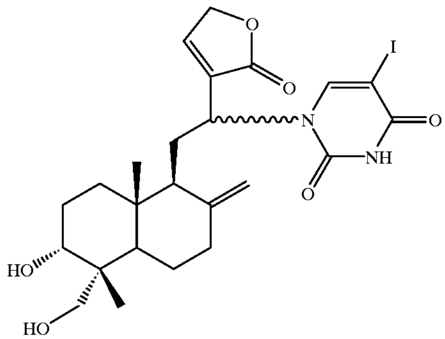 | $C_{24}H_{31}N_2O_6I$<br>m/z 570<br>mp: 187–188° C. | $^1$H NMR(CDCl$_3$):<br>δ 11.4(s, 1H), 8(s, 1H), 7.6(s, 1H), 5.3(d, 1H), 5.0(br s, 2H), 4.6(s, 1H), 4.0(m, 2H), 3.2(m, 2H), 1.2(s, 3H), 0.7(s, 3H). |

EXAMPLE 54

14-Deoxy-8,17-epoxy-12-phenylthio andrographolide

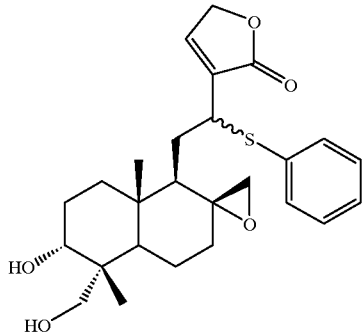

To a solution of thiophenoxide prepared by stirring thiophenol (0.25 ml, 2.27 mmol) with triethylamine (0.4 ml, 2.87 mmol) in dichloromethane (50 ml) for 10 min at room temperature, 14-acetyl-8,17-epoxy andrographolide (500 mg, 1.22 mmol) was added and the contents were stirred for an additional 2 h. The reaction was monitored by TLC. After completion of the reaction, the reaction mixture was poured onto a column of silica gel (230–400 mesh; 50 g) and eluted with chloroform:acetone=90:10) to obtain crude 14-deoxy-8,17-epoxy-12-thiophenoxy andrographolide (85% pure) which was rechromatographed using a column of silica gel (230–400 mesh; 50 g) with light petrol:acetone (8:2) as eluent to get the title compound as a colourless solid (135 mg). m.p. 90° C., m/z 458.

$^1$H NMR: 7.4–7.1(m), 4.8(s, 2H, H-15), 4.1(m), 3.5(t), 3.3(d), 2.8(d, 1H, H-17a), 2.5(d, 1H, H-17b), 1.3(s, 3H), 0.7(s, 3H).

EXAMPLE 55

3,19-Diacetyl-14-deoxy-12-(phenylselenyl) andrographolide

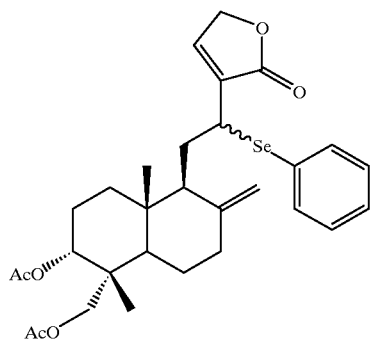

Step 1

Preparation of selenophenoxide

A solution of selenophenoxide is prepared by treating diphenyl diselenide (312 mg) in ethanol (7 ml) with sodium borohydride (46 mg, added slowly in three portions) at room temperature, the contents were stirred for 30 min. The resulting pale yellow solution of sodium benzeneselenotate was cooled to 0° C., and treated with acetic acid (130 μl);

Step 2

3,14,19-Triacetyl andrographolide (500 mg) (Ref: *Journal of Chemical Society*, 1952, p-1697–1700) was added to the above reaction mixture and stirring continued for one hour. The reaction was monitored by TLC. After completion of the reaction, the reaction mixture was poured into water (200 ml), extracted with dichloromethane. The organic layer was separated, dried over $Na_2SO_4$ and concentrated. The crude material was purified by flash column chromatography (silica gel (230–400 mesh; 49 g) with chloroform:acetone (1 liter:6 ml) as the eluent to get the title compound as a colourless solid (120 mg). m/z 5735.

$^1$H NMR: 7.5–7.2(m), 6.7(s, 1H), 4.9(s, 1H, H-17a), 4.65(d, 2H, H-15), 4.5(s, 1H, H-17b), 4.4 (d, 1H, H-19a), 4.1(d, 1H, H-19b), 4.0(d), 2.4–2.2(m), 2.0(s, 6H), 1.0(s, 3H), 0.7(s, 3H).

EXAMPLE 56

12-(C-Benzoylmethyl)-14-deoxy-3,19-O-(1-phenylethylidene)andrographolide

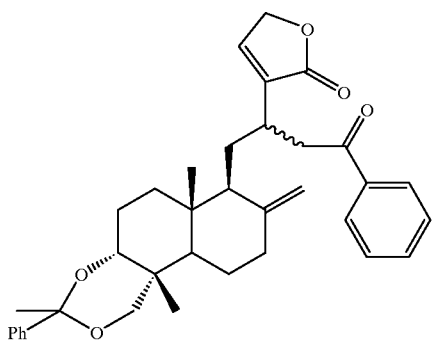

To a solution of LDA (generated by addition of n-butyl lithium 2.27 ml to diisopropyl amine 0.56 ml in 10 ml of dry THF at 0° C. stirred for 10 min) was added acetophenone (0.47 ml) in 2 ml THF at –78° C., stirring continued for 1 h at the same temperature.

To the above 14-acetyl-3,19-O-(1-phenylethylidene) andrographolide (500 mg) in 2 ml dry THF was added and the contents stirred for 2 h. The reaction was monitored by TLC. After completion of the reaction, the reaction mixture was quenched with saturated ammonium chloride solution and extracted with dichloromethane. The organic layer was separated, dried and concentrated. The residue was purified by flash chromatography over a column of silica gel (230–400 mesh; 50 g) with light petrol:ethyl acetate (85:15) as the eluent to get the title compound as a colourless solid (230 mg). m/z 554.

$^1$H NMR (CDCl$_3$): 7.9(d), 7.6–7.2(m), 4.9(s, 1H, H-17a), 4.7(s, 2H, H-15), 4.65(s, 1H, H-17b), 4.0(d, 1H, H-19a), 3.6–3.1(m), 2.4(d), 1.6(s, 3H), 1.5(s, 3H), 1.4(s, 3H), 0.4(s, 3H).

EXAMPLE 57

14-Deoxy-3,19-O-isopropylidene-12-ethylthio andrographolide

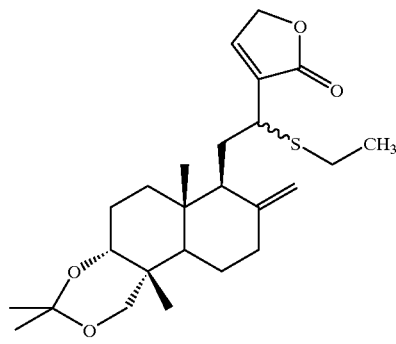

A mixture of 14-acetyl-3,19-O-isopropylidene andrographolide (2 g), triethyl amine (1.4 ml) and thioethanol (1 ml) in dichloromethane (150 ml) was stirred for 48 h. The reaction was monitored by TLC. After completion of the reaction, the reaction mixture was diluted with diethyl ether, washed with water, the organic layer separated, dried over $Na_2SO_4$ and concentrated. The residue obtained was purified by chromatography over a column of silica gel (230–400 mesh; 50 g) with light petrol:ethyl acetate (85:15) to obtain the title compound as a colourless solid (1.4 g). m/z 434.

$^1$H NMR (CDCl$_3$): δ7.3(s, 1H), 4.95(s, 1H, H-17a), 4.8(s, 2H, H-15), 4.7(s, 1H, H-17b), 3.95(d, 1H, H-19a), 3.5(m), 3.2(d, 1H, H-19b), 2.4(m), 2.2(d), 2–1.6(m), 1.4(s, 3H), 1.35(s, 3H), 1.2(s, 3H), 0.9(s, 3H).

Examples 58–70 have been prepared by using similar procedures described in Examples 54–57.

| Example No. | Structure | Mol. formula/ Mol. wt | Spectral data |
|---|---|---|---|
| 58 | 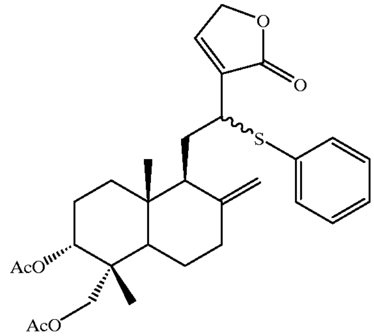 | $C_{30}H_{38}O_6S$<br>m/z: 526<br>mp: 135° C. | $^1$H NMR(CDCl$_3$):<br>δ 7.25(br s), 4.95(s, 1H, H-17a), 4.8(s, 1H, H-17b), 4.75(s, 2H, H-15), 4.4(d, 1H, H-19a), 4.1(d, 1H, H-19b), 2.4(m), 2.0(s, 6H), 1.0(s, 3H), 0.7(s, 3H). |

-continued

| Example No. | Structure | Mol. formula/ Mol. wt | Spectral data |
|---|---|---|---|
| 59 | 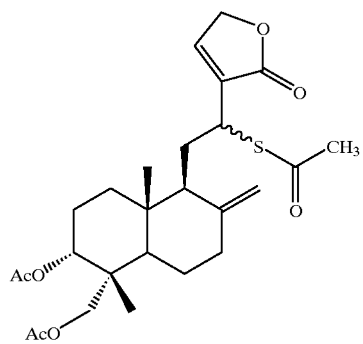 | $C_{26}H_{36}O_7S$<br>m/z 492<br>mp: 65° C. | $^1$H NMR(CDCl$_3$):<br>δ 7.3(s, 1H, H-14), 5.0(s, 1H, H-17a), 4.85(br s, 1H, H-15) 4.75(s, 1H, H-17b), 4.5(m), 4.3(d, 1H, H-19a), 4.1 (d, 1H, H-19b), 2.4(m), 2.0 (s, 6H), 1.0(s, 3H), 0.7(s, 3H). |
| 60 | 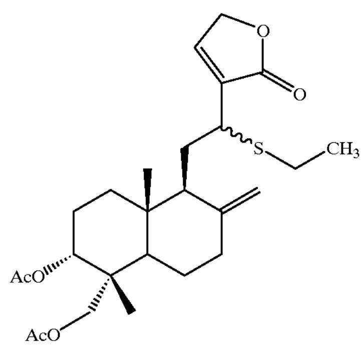 | $C_{26}H_{38}O_6S$<br>m/z 478<br>mp: 99.3–100° C. | $^1$H NMR(CDCl$_3$):<br>δ 7.3(m, 1H), 4.9(m), 4.6(m), 4.4(m, 1H), 4.1(m, 1H), 3.7 (d, 1H), 3.5(d, 1H), 2.4(m), 2.0(s, 6H), 1.9–1.1(m), 1.0 (m, 3H), 0.7(s, 3H). |
| 61 | 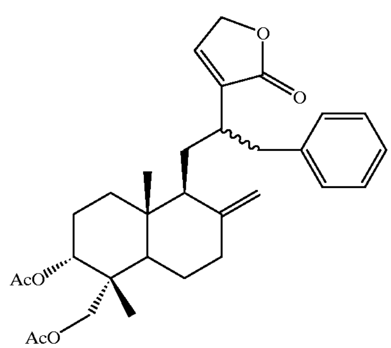 | $C_{34}H_{45}O_6N$<br>m/z 563<br>mp: 141–143° C. | $^1$H NMR(CDCl$_3$):<br>δ 7.3–7.0(m), 6.85(s, 1H), 4.9 (s, 1H, H-17a), 4.7(br s, 3H), 4.6(t), 4.35(d, 1H, H-19a), 4.1(d, 1H, H-19b), 2.9(s), 2.4(m), 2.1(s, 6H), 1.9–1.5(m), 1.3(m), 1.0 (s, 3H), 0.7(s, 3H). |
| 62 | 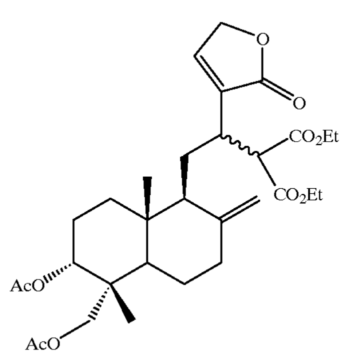 | $C_{34}H_{45}O_6N$<br>m/z 563<br>mp: 141–143° C. | $^1$H NMR(CDCl$_3$):<br>δ 7.4–7.2(m), 4.9–4.55(m), 4.5–4.0(m), 3.8(m), 3.5–3.2 (m), 2.4(m), 2.0(s, 6H), 1.8–1.2(m), 1.0(s, 3H), 0.7(s, 3H). |

-continued

| Example No. | Structure | Mol. formula/ Mol. wt | Spectral data |
|---|---|---|---|
| 63 | 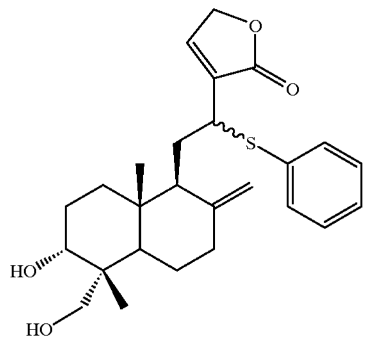 | $C_{26}H_{34}O_4S$ m/z 442 mp: 105° C. | $^1$H NMR(CDCl$_3$): δ 7.3(s, 5H), 4.9(s, 1H, H-17a), 4.75(s, 1H, H-17b), 4.7(s, 2H, H-15), 4.2(d, 1H, H-19a), 4.1(d), 3.5(t, 1H), 3.3(d, 1H, H-19b), 1.3(s, 3H), 0.7(s, 3H). |
| 64 | 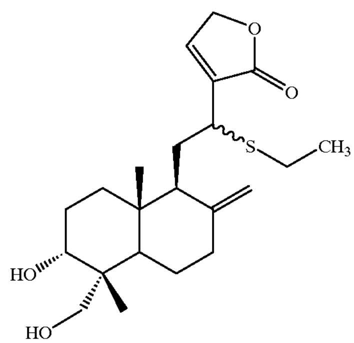 | $C_{22}H_{34}O_4S$ m/z 394 mp: 160° C. | $^1$H NMR(CDCl$_3$): δ 7.3(s, 1H), 4.9(s, 1H, H-17a), 4.7(s, 2H, H-15), 4.6(s, 1H, H-17b), 4.2(d, 1H, H-19a), 3.5(m), 3.3(d, 1H, H-19b), 2.4(m), 2.2(d, 1H), 2.0–1.6(m), 1.2(m), 0.6(s, 3H). |
| 65 | 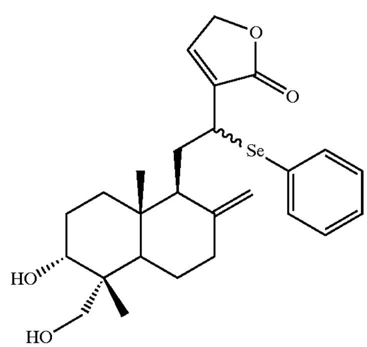 | $C_{26}H_{34}O_4Se$ m/z: 489.45 mp: 186° C. | $^1$H NMR(CDCl$_3$): δ 7.5–7.2(m, 1H), 6.7(s, 1H), 4.85 (s, 1H, H-17a), 4.65(s, 2H, H-15), 4.4(s, 1H, H-17b), 4.2(d, 1H, H-19a), 4.0(d), 3.5(t), 3.3(s, 1H, H-19b), 2.4(m), 1.3(s, 3H), 0.6(s, 3H). |
| 66 | 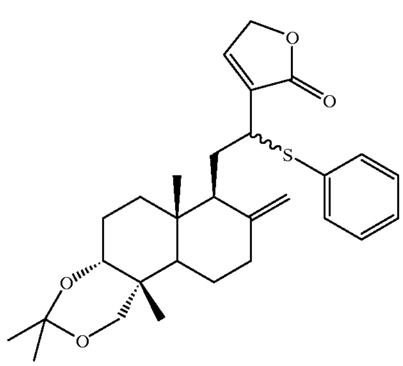 | $C_{29}H_{38}O_4S$ m/z 482 154.8° C. | $^1$H NMR(CDCl$_3$): δ 7.3(s), 4.95(s, 1H, H-17a), 4.85(s, 1H, H-17b), 4.75 (s, 2H, H-15), 4.2(d, 1H),4.0 (d, 1H, H-19a), 3.5(dd, 1H), 3.2(d, 1H, H-19b), 2.4(m), 1.4(s, 3H), 1.35(s, 3H), 1.2(s, 3H), 0.9(s, 3H). |

-continued

| Example No. | Structure | Mol. formula/ Mol. wt | Spectral data |
|---|---|---|---|
| 67 | 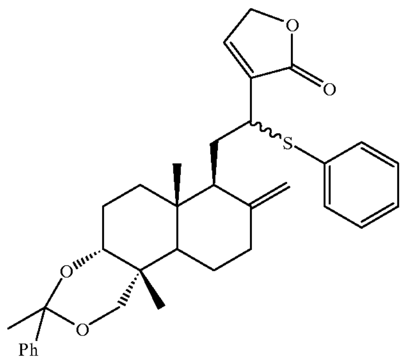 | $C_{34}H_{40}O_4S$ m/z 544 mp: 154.1° C. | $^1$H NMR(CDCl$_3$): δ 7.5–7.1(m), 7(s, 1H), 4.9 (s, 1H, H-17a), 4.7(br s, 3H), 4.0(t, 2H), 3.6(dd, 1H), 3.3(d, 1H), 2.4(d), 2.2(d, 1H), 1.5(s, 3H), 1.4(s, 3H), 0.4(s, 3H). |
| 68 | 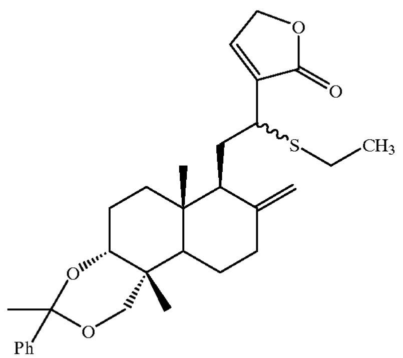 | $C_{30}H_{40}O_4S$ m/z 496 mp: 122.5–125° C. | $^1$H NMR(CDCl$_3$): δ 7.5–7.2(m), 4.9(s, 1H, H-17a), 4.8(s, 1H, H-15), 4.6(s, 1H, H-17b), 4.1(d, 1H, H-19a), 3.7(dd), 3.5(d), 3.3(d, 1H, H-19b), 2.4(m), 2.2–1.55(m), 1.5(s, 3H), 1.35(s, 3H), 0.4(s, 3H). |
| 69 | 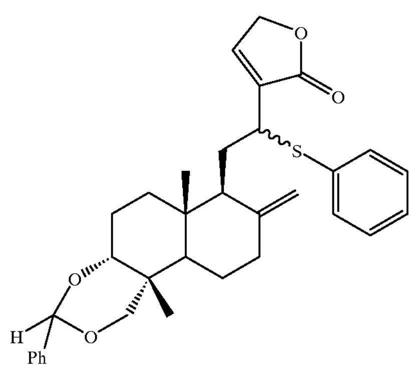 | $C_{33}H_{38}O_4S$ m/z 530 mp: 74–76° C. | $^1$H NMR(CDCl$_3$): δ 7.5–7.1(m), 6.9(s, 1H), 5.75(d, 1H), 4.9(s, 1H, H-17a), 4.8(s, 1H, H-17b), 4.7 (br s, 2H, H-15), 4.2(m), 4.1 (d, 1H, H-19a), 3.6(m), 2.4 (m), 1.6(s, 3H), 1.4(m), 0.9(s, 3H). |
| 70 | 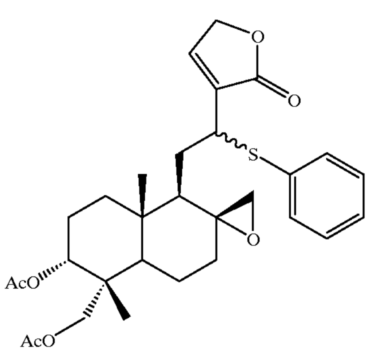 | $C_{30}H_{38}O_7S$ m/z 542 mp: 152° C. | $^1$H NMR(CDCl$_3$): δ 7.4–7.1(m), 4.7(s, 2H, H-15), 4.6(m), 4.3(d, 1H, H-19a), 4.1(d, 1H, H-19b), 2.8(d, 1H, H-17a), 2.5 (d, 1H, H-17b), 2.0(s, 6H), 1.0(s, 3H), 0.8(s, 3H). |

EXAMPLE 71

14-Deoxy-12-hydroxy andrographolide

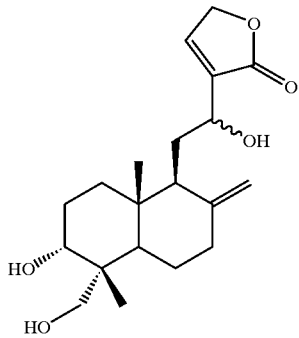

Step 1

To a solution of 3,19-isopropylidene andrographolide (15.5 g, 39.74 mmol) in dichloromethane (250 ml) was added pyridinium dichromate (700 mg, 1.86 mmol) in small portions (100 mg each time) over a period of 2 h at room temperature with stirring. The reaction was monitored by TLC. After completion of the reaction, the reaction mixture was poured onto a column of silica gel (230–400 mesh; 500 g) and eluted with light petrol:ethyl acetate (60:40) to get 12-hydroxy-3,19-isopropylidene andrographolide (15 g) as a colourless solid.

Step 2

12-hydroxy-3,19-isopropylidene andrographolide (700 mg) obtained in the above step was treated with aq. acetic acid (20 ml; acetic acid:water=7:3) for 30 min at room temperature. The reaction was monitored by TLC. After completion of the reaction, the reaction mixture was diluted with water, neutralised with NaHCO$_3$, extracted with ethyl acetate, the organic layer was separated, dried over sodium sulphate and concentrated. The concentrated extract was purified over a column of silica gel (230–400 mesh; 50 g) with chloroform:acetone (80:20) as an eluent to get the title compound as a colourless solid (570 mg), m/z 350.

EXAMPLE 72

12-Cinnamoyloxy-14-deoxy andrographolide

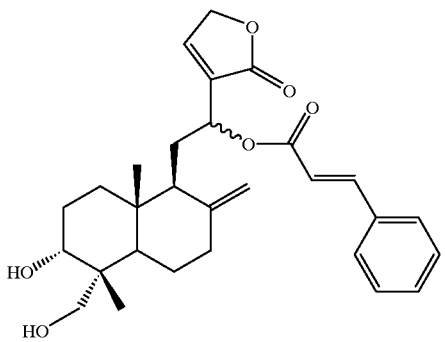

Step 1

A mixture of 12-hydroxy-3,19-isopropylidene andrographolide (1 g), DCC(1.4 g), cinnamic acid (1 g) and dimethylaminopyridine (DMAP) (100 mg) in dichloromethane (80 ml) was stirred for 4 h at room temperature. The reaction was monitored by TLC. After completion of the reaction, the reaction mixture diluted with dichloromethane, washed with aq. copper sulphate, water, the organic layer separated, dried over Na$_2$SO$_4$ and concentrated. The residue obtained was purified over a column of silica gel (230–400 mesh; 50 g) with light petrol:ethyl acetate (9:1–8:2) to get the 12-cinnamoyloxy-14-deoxy-3,19-isopropylidene andrographolide as a colourless solid (1 g).

Step 2

12-cinnamoyloxy-3,19-isopropylidene andrographolide (500 mg) obtained in step 1 was treated with 20 ml aq. acetic acid (acetic acid:water=7:3), stirred at room temperature for 5 min. The reaction was monitored by TLC. After completion of the reaction, the mixture was neutralized with aq. NaHCO$_3$, extracted with ethyl acetate. The organic layer was separated, dried over Na$_2$SO$_4$, concentrated. The residue was purified over a column of silica gel (230–400 mesh; 50 g) with light petrol:ethylacetate as eluent to get 12-cinnamoyloxy-14-deoxy andrographolide as a colourless solid (280 mg). m/z 480.

$^1$H NMR(CDCl$_3$): 7.7(d), 7.5–7.3(m), 6.4(d, 1H), 5.8(dd), 4.9(s, 1H, H-17a), 4.85(s, 2H, H-15), 4.75(s, 1H, H-17b), 4.2(d, 1H, H-19a), 3.5(t, 1H), 3.3(d, 1H, H-19b), 2.4(m), 1.2(s, 3H), 0.6(s, 3 H).

EXAMPLE 73

12-Cinnamoyloxy-14-deoxy-8,17-epoxy-andrographolide

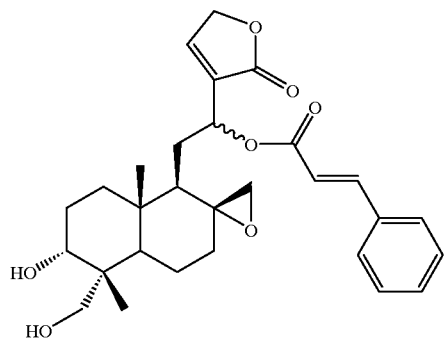

12-Cinnamoyloxy-14-deoxy-3,19-isopropylidene andrographolide (1 g) in dichloromethane (100 ml), prepared by the method described in step 1 of the example 2, was treated with m-CPBA (2 g), stirred for 4 h at room temperature. The reaction was monitored by TLC. After completion of the reaction, the reaction mixture was concentrated, chromatographed over a column of silica gel (230–400 mesh; 50 g) with light petrol:ethyl acetate as the eluent to obtain the title compound as a colourless solid (740 mg). m/z 490.

$^1$H NMR: 7.8(d), 7.4–7.2(m), 6.5(d, 1H), 5.8(m, 1H), 4.8(s, 2H, H-15), 4.2(d, 1H, H-19a), 3.5(t, 1H), 3.3(d, 1H, H-19b), 2.7(d, 1H, H-17a), 2.5(d, 1H, H-17b), 1.0(s, 3H), 0.8(s, 3H).

Examples 74–77 have been prepared by using similar procedures described in Examples 71–73.

| Example No. | Structure | Mol. formula/ Mol. wt | Spectral data |
|---|---|---|---|
| 74 | 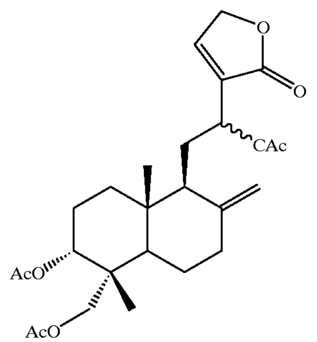 | C$_{26}$H$_{36}$O$_8$ m/z 476 mp: 152.7° C. | $^1$H NMR(CDCl$_3$): δ 7.35(s, 1H, H-14), 5.7(m, 1H, H-12), 4.9(s, 1H, H-17a), 4.85(s, H, H-15), 4.75(s, 1H, H-17b), 4.6(m), 4.3(d, 1H, H-19a), 4.1(d, 1H, H-19b), 2.4(d), 2.1(s, 3H), 2.0(s, 3H), 1.0(s, 3H), 0.7(s, 3H). |
| 75 | 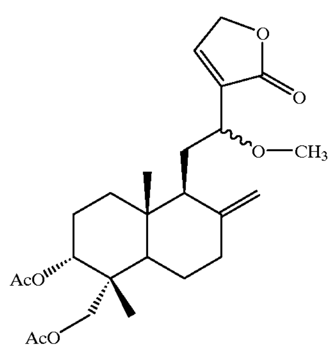 | C$_{25}$H$_{36}$O$_7$ m/z 448 | $^1$H NMR(CDCl$_3$): δ 7.3(m), 4.9(s, 1H, H-17a), 4.9(m, 3H), 4.6(m), 4.4(m), 4.1(m), 3.3(s, 3H), 2.0(s, 6H), 1.2(s, 3H), 0.7(s, 3H). |
| 76 | 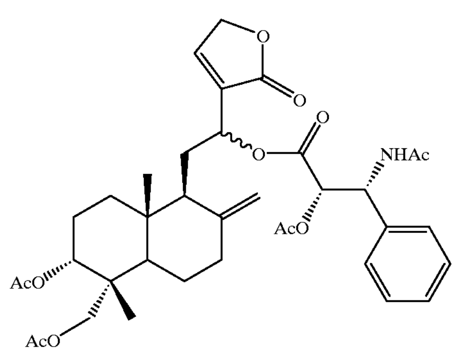 | C$_{37}$H$_{47}$O$_{11}$N m/z 681 mp: 101° C. | $^1$H NMR(CDCl$_3$): δ 7.3(m), 6.5(d), 5.7(m), 5.3 (d), 4.9(s, 1H, H-17a), 4.85 (s, 2H, H-15), 4.7(s, 1H, H-17b), 4.5(m), 4.3(d, 1H, H-19a), 4.1(d, 1H, H-19b), 2.4(m), 2.2(s, 3H), 2.0(m, 9H), 1.0(s, 3H), 0.7 (s, 3H). |

-continued

| Example No. | Structure | Mol. formula/ Mol. wt | Spectral data |
|---|---|---|---|
| 77 | 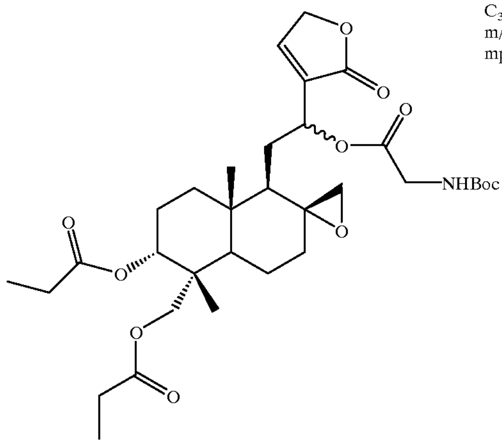 | $C_{33}H_{49}O_{11}N$<br>m/z 635<br>mp: 80° C. | $^1$H NMR(CDCl$_3$):<br>δ 7.4(s, 1H), 5.7(t, 1H), 5 (m, 1H), 4.8(s, 2H, H-15), 4.6(m), 4.3(m), 3.9(d, 2H), 2.3(m), 1.8–1.2(m), 1.0(s, 3H), 0.8(s, 3H). |

EXAMPLE 78

3,19-Diacetyl-14-deoxy-12-mercaptobenzothiazolyl andrographolide

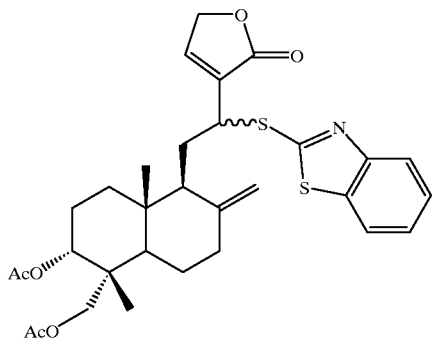

To a stirred mixture of 2-mercaptobenzothiazole (421 mg, 2.52 mmol), triethyl amine (0.7 ml) in diethylether (100 ml), 3,14,19-triacetyl andrographolide (600 mg, 1.26 mmol) was added at room temperature. The contents were stirred for 4 h. The reaction was monitored by TLC. After completion of the reaction, the reaction mixture was diluted with diethylether, washed with water, dried over Na$_2$SO$_4$ and concentrated. The residue obtained was chromatographed over a column of silica gel (230–400 mesh; 55 g) with light petrol:ethyl acetate (75:25) as the eluent to obtain 3,19-diacetyl-14-deoxy-12-mercaptobenzothiazolyl andrographolide (400 mg, 54.4%) as a colourless product. m.p. 82° C., m/z 583.

$^1$H-NMR (CDCl$_3$): δ7.8(m), 7.7(d), 7.4(m), 7.3(m), 5.0 (m), 4.8(m), 4.6(dd), 4.4(d, 1H, 19a), 4.1(d, 1H, 19b), 2.0(s, 6H), 1.2–1.9(m), 1.0(s, 3H), 0.7(s, 3H).

EXAMPLE 79

3,19-Diacetyl-12-(N,N-benzylchloroacetyl)amino-14-deoxy-12-andrographolide

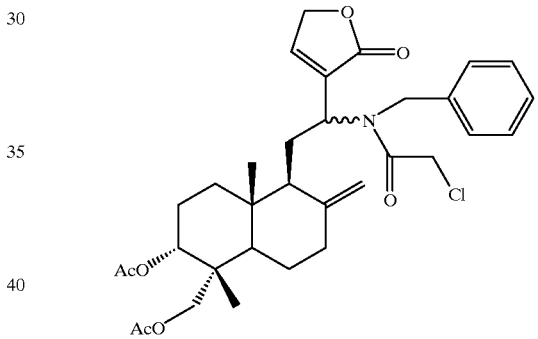

To a mixture of chloro acetyl chloride (122 μl, 1.529 mmol), triethyl amine (320 μl) in dichloromethane (30 ml), 3,19-diacetyl-12-(N-benzylamino)-14-deoxy andrographolide (400 mg, 0.764 mmol) was added at room temperature. The contents were stirred for 30 min. The reaction was monitored by TLC. After confirming the completion of the reaction, the reaction mixture was diluted with dichloromethane, washed with water, dried over Na$_2$SO$_4$ and concentrated. The residue obtained was chromatographed over a column of silica gel (230–400 mesh; 55 g) with light petrol:ethyl acetate (60:40) as an eluent to obtain 3,19-diacetyl-12-(N,N-benzyl chloroacetyl)amino-14-deoxy andrographolide (350 mg, 76.27%) as a colourless product.m.p. 199.2° C., m/z 600.

$^1$HNMR (CDCl$_3$): δ7.6(s, 1H, H-14), 7.1–7.4(m), 4.8–4.6 (m), 4.55(dd, 1H, H-3), 4.35(d, 1H, 19a), 4.1(m), 2.0(s, 6H), 1.0(s, 3H), 0.6(s, 3H).

Anti-Cancer Activity

The compounds prepared in the present invention exhibited good in vitro anti-cancer activity towards various human tumor cell lines.

Each test compound was screened against a battery of cell lines representing eight different types of cancers. In a typical procedure, 1×10⁴ cells were seeded into each well of 96 well plate in 100 μL volume of RPMI 1640 medium containing antibiotics and 10% FCS.

The plates were incubated at 37° C. in presence of $CO_2$. After 24 h, test compounds were evaluated at five 10 fold dilutions ranging from 100 to 0.01 μM. To each test well 100 μL of test compound solution was added and medium with vehicle was added to control wells and the plates were further incubated. After 48 h of incubation, plates were terminated by Sulforhodamine B method.

The optical density which is proportional to protein mass, is then-read by automated spectrophotometric plate reader at a wavelength of 515 nm. Readings were transferred to a microcomputer and mean 50% Growth Inhibition (GI50). The compounds of the present invention showed anticancer activity, which can be seen from the data given below:

| PANEL/ CELL LINE | GROWTH INHIBITION (GI 50) [μM] Example Nos. | | | | | | | | | |
|---|---|---|---|---|---|---|---|---|---|---|
| | 1 | 3 | 58 | 70 | 18 | 51 | 21 | 48 | 22 | 23 |
| BREAST: | | | | | | | | | | |
| MCF-7/ADR | 8.0 | 5.0 | 6.5 | 8.0 | 2.5 | 4.0 | 1.0 | 2.0 | 2.0 | 2.0 |
| MCF7 | — | — | — | — | 3.0 | 4.0 | 3.0 | 2.0 | 3.0 | 4.0 |
| CNS: | | | | | | | | | | |
| U251 | 0.2 | 8.0 | 4.0 | 7.0 | 0.07 | 2.0 | 2.0 | 2.0 | 3.0 | 2.0 |
| COLON: | | | | | | | | | | |
| SW-620 | 4.0 | 3.5 | 5.0 | 4.0 | 2.5 | 3.5 | 2.0 | 4.0 | 3.0 | 2.0 |
| HT29 | — | — | — | — | 10.0 | 10.0 | 3.0 | 4.0 | 3.0 | 3.0 |
| LUNG: | | | | | | | | | | |
| H522 | 9.0 | 0.18 | 7.0 | 7.0 | 6.0 | 5.0 | 3.0 | 4.0 | 20.0 | 15.0 |
| MEL-ANOMA: | | | | | | | | | | |
| UACC62 | — | — | — | — | 3.5 | 6.0 | 2.0 | 3.0 | 3.0 | 2.0 |
| M14 | 5.0 | 5.5 | 4.0 | 3.0 | — | — | — | — | — | — |
| OVARIAN: | | | | | | | | | | |
| SKOV-3 | 0.3 | 0.15 | 6.0 | 4.0 | 4.0 | 7.0 | 2.0 | 3.0 | 4.0 | 4.0 |
| OVCAR | — | — | — | — | — | — | — | — | 1.4 | 1.0 |
| PA1 | — | — | — | — | 3.0 | 3.0 | 2.0 | 2.0 | 1.4 | 1.0 |
| PROSTATE: | | | | | | | | | | |
| DU145 | 7.0 | 8.0 | 7.5 | 2.0 | 10.0 | 15.0 | — | — | 12.0 | 11.0 |
| PC-3 | — | — | — | — | 2.5 | 3.0 | — | — | 2.0 | 2.0 |
| RENAL: | | | | | | | | | | |
| A498 | 5.0 | 0.18 | 0.2 | 4.0 | 2.5 | 2.5 | 2.0 | 3.0 | — | — |
| ACHN | — | — | — | — | — | — | — | — | 14.0 | 13.0 |

Anti HIV Activity

Human CD4+T cell line PM-1 used in the assay was cultured in RPMI-1640 medium containing 10% Fetal bovine serum, 2 g/L sodium bicarbonate, 100,000 units/L Penicillin-G and 100 mg/L streptomycin. Healthy PM-1 cells were plated on the first day in a 96 well plate at 2×10⁶ cells per well. After 24 h HIV-1/MN was added to the culture and incubated for 2 h for infection. Cells were washed twice with PBS to remove the virus in the culture. Different concentrations of DRF compounds ranging from 10⁻⁴ to 10⁻⁸M were added to the culture and incubated for 96 h. The viability of cells was then assessed by standard MTT assay and the viral antigen P24 levels were estimated by ELSA method. Based on the MTT assay values the P 24 antigen values were corrected. All the samples were tested in triplicates and the average was used for calculations. AZT was used as standard compound for comparision.

| Example | Concentration | Percentage Inhibition |
|---|---|---|
| 1 | 1 μM | 73.94 |
| AZT | 1 μM | 72.47 |

Lymphocyte Proliferation

Human lymphocytes were isolated from whole blood by using Ficoll Hypaque Plus (Amersham). On day one, 1 million lymphocytes were seeded into each well of 96 well plate in 100 μL volume of RPMI 1640 medium containing 10% FCS and Phytohemagglutitin A at 1 μg/well concentration. Plates were incubated at 37° C. in $CO_2$ incubator for 24 h. Test compounds at various concentrations were added to test wells and only medium with vehicle was added to control wells. After 48 h of incubation 0.5 mCi of tritiated thymidine was added to each well. After 24 h of thymidine addition the cells were harvested and the incorporated radioactivity was determined. Stimulation Index (SI) was calculated using the formula, $$SI = \frac{A^T - A^C}{A^C} \times 100$$

$A^T$=Average CPM of treated wells,
$A^C$=Average CPM of control wells.

| Example No. | Concentration | Stimulation Index (SI) |
|---|---|---|
| 1 | 1 μM | 123 |
| 58 | 1 μM | 99 |
| 63 | 1 μM | 59 |
| 6 | 1 μM | 92 |
| 18 | 1 μM | 64 |
| 28 | 1 μM | 40 |
| 39 | 1 μM | 47 |
| 21 | 1 μM | 16 |
| 48 | 1 μM | 130 |
| 12 | 1 μM | 40 |

What is claimed is:
1. An andrographolide of the formula (I),

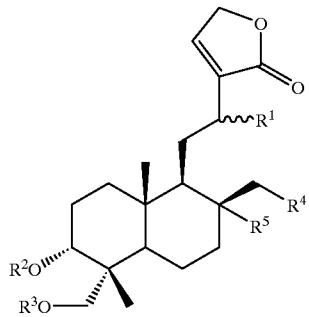

(I)

where R¹ represents halogen, thio, or substituted or unsubstituted alkyl, alkylthio, heteroarylthio, acylthio, aralkylthio, arylthio, alkylseleno, acylseleno, aralkylseleno, arylseleno, $NR^aR^b$ where $R^a$, and $R^b$ are the same or different and independently represent hydrogen, or substituted or unsubstituted alkyl, aryl, acyl, aralkyl, heteroaryl, haloalkyl, or haloacyl or $R^a$ and $R^b$ together with the nitrogen atom to which they are attached form a substituted or unsubstituted 5 or 6 membered cyclic ring system containing carbon atoms, at least one nitrogen atom and optionally one or more hetero atoms selected from oxygen, sulfur or nitrogen, the cyclic ring system may contain one or two double bonds or it may be aromatic or $R^1$ represents $OR^6$ where $R^6$ represents hydrogen or substituted or unsubstituted groups selected from alkyl, aryl, aralkyl, alkenoyl, alkanoyl, aroyl, heteroaroyl, aralkenoyl, aralkanoyl, sulfonyl groups or a group —(CO)—NH—$R^7$ where $R^7$ represents substituted or unsubstituted groups selected from alkyl, aryl, or aralkyl; $R^2$ and $R^3$ the same or different and independently represent hydrogen or substituted or unsubstituted groups selected from alkyl, aryl, heteroaryl, aralkyl, heteroaralkyl, alkanoyl, alkenoyl, aroyl, heteroaroyl, aralkenoyl, aralkanoyl, sulfonyl group or a group —(CO)—W—$R^8$ where W represents O, S or $NR^9$, wherein $R^9$ represents hydrogen or $(C_1–C_6)$ alkyl group, $R^8$ represents substituted or unsubstituted groups selected from alkyl, aryl, aralkyl or aroyl or $OR^2$ and $OR^3$ together form a substituted or unsubstituted 6 or 7 membered cyclic structure containing carbon and oxygen atoms; $R^4$ and $R^5$ together represents =$CH_2$ or an epoxide group; and its stereoisomers, its polymorphs, its salts and its solvates.

2. The compound according to claim 1, wherein the substituents on $R^1$, $R^a$, $R^b$, $R^2$, $R^3$ and $R^6$ are selected from cyano, hydroxy, nitro, thio, halogen or substituted or unsubstituted group selected from $(C_1–C_8)$alkyl, amino, mono or disubstituted amino group, alkanoyl, thio$(C_1–C_8)$alkyl, $(C_1–C_6)$alkoxy, aroyl, acyloxy, aryl, heteroaryl, acylamino, aralkylamino, alkoxycarbonylamino, aryloxycarbonylamino, aralkoxycarbonylamino, $(C_1–C_8)$ alkylthio, heteroarylthio, acylthio, aralkylthio, arylthio, alkylseleno, $(C_1–C_8)$alkylseleno, acylseleno, aralkylseleno, arylseleno or COOR, where R represents hydrogen or $(C_1–C_6)$ alkyl group.

3. The compound according to claim 2, wherein the substituents on $R^1$, $R^a$, $R^b$, $R^2$, $R^3$ and $R^6$ are selected from halogen, hydroxy, nitro, cyano, amino, $(C_1–C_6)$alkyl, aryl or $(C_1–C_6)$alkoxy groups.

4. The compound according to claim 1, wherein the cyclic ring system formed by $R^a$ and $R^b$ together with the nitrogen atoms are selected from uracil, substituted uracil, imidazole, triazole, tetrazole, morpholine, piperazine, pyrazine, pyrimidinone, cytosine and pyrrolidine.

5. The compound according to claim 1, wherein the substituents on the cyclic ring system formed by $R^a$ and $R^b$ together with nitrogen atoms are selected from hydrogen, hydroxy, halogen, linear or branched $(C_1–C_8)$alkyl group, $(C_2–C_6)$alkenyl, $(C_2–C_6)$alkylenyl, amino, nitro, oxo, thio, or imino groups.

6. The compound according to claim 1, wherein the the substituents on $R^7$ are selected from hydroxy, halogen, nitro, cyano, $(C_1–C_6)$alkyl, aryl, or $(C_1–C_6)$aralkyl.

7. A compound according to claim 1, wherein when the group $R^8$ represents substituted alkyl, aryl, aralkyl or aroyl group, the substituents are selected from halogen atom; amino, cyano, hydroxy, nitro, trifluoroethyl, $(C_1–C_6)$alkyl or $(C_1–C_6)$alkoxy.

8. The compound according to claim 1, wherein when the aryl group is disubstituted, the two substituents on the adjacent carbon atoms form a linking group —X—$CH_2$—Y—, or —X—$CH_2$—$CH_2$—Y—, where X and Y are same or different and independently represent O, N, S or $CH_2$.

9. The compound according to claim 1, wherein when the groups represented by $R^1$, $R^a$, $R^b$, $R^2$, $R^3$, $R^6$, $R^7$ or $R^8$ are multisubstituted, the substituents present on the two adjacent carbons form a linking group —X—$(CR^{10}R^{11})_n$—Y— where $R^{10}$ and $R^{11}$ represent $(C_1–C_8)$alkyl, X and Y are same or different and independently represent C, O, S or NH; and n=1 or 2.

10. A compound selected from:
3,19-Diacetyl-12-(N-benzylamino)-14-deoxy andrographolide;
3,19-Diacetyl-12α-(N-benzylamino)-14-deoxy andrographolide;
3,19-Diacetyl-12β-(N-benzylamino)-14-deoxy andrographolide;
14-Deoxy-12-(O-methylphenylglycino)-3,19-O-(1-phenylethylidene)andrographolide;
14-Deoxy-12α-(O-methylphenylglycino)-3,19-O-(1-phenylethylidene)andrographolide;
14-Deoxy-12β-(O-methylphenylglycino)-3,19-O-(1-phenylethylidene)andrographolide;
3,19-Diacetyl-14-deoxy-12-(N-4-methoxybenzylamino) andrographolide;
3,19-Diacetyl-14-deoxy-12α-(N-4-methoxybenzylamino) andrographolide;
3,19-Diacetyl-14-deoxy-12β-(N-4-methoxybenzylamino) andrographolide;
3,19-Diacetyl-12-(N-2-chorobenzylamino)-14-deoxy andrographolide;
3,19-Diacetyl-12α-(N-2-chlorobenzylamino)-14-deoxy andrographolide;
3,19-Diacetyl-12β-(N-2-chlorobenzylamino)-14-deoxy andrographolide;
3,19-Diacetyl-14-deoxy-12-(O-methylprolino) andrographolide;
3,19-Diacetyl-14-deoxy-12α-(O-methylproino) andrographolide;
3,19-Diacetyl-14-deoxy-12β-(O-methylprolino) andrographolide;
3,19-Diacetyl-14-deoxy-12-(O-methylphenylalanino) andrographolide;
3,19-Diacetyl-14-deoxy-12α-(O-methylphenylalanino) andrographolide;
3,19-Diacetyl-14-deoxy-12β-(O-methylphenylalanino) andrographolide;
3,19-Diacetyl-14-deoxy-12-(O-methyl-3-phonylisoserino) andrographolide;
3,19-Diacetyl-14-deoxy-12α-(O-methyl-3-phenylisoserino) andrographolide;
3,19-Diacetyl-14-deoxy-12β-(O-methyl-3-phenylisoserino) andrographolide;
3,19-Diacetyl-14-deoxy-12-(O-methylmethionino) andrographolide;
3,19-Diacetyl-14-deoxy-12α-(O-methylmethionino) andrographolide;
3,19-Diacetyl-14-deoxy-12β-(O-methylmethionino) andrographolide;
3,19-Diacetyl-14-deoxy-12-(O-methylphenylglycino) andrographolide;
3,19-Diacetyl-14-deoxy-12α-(O-methylphenylglycino) andrographolide;
3,19-Diacetyl-14-deoxy-12β-(O-methylphenylglycino) andrographolide;
3,19-Diacetyl-14-deoxy-12-(O-methylalanino) andrographolide;
3,19-Diacetyl-14-deoxy-12α-(O-methylalanino) andrographolide;
3,19-Diacetyl-14-deoxy-12β-(O-methylalanino) andrographolide;
3,19-Diacetyl-14-deoxy-12-(O-methylglycino) andrographolide;

3,19-Diacetyl-14-deoxy-12α-(O-methylglycino) andrographolide;
3,19-Diacetyl-14-deoxy-12β-(O-methylglycino) andrographolide;
3,19-Diacetyl-14-deoxy-12-(O-methylselenomethionino) andrographolide;
3,19-Diacetyl-14-deoxy-12α-(O-methylselenomethionino) andrographolide;
3,19-Diacetyl-14-deoxy-12β-(O-methylselenomethionino) andrographolide;
3,19-Diacetyl-14-deoxy-12-(N-imidazolyl) andrographolide;
3,19-Diacetyl-14-deoxy-12α-(N-imidazolyl) andrographolide;
3,19-Diacetyl-14-deoxy-12β-(N-imidazolyl) andrographolide;
3,19-Diacetyl-14-deoxy-12-(N-methylpiperazino) andrographolide;
3,19-Diacetyl-14-deoxy-12α-(N-methylpiperazino) andrographolide;
3,19-Diacetyl-14-deoxy-12β-(N-methylpiperazino) andrographolide;
3,19-Diacetyl-14-deoxy-12-morpholino andrographolide;
3,19-Diacetyl-14-deoxy-12α-morpholino andrographolide;
3,19-Diacetyl-14-deoxy-12β-morpholino andrographolide;
3,19-Diacetyl-12-(N-acetylpiperazino)-14-deoxy andrographolide;
3,19-Diacetyl-12α-N-acetylpiperazino)-14-deoxy andrographolide;
3,19-Diacetyl-12β-(N-acetylpiperazino)-14-deoxy andrographolide;
12-(N-Benzylamino)-14-deoxy andrographolide;
12α-(N-Benzylamino)-14-deoxy andrographolide;
12β-(N-Benzylamino)-14-deoxy andrographolide;
14-Deoxy-12-(O-methylphenylglycino)andrographolide;
14-Deoxy-12α-(O-methylphenylglycino)andrographolide;
14-Deoxy-12β-(O-methylphenylglycino)andrographolide;
14-Deoxy-3,19-O-isopropylidene-12-(methylphenylalanino)andrographolide;
14-Deoxy-3,19-O-isopropylidene-12α-(methylphenylalanino)andrographolide;
14-Deoxy-3,19-O-isopropylidene-12β-(methylphenylalanino)andrographolide;
12-(N-Benzylamino)-14-deoxy-3,19-O-(1-phenylethylidene)andrographolide;
12α-(N-Benzylamino)-14-deoxy-3,19-O-(1-phenylethylidene)andrographolide;
12β-(N-Benzylamino)-14-deoxy-3,19-O-(1-phenylethylidene)andrographolide;
14-Deoxy-12-(O-methylphenylalanino)-3,19-O-(1-phenylethylidene)andrographolide;
14-Deoxy-12α-(O-methylphenylalanino)-3,19-O-(1-phenylethylidene)andrographolide;
14-Deoxy-12β-(O-methylphenylalanino)-3,19-O-(1-phenylethylidene)andrographolide;
14-Deoxy-12-(O-methylprolino)-3,19-O-(1-phenylethylidene)andrographolide;
14-Deoxy-12α-(O-methylprolino)-3,19-O-(1-phenylethylidene)andrographolide;
14-Deoxy-12β-(O-methylprolino)-3,19-O-(1-phenylethylidene)andrographolide;
3,19-O-Benzylidene-12-(N-benzylamino)-14-deoxy andrographolide;
3,19-O-Benzylidene-12α-benzylamino)-14-deoxy andrographolide;
3,19-O-Benzylidene-12β-(N-benzylamino)-14-deoxy andrographolide;
3,19-Diacetyl-14-deoxy-8,17-epoxy-12-(O-methylmethionino)andrographolide;
3,19-Diacetyl-14-deoxy-8,17-epoxy-12α-(O-methylmethionino)andrographolide;
3,19-Diacetyl-14-deoxy-8,17-epoxy-12β-(O-methylmethionino)andrographolide;
3,19-Diacetyl-14-deoxy-8,17-epoxy-12-(O-methylphenylglycino)andrographolide;
3,19-Diacetyl-14-deoxy-8,17-epoxy-12α-(O-methylphenylglycino)andrographolide;
3,19-Diacetyl-14-deoxy-8,17-epoxy-12β-(O-methylphenylglycino)andrographolide;
3,19-Diacetyl-14-deoxy-12-(N-1,2,4-triazolyl) andrographolide;
3,19-Diacetyl-14-deoxy-12α-(N-1,2,4-triazolyl) andrographolide;
3,19-Diacetyl-14-deoxy-12β-(N-1,2,4-triazolyl) andrographolide;
14-Deoxy-12-(2,3-dimethylanilino)andrographolide;
14-Deoxy-12α-(2,3-dimethylanilino)andrographolide;
14-Deoxy-12β-(2,3-dimethylanilino)andrographolide;
3,19-diacetyl-14-deoxy-12-(4-methoxy-2-methylanilino) andrographolide;
3,19-Diacetyl-14-deoxy-12α-(4-methoxy-2-methylanilino) andrographolide;
3,19-Diacetyl-14-deoxy-12β-(4-methoxy-2-methylanilino) andrographolide;
3,19-Diacetyl-14-deoxy-12-(4-hydroxy-2-methylanilino) andrographolide;
3,19-Diacetyl-14-deoxy-12α-(4-hydroxy-2-methylanilino) andrographolide;
3,19-Diacetyl-14-deoxy-12β-(4-hydroxy-2-methylanilino) andrographolide;
3,19-Diacetyl-14-deoxy-12-(2-mercaptoanilino) andrographolide;
3,19-Diacetyl-14-deoxy-12α-(2-mercaptoanilino) andrographolide;
3,19-Diacetyl-14-deoxy-12β-(2-mercaptoanilino) andrographolide;
3,19-Diacetyl-14-deoxy-12-(3,4-dimethoxyanilino) andrographolide;
3,19-Diacetyl-14-deoxy-12α-(3,4-dimethoxyanilino) andrographolide;
3,19-Diacetyl-14-deoxy-12β-(3,4-dimethoxyanilino) andrographolide;
3,19-Diacetyl-12-anilino-14-deoxy andrographolide;
3,19-Diacetyl-12α-anilino-14-deoxy andrographolide;
3,19-Diacetyl-12β-anilino-14-deoxy andrographolide;
3,19-Diacetyl-14-deoxy-12-(2,3-dimethylanilino) andrographolide;
3,19-Diacetyl-14-deoxy-12α-(2,3-dimethylanilino) andrographolide;
3,19-Diacetyl-14-deoxy-12β-(2,3-dimethylanilino) andrographolide;
3,19-Diacetyl-14-deoxy-12-(2-methyl-4-methylsulfonateanilino)andrographolide;
3,19-Diacetyl-14-deoxy-12α-(2-methyl-4-methylsulfonateanilino)andrographolide;
3,19-Diacetyl-14-deoxy-12β-(2-methyl-4-methylsulfonateanilino)andrographolide;
3,19-Diacetyl-14-deoxy-12-(N-tetrazolylamino) andrographolide;
3,19-Diacetyl-14-deoxy-12α-(N-tetrazolyamino) andrographolide;
3,19-Diacetyl-14-deoxy-12β-(N-tetrazolylamino) andrographolide;
14-Deoxy-12-(3,4-dimethoxyanilino)andrographolide;

14-Deoxy-12α-(3,4-dimethoxyanilino)andrographolide;
14-Deoxy-12β-(3,4-dimethoxyanilino)andrographolide;
14-Deoxy-3,19-O-isopropylidene-12-(2,3-dimethylanilino) andrographolide;
14-Deoxy-3,19-O-isopropylidene-12α-(2,3-dimethylanilino)andrographolide;
14-Deoxy-3,19-O-isopropylidene-12β-(2,3-dimethylanilino)andrographolide;
14-Deoxy-12-(2-methylanilino)-3,19-O-(1-phenylethylidene)andrographolide;
14-Deoxy-12α-(2-methylanilino)-3,19-O-(1-phenylethylidene)andrographolide;
14-Deoxy-12β-(2-methylanilino)-3,19-O-(1-phenylethylidene)andrographolide;
3,19-O-Benzylidene-14-deoxy-12-(2,3-dimethylanilino) andrographolide;
3,19-O-Benzylidene-14-deoxy-12α-(2,3-dimethylanilino) andrographolide;
3,19-O-Benzylidene-14-deoxy-12β-(2,3-dimethylanilino) andrographolide;
3,19-Diacetyl-12-anilino-14-deoxy-8,17-epoxy andrographolide;
3,19-Diacetyl-12α-anilino-14-deoxy-8,17-epoxy andrographolide;
3,19-Diacetyl-12β-anilino-14-deoxy-8,17-epoxy andrographolide;
3,19-Diacetyl-14-deoxy-8,17-epoxy-12-(2,3-dimethylanilino)andrographolide;
3,19-Diacetyl-14-deoxy-8,17-epoxy-12α-(2,3-dimethylanilino)andrographolide;
3,19-Diacetyl-14-deoxy-8,17-epoxy-12β-(2,3-dimethylanilino)andrographolide;
14-Deoxy-12-($N^1$-uracil)andrographolide;
14-Deoxy-12α-($N^1$-uracil)andrographolide;
14-Deoxy-12β-($N^1$-uracil)andrographolide;
3,19-Diacetyl-14-deoxy-12-[N-(1,2-dihydro-2-pyrimidinone)amino]-1-andrographolide;
3,19-Diacetyl-14-deoxy-12α-[N-(1,2-dihydro-2-pyrimidinone)amino]-1-andrographolide;
3,19-Diacetyl-14-deoxy-12β-[N-(1,2-dihydro-2-pyrimidinone)amino]-1-andrographolide;
3,19-Diacetyl-14-deoxy-12-($N^1$-uracil)andrographolide;
3,19-Diacetyl-14-deoxy-12α-($N^1$-uracil)andrographolide;
3,19-Diacetyl-14-deoxy-12β-($N^1$-uracil)andrographolide;
3,19-Diacetyl-14-deoxy-12[$N^1$-(5-chlorouracil)] andrographolide;
3,19-Diacetyl-14-deoxy-12α-[$N^1$-(5-chorouracil)] andrographolide;
3,19-Diacetyl-14-deoxy-12β-[$N^1$-(5-chlorouracil)] andrographolide;
3,19-Diacetyl-14-deoxy-12-[$N^1$-(5-bromouracil)] andrographolide;
3,19-Diacetyl-14-deoxy-12α-[$N^1$-(5-bromouracil)] andrographolide;
3,19-Diacetyl-14-deoxy-12β-[$N^1$-(5-bromouracil)] andrographolide;
3,19-Diacetyl-14-deoxy-12-[$N^1$-(5-fluorouracil] andrographolide;
3,19-Diacetyl-14-deoxy-12α-[$N^1$-(5-fluorouracil] andrographolide;
3,19-Diacetyl-14-deoxy-12β-[$N^1$-(5-fluorouracil)] andrographolide;
3,19-Diacetyl-14-deoxy-12-[$N^1$-(5-iodouracil)] andrographolide;
3,19-Diacetyl-14-deoxy-12α-[$N^1$-(5-iodouracil)] andrographolide;
3,19-Diacetyl-14-deoxy-12β-[$N^1$-(5-iodouracil)] andrographolide;
14-Deoxy-12-[N-(1,2-dihydro-2-pyrimidinone)amino] andrographolide;
14-Deoxy-12α-[N-(1,2-dihydro-2-pyrimidinone)amino] andrographolide;
14-Deoxy-12β-[N-(1,2-dihydro-2-pyrimidinone)amino] andrographolide;
14-Deoxy-12-[$N^1$-(5-fluorouracil)]andrographolide;
14-Deoxy-12α-[$N^1$-(5-fluorouracil)]andrographolide;
14-Deoxy-12β-[$N^1$-(5-fluorouracil)]andrographolide;
14-Deoxy-12-[$N^1$-(5-bromouracil)]andrographolide;
14-Deoxy-12α-[$N^1$-(5-bromouracil)]andrographolide;
14-Deoxy-12β-[$N^1$-(5-bromouracil)]andrographolide;
14-Deoxy-12-[$N^1$-(5-iodouracil)]andrographolide;
14-Deoxy-12α-[$N^1$-(5-iodouracil)]andrographolide;
14-Deoxy-12β-[$N^1$-(5-iodouracil)]andrographolide;
14-Deoxy-8,17-epoxy-12-phenylthio andrographolide;
14-Deoxy-8,17-epoxy-12α-phenylthio andrographolide;
14-Deoxy-8,17-epoxy-12β-phenylthio andrographolide;
3,19-Diacetyl-14-deoxy-12-phenylseleno andrographolide;
3,19-Diacetyl-14-deoxy-12α-phenylseleno andrographolide;
3,19-Diacetyl-14-deoxy-12β-phenylseleno andrographolide;
12-(C-Benzoylmethyl)-14-deoxy-13,19-O-(1-phenylethylidene)andrographolide;
12α-(C-Benzoylmethyl)-14-deoxy-13,19-O-(1-phenylethylidene)andrographolide;
12β-(C-Benzoylmethyl)-14-deoxy-13,19-O-(1-phenylethylidene)andrographolide;
14-Deoxy-3,19-O-isopropylidene-12-ethylthio andrographolide;
14-Deoxy-3,19-O-isopropylidene-12α-ethylthio andrographolide;
14-Deoxy-3,19-O-isopropylidene-12β-ethylthio andrographolide;
3,19-Diacetyl-14-deoxy-12-phenylthio andrographolide;
3,19-Diacetyl-14-deoxy-12α-phenylthio andrographolide;
3,19-Diacetyl-14-deoxy-12β-phenylthio andrographolide;
3,19-Diacetyl-14-deoxy-12-acetylthio andrographolide;
3,19-Diacetyl-14-deoxy-12α-acetylthio andrographolide;
3,19-Diacetyl-14-deoxy-12β-acetylthio andrographolide;
3,19-Diacetyl-14-deoxy-12-ethylthio andrographolide;
3,19-Diacetyl-14-deoxy-12α-ethylthio andrographolide;
3,19-Diacetyl-14-deoxy-12β-ethylthio andrographolide;
3,19-Diacetyl-12-benzyl-14-deoxy andrographolide;
3,19-Diacetyl-12α-benzyl-14-deoxy andrographolide;
3,19-Diacetyl-12β-benzyl-14-deoxy andrographolide;
3,19-Diacetyl-14-deoxy-12-1,1'-diethyl dicarboxylate methyl)andrographolide;
3,19-Diacetyl-14-deoxy-12α-1,1'-diethyl dicarboxylate methyl)andrographolide;
3,19-Diacetyl-14-deoxy-12β-1,1'-diethyl dicarboxylate methyl)andrographolide;
14-Deoxy-12-phenylthio andrographolide;
14-Deoxy-12α-phenylthio andrographolide;
14-Deoxy-12β-phenylthio andrographolide;
14-Deoxy-12-ethylthio andrographolide;
14-Deoxy-12α-ethylthio andrographolide;
14-Deoxy-12β-ethylthio andrographolide;
14-Deoxy-12-phenylseleno andrographolide;
14-Deoxy-12α-phenylseleno andrographolide;
14-Deoxy-12β-phenylseleno andrographolide;
14-Deoxy-3,19-O-isopropylidene-12-phenylthio andrographolide;
14-Deoxy-3,19-O-isopropylidene-12α-phenylthio andrographolide;
14-Deoxy-3,19-O-isopropylidene-12β-phenylthio andrographolide;

14-Deoxy-3,19-O-(1-phenylethylidene)-12-phenylthio andrographolide;
14-Deoxy-3,19-O-(1-phenylethylidene)-12α-phenylthio andrographolide;
14-Deoxy-3,19-O-(1-phenylethylidene)-12β-phenylthio andrographolide;
14-Deoxy-3,19-O-(1-phenylethylidene)-12-ethylthio andrographolide;
14-Deoxy-3,19-O-(1-phenylethylidene)-12α-ethylthio andrographolide;
14-Deoxy-3,19-O-(1-phenylethylidene)-12β-ethylthio andrographolide;
3,19-O-Benzylidene-14-deoxy-12-phenylthio andrographolide;
3,19-O-Benzylidene-14-deoxy-12α-phenylthio andrographolide;
3,19-O-Benzylidene-14-deoxy-12β-phenylthio andrographolide;
3,19-Diacetyl-14-deoxy-8,17-epoxy-12-phenylthio andrographolide;
3,19-Diacetyl-14-deoxy-8,17-epoxy-12α-phenylthio andrographolide;
3,19-Diacetyl-14-deoxy-8,17-epoxy-12β-phenylthio andrographolide;
12-Cinnamoyloxy-14-deoxy andrographolide;
12α-Cinnamoyloxy-14-deoxy andrographolide;
12β-Cinnamoyloxy-14-deoxy andrographolide;
12-Cinnamoyloxy-14-deoxy-8,17-epoxy andrographolide;
12α-Cinnamoyloxy-14-deoxy-8,17-epoxy andrographolide;
12β-Cinnamoyloxy-14-deoxy-8,17-epoxy andrographolide;
14-Deoxy-12-hydroxy andrographolide;
14-Deoxy-12α-hydroxy andrographolide;
14-Deoxy-12β-hydroxy andrographolide;
12-Acetoxy-3,19-diacetyl-14-deoxy andrographolide;
12α-Acetoxy-3,19-diacetyl-14-deoxy andrographolide;
12β-Acetoxy-3,19-diacetyl-14-deoxy andrographolide;
3,19-Diacetyl-14-deoxy-12-methoxy andrographolide;
3,19-Diacetyl-14-deoxy-12α-methoxy andrographolide;
3,19-Diacetyl-14-deoxy-12β-methoxy andrographolide;
3,19-Diacetyl-14-deoxy-12-(2-acetoxy-3-N-acetylamino-3-phenylpropionyloxy)andrographolide;
3,19-Diacetyl-14-deoxy-12α-(2-acetoxy-3-N-acetylamino-3-phenylpropionyloxy)andrographolide;
3,19-Diacetyl-14-deoxy-12β-(2-acetoxy-3-N-acetylamino-3-phenylpropionyloxy)andrographolide;
12-(N-Boc glycinyloxy)-14-deoxy-8,17-epoxy-3,19-dipropionyl andrographolide;
12α-(N-Boc glycinyloxy)-14-deoxy-8,17-epoxy-3,19-dipropionyl andrographolide;
12β-(N-Boc glycinyloxy)-14-deoxy-8,17-epoxy-3,19-dipropionyl andrographolide;
3,19-Diacetyl-14-deoxy-12-mercaptobenzothiazolyl andrographolide;
3,19-Diacetyl-14-deoxy-12α-mercaptobenzothiazolyl andrographolide;
3,19-Diacetyl-14-deoxy-12β-mercaptobenzothiazolyl andrographolide;
3,19-Diacetyl-12-(N,N-benzylchloroacetyl)amino-14-deoxy-12-andrographolide;
3,19-Diacetyl-12α-(N,N-benzylchloroacetyl)amino-14-deoxy-12-andrographolide; and
3,19-Diacetyl-12β-(N,N-benzylchloroacetyl)amino-14-deoxy-12-andrographolide.

11. A process for the preparation of a compound of formula (I)

(I)

where $R^1$ represents halogen, or thio, substituted or unsubstituted alkyl, alkylthio, heteroarylthio, acylthio, aralkylthio, arylthio, alkylseleno, acylseleno, aralkylseleno, arylseleno, $NR^aR^b$ where $R^a$, and $R^b$ are the same or different and independently represent hydrogen, substituted or unsubstituted alkyl, aryl, acyl, aralkyl, heteroaryl, haloalkyl, or haloacyl or $R^a$ and $R^b$ together with the nitrogen atom to which they are attached form a substituted or unsubstituted 5 or 6 membered cyclic ring system containing carbon atoms, at least one nitrogen atom and optionally one or more hetero atoms selected from oxygen, sulfur or nitrogen, the cyclic ring system may contain one or two double bonds or it may be aromatic or $R^1$ represents $OR^6$ where $R^6$ represents hydrogen or substituted or unsubstituted groups selected from alkyl, aryl, aralkyl, alkenoyl, alkanoyl, aroyl, heteroaroyl, aralkenoyl, aralkanoyl, sulfonyl groups or a group —(CO)—NH—$R^7$ where $R^7$ represents substituted or unsubstituted groups selected from alkyl, aryl, or aralkyl; $R^2$ and $R^3$ are same or different and independently represent hydrogen or substituted or unsubstituted groups selected from alkyl, aryl, heteroaryl, aralkyl, heteroaralkyl, alkanoyl, alkenoyl, aroyl, heteroaroyl, aralkenoyl, aralkanoyl, sulfonyl group or a group —(CO)—W—$R^8$ where W represents O, S or $NR^9$, wherein $R^9$ represents hydrogen or ($C_1$–$C_6$) alkyl group, $R^8$ represents substituted or unsubstituted groups selected from alkyl, aryl, aralkyl or aroyl or $OR^2$ and $OR^3$ together form a substituted or unsubstituted 6 or 7 membered cyclic structure containing carbon and oxygen atoms; $R^4$ and $R^5$ represents =$CH_2$ or an epoxide group, or its stereoisomers, its polymorphs, its salts or its solvates, which comprises the steps of:

(i) protecting andrographolide derivative of the formula (VII), (VII)

where $R^4$ and $R^5$ are as defined above, to produce a compound of formula (VIII),

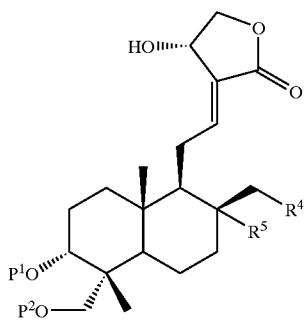

(VIII)

where $P^1$ and $P^2$ are the same or different and represent hydrogen, trityl, t-butyl dimethyl silyl, or pivaloyl; or esters; or $P^1$ and $P^2$ together form methylene dioxy, isopropylidene, benzylidene, or 1-phenyl ethylidene; and $R^4$ and $R^5$ are as defined above, (ii) converting the compound of formula (VIII) to a compound of formula (IX),

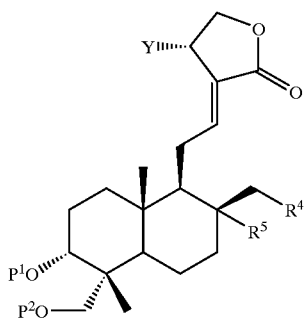

(IX)

where Y represents a halogen atom, esters or sulfonyl esters; $P^1$ and $P^2$ are the same or different and represent hydrogen, trityl, t-butyl dimethyl silyl, or pivaloyl; or esters; or $P^1$ and $P^2$ together form methylene dioxy, isopropylidene, benzylidene, or 1-phenyl ethylidene and the like; and $R^4$ and $R^5$ are as defined above, (iii) reacting andrographolide derivative of the formula (IX) with nucleophile to produce a compound of formula (X)

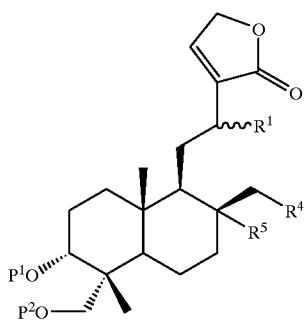

(X)

where all symbols are as defined above and if desired, (iv) deprotecting the compound of formula (X) to produce a compound of formula (XI),

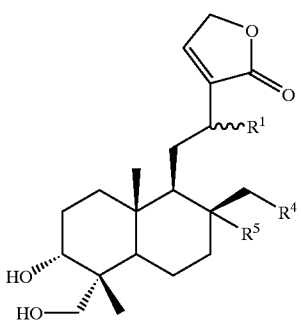

(XI)

where all symbols are as defined above and (v) reacting the compound of formula (XI) with $R^2$-L and/or $R^3$-L, where L represents a leaving group selected from hydroxy, halogen atom; p-toluenesulfonate, methanesulfonate, trifluoromethanesulfonate, or alkanoate groups; $R^2$ and $R^3$ are as defined above to produce a compound of formula (I), and if desired, (vi) converting compound of formula (I) into its stereoisomers, or its pharmaceutical salts.

12. A compound of formula (X),

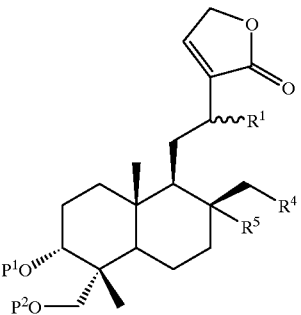

(X)

where $R^1$ represents halogen, thio, or substituted or unsubstituted alkyl, alkylthio, heteroarylthio, acylthio, aralkylthio, arylthio, alkylseleno, acylseleno, aralkylseleno, arylseleno, $NR^a R^b$ where $R^a$, and $R^b$ may be same or different and independently represent hydrogen, substituted or unsubstituted alkyl, aryl, acyl, aralkyl, heteroaryl, haloalkyl, haloacyl or $R^a$ and $R^b$ together with the nitrogen atom to which they are attached form a substituted or unsubstituted 5 or 6 membered cyclic ring system containing carbon atoms, at least one nitrogen atom and optionally one or more hetero atoms selected from oxygen, sulfur or nitrogen, the cyclic ring system may contain one or two double bonds or it may be aromatic or $R^1$ represents $OR^6$ where $R^6$ represents hydrogen or substituted or unsubstituted groups selected from alkyl, aryl, or aralkyl, alkenoyl, alkanoyl, aroyl, heteroaroyl, aralkenoyl, aralkanoyl, sulfonyl groups or a group —(CO)—NH—$R^7$ where $R^7$ substituted or unsubstituted groups selected from alkyl, aryl, or aralkyl; $P^1$ and $P^2$ are the same or different and represent hydrogen, trityl, t-butyl dimethyl silyl, or pivaloyl; or esters; or $P^1$ and $P^2$ together form methylene dioxy, isopropylidene, benzylidene, or 1-phenyl ethylidene; and $R^4$ and $R^5$ together represents double bond or an epoxide group, its stereoisomers, its polymorphs, its salts and its solvates.

13. A process for the preparation of a compound of formula (X)

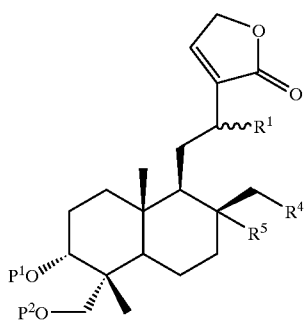

where all the symbols are as defined in claim 12, its stereoisomers, its polymorphs, its salts or its solvates, which comprises the steps of:

(i) protecting andrographolide derivative of the formula (VII),

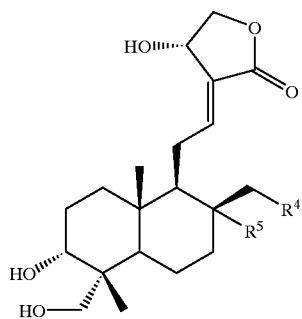

where $R^4$ and $R^5$ are as defined above, to produce a compound of formula (VIII),

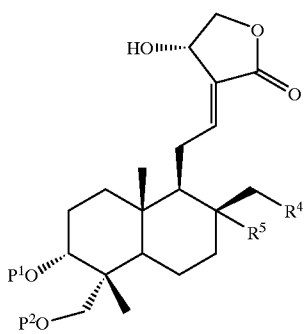

where $P^1$ and $P^2$ are the same or different and represent hydrogen, trityl, t-butyl dimethyl silyl, or pivaloyl; or esters; or $P^1$ and $P^2$ together form methylene dioxy, isopropylidene, benzylidene, or 1-phenyl ethylidene and $R^4$ and $R^5$ are as defined above, (ii) converting the compound of formula (VIII) to a compound of formula (IX),

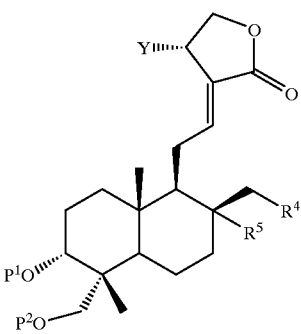

where Y represents a halogen atom; esters or sulfonyl esters; $P^1$ and $P^2$ are the same or different and represent hydrogen, trityl, t-butyl dimethyl silyl, or pivaloyl; or esters; or $P^1$ and $P^2$ together form methylene dioxy, isopropylidene, benzylidene, or 1-phenyl ethylidene; and $R^4$ and $R^5$ are as defined above, and (iii) reacting the compound of formula (IX) with a nucleophile to form a compound of formula (X).

14. A compound of formula (XI),

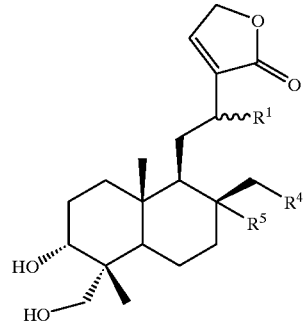

where $R^1$ represents halogen, thio, or substituted or unsubstituted alkyl, alkylthio, heteroarylthio, acylthio, aralkylthio, arylthio, alkylseleno, acylseleno, aralkylseleno, arylseleno, $NR^aR^b$ where $R^a$, and $R^b$ are the same or different and independently represent hydrogen, substituted or unsubstituted alkyl, aryl, acyl, aralkyl, heteroaryl, haloalkyl, haloacyl or $R^a$ and $R^b$ together with the nitrogen atom to which they are attached form a substituted or unsubstituted 5 or 6 membered cyclic ring system containing carbon atoms, at least one nitrogen atom and optionally one or more hetero atoms selected from oxygen, sulfur or nitrogen, the cyclic ring system may contain one or two double bonds or it may be aromatic or $R^1$ represents $OR^6$ where $R^6$ represents hydrogen or substituted or unsubstituted groups selected from alkyl, aryl, aralkyl, alkenoyl, alkanoyl, aroyl, heteroaroyl, aralkenoyl, aralkanoyl, sulfonyl groups or a group —(CO)—NH—$R^7$ where $R^7$ represents substituted or unsubstituted groups selected from alkyl, aryl, aralkyl; $R^4$ and $R^5$ together represents =$CH_2$ or an epoxide group, its stereoisomers, its polymorphs, its salts and its solvates.

15. A process for the preparation of the compound of formula (XI)

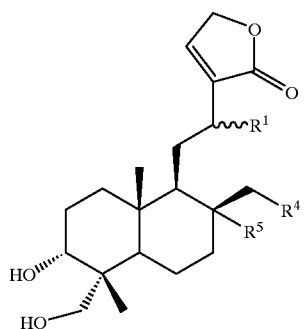

(XI)

where all the symbols are as defined in claim 14, its stereoisomers, its polymorphs, its salts or its pharmaceutically acceptable solvates, which comprises the steps of:

(i) protecting andrographolide derivative of the formula (VII),

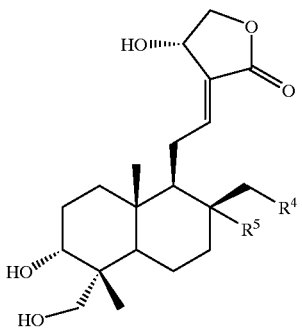

(VII)

where $R^4$ and $R^5$ are as defined above, to produce a compound of formula (VIII),

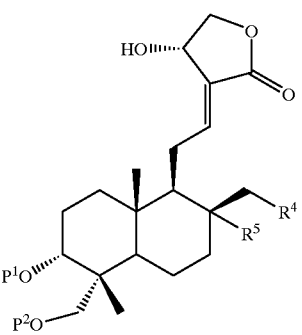

(VIII)

where $P^1$ and $P^2$ are the same or different and represent hydrogen, trityl, t-butyl dimethyl silyl, or pivaloyl; or esters; or $P^1$ and $P^2$ together form methylene dioxy, isopropylidene, benzylidene, or 1-phenyl ethylidene; and $R^4$ and $R^5$ are as defined above, (ii) converting the compound of formula (VIII) to a compound of formula (IX),

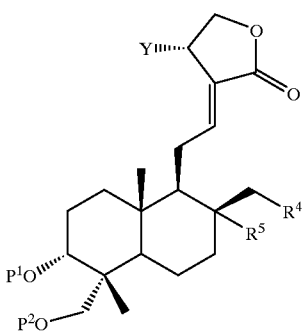

(IX)

where Y represents a halogen atom; esters or sulfonyl esters; $P^1$ and $P^2$ are the same or different and represent hydrogen, trityl, t-butyl dimethyl silyl, or pivaloyl; or esters or $P^1$ and $P^2$ together form methylene dioxy, isopropylidene, benzylidene, or 1-phenyl ethylidene; $R^4$ and $R^5$ are as defined above, (iii) reacting andrographolide of the formula (IX)

(IX)

with a suitable nucleophile to produce a compound of formula (X)

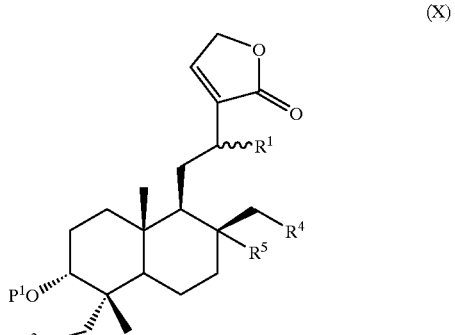

(X)

where all symbols are as defined above and if desired, (iv) deprotecting the compound of formula (X) to produce a compound of formula (XI).

16. A composition, which comprises a compound of formula (I), or a stereoisomer, salt, polymorph or solvate thereof

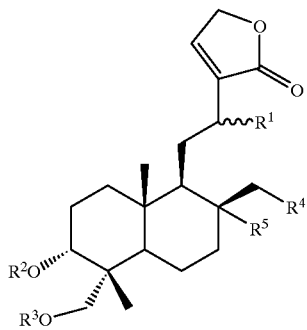

(I)

as defined in claim 1, and a pharmaceutically acceptable carrier, diluent, excipient or solvate.

17. The composition as claimed in claim 16, in the form of a tablet, capsule, powder, syrup, solution or suspension.

18. A method for treating cancer, psoriasis, HSV infections, HIV infections, restenosis, atherosclerosis, viral infections, malaria, bacterial infections, immunomodulation, liver disorders, and cardiovascular disorders, diabetes, and dyslipidemia, which comprises administering an effective amount of a compound of formula (I) as claimed in claim 1, to a patient in need thereof.

19. A method for treating insulin resistance (type II diabetes), leptin resistance, impaired glucose tolerance, dyslipidemia, body weight reduction, and disorders related to syndrome X which comprises administering an effective amount of a compound of formula (I) as claimed in claim 1 to a patient in need thereof.

20. The method according to claim 19, wherein the disorders relating to syndrome X are hypertension, obesity, insulin resistance, coronary heart disease and other cardiovascular disorders.

21. A method for preventing insulin resistance (type II diabetes), leptin resistance, impaired glucose tolerance, dyslipidemia, body weight increase, and disorders related to syndrome X which comprises administering an effective amount of a compound of formula (I) as claimed in claim 1 to a patient in need thereof.

22. The method according to claim 21, wherein the disorders relating to syndrome X are hypertension, obesity, insulin resistance, coronary heart disease and other cardiovascular disorders.

23. A method for preventing psoriasis, restenosis, atherosclerosis, malaria, immunomodulation, liver disorders, cardiovascular disorders, diabetes, and dyslipidemia, which comprises administering an effective amount of a compound of formula (I) as claimed in claim 1 to a patient in need thereof.

24. A pharmaceutical composition which comprises a compound as defined in claim 10, and a pharmaceutically acceptable carrier, diluent, excipient or solvate.

25. A pharmaceutical composition as claimed in claim 24, in the form of a tablet, capsule, powder, syrup, solution or suspension.

26. A method for treating insulin resistance (type II diabetes), leptin resistance, impaired glucose tolerance, dyslipidemia, body weight reduction, and disorders related to syndrome X which comprises administering an effective amount of a compound as claimed in claim 10 to a patient in need thereof.

27. The method according to claim 26, wherein the disorders relating to syndrome X are hypertension, obesity, insulin resistance, coronary heart disease and other cardiovascular disorders.

28. A method for preventing insulin resistance (type II diabetes), leptin resistance, impaired glucose tolerance, dyslipidemia, body weight reduction, and disorders related to syndrome X which comprises administering an effective amount of a compound as claimed in claim 10 to a patient in need thereof.

29. The method according to claim 28, wherein the disorders relating to syndrome X are hypertension, obesity, insulin resistance, coronary heart disease and other cardiovascular disorders.

30. A method for treating cancer, psoriasis, HSV infections, HIV infections, restenosis, atherosclerosis, viral infections, malaria, bacterial infections, immunomodulation, liver disorders, cardiovascular disorders, diabetes, and dyslipidemia, which comprises administering an effective amount of a compound as claimed in claim 10, to a patient in need thereof.

31. A method for preventing psoriasis, restenosis, atherosclerosis, malaria, immunomodulation, liver disorders, cardiovascular disorders, diabetes, and dyslipidemia, and metabolic disorders, which comprises administering an effective amount of a compound as claimed in claim 10, to a patient in need thereof.

32. A compound of formula (IX)

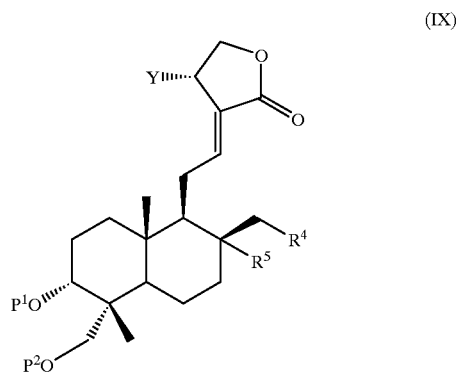

(IX)

where Y represents a halogen atom; $P^1$ and $P^2$ are the same or different and represent hydrogen, trityl, t-butyl dimethyl silyl, or pivaloyl; or esters or $P^1$ and $P^2$ together form methylene dioxy, isopropylidene, benzylidene, or 1-phenyl ethylidene; and $R^4$ and $R^5$ together represent $=CH^2$ or an epoxide group, its stereoisomers, its polymorphs, its salts and its solvates.

33. A process for the preparation of the compound of formula of formula (IX) as defined in claim 32, which comprises:

(i) protecting andrographolide derivative of the formula (VII),

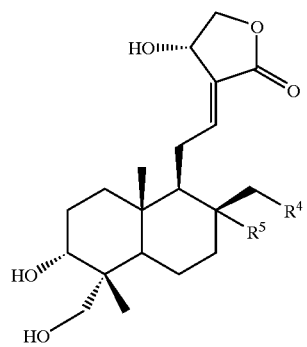

(VII)

where $R^4$ and $R^5$ are as defined in claim 32, to produce a compound of formula (VIII),

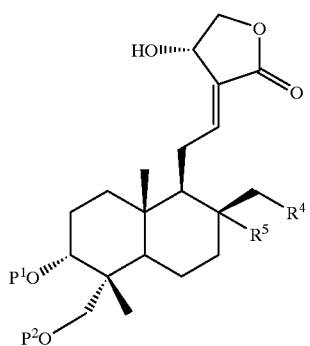

(VIII)

where $P^1$ and $P^2$ are the same or different and represent hydrogen, trityl, t-butyl dimethyl silyl, or pivaloyl; or esters; or $P^1$ and $P^2$ together form methylene dioxy, isopropylidene, benzylidene, or 1-phenyl ethylidene; $R^4$ and $R^5$ together represent $=CH_2$ or an epoxide, (ii) converting the compound of formula (VIII) to a compound of formula (IX),

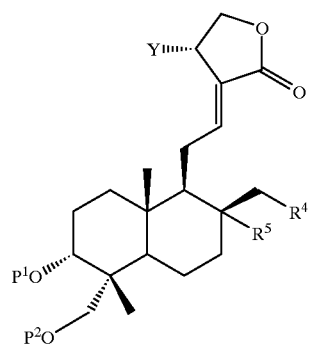

(IX)

where Y represents a halogen atom; esters; or sulfonyl esters; $P^1$ and $P^2$ are the same or different and represent hydrogen, trityl, t-butyl dimethyl silyl, or pivaloyl; or esters; or $P^1$ and $P^2$ together form methylene dioxy, isopropylidene, benzylidene, or 1-phenyl ethylidene and the like; and $R^4$ and $R^5$ are as defined above.

34. The compound according to claim 5, wherein the linear or branched $(C_1-C_8)$alkyl group is selected from methyl, ethyl, n-propyl, or isopropyl.

35. The compound according to claim 1, where the cyclic structure formed by $OR^2$ and $OR^3$ is $-O-(CR^{10}R^{11})_m-O-$ wherein $R^{10}$ and $R^{11}$ are same or different and independently represent hydrogen, or unsubstituted or substituted groups selected from $(C_1-C_6)$alkyl, aryl group, heteroaryl or $R^{10}$ and $R^{11}$ together represent $C=O$; and m represents an integer 1 or 2.

36. A composition, which comprises an effective amount of a compound of formula (X), or a stereoisomer, salt, polymorph or solvate thereof

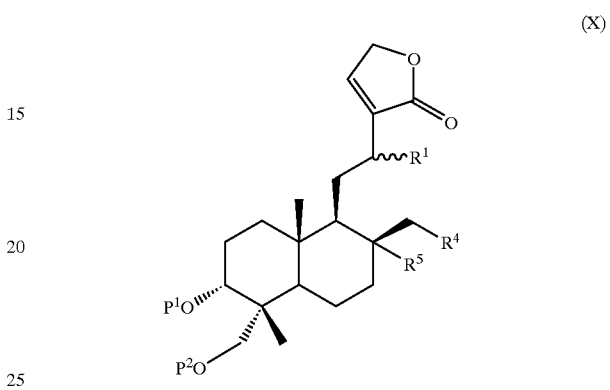

(X)

as defined in claim 12, and a pharmaceutically acceptable carrier, diluent, excipient or solvate.

37. The composition as claimed in claim 36, in the form of a tablet, capsule, powder, syrup, solution or suspension.

38. A method of treating cancer, psoriasis, HSV infections, HIV infections, restenosis, atherosclerosis, viral infections, malaria, bacterial infections, immunomodulation, liver disorders, cardiovascular disorders, diabetes, and dyslipidemia, which comprises administering an effective amount of a compound of formula (X) as claimed in claim 12, to a patient in need thereof.

39. A method for treating insulin resistance (type II diabetes), leptin resistance, impaired glucose tolerance, dyslipidemia, body weight reduction, and disorders related to syndrome X which comprises administering an effective amount of a compound of formula (X) as claimed in claim 12 to a patient in need thereof.

40. The method according to claim 39, wherein the disorders relating to syndrome X are hypertension, obesity, insulin resistance, coronary heart disease and other cardiovascular disorders.

41. A method for preventing insulin resistance (type II diabetes), leptin resistance, impaired glucose tolerance, dyslipidemia, body weight reduction, and disorders related to syndrome X which comprises administering an effective amount of a compound of formula (X) as claimed in claim 12 to a patient in need thereof.

42. The method according to claim 41, wherein the disorders relating to syndrome X are hypertension, obesity, insulin resistance, coronary heart disease and other cardiovascular disorders.

43. A method for preventing psoriasis, restenosis, atherosclerosis, malaria, immunomodulation, liver disorders, cardiovascular disorders, diabetes, and dyslipidemia, which comprises administering an effective amount of a compound of formula (X) as claimed in claim 12 to a patient in need thereof.

44. A pharmaceutical composition which comprises a compound of formula (XI) as defined in claim 14, and a pharmaceutically acceptable carrier, diluent, excipient or solvate.

45. A pharmaceutical composition as claimed in claim 44, in the form of a tablet, capsule, powder, syrup, solution or suspension.

46. A method for treating insulin resistance (type II diabetes), leptin resistance, impaired glucose tolerance, dyslipidemia, body weight reduction, and disorders related to syndrome X which comprises administering an effective amount of a compound of formula (XI) as claimed in claim 14 to a patient in need thereof.

47. The method according to claim 46, wherein the disorders relating to syndrome X are hypertension, obesity, insulin resistance, coronary heart disease and other cardiovascular disorders.

48. A method for preventing insulin resistance (type II diabetes), leptin resistance, impaired glucose tolerance, dyslipidemia, body weight increase, and disorders related to syndrome X which comprises administering an effective amount of a compound of formula (XI) as claimed in claim 14 to a patient in need thereof.

49. The method according to claim 48, wherein the disorders relating to syndrome X are hypertension, obesity, insulin resistance, coronary heart disease and other cardiovascular disorders.

50. A method for treating cancer, psoriasis, HSV infections, HIV infections, restenosis, atherosclerosis, viral infections, malaria, bacterial infections, immunomodulation, liver disorders, and cardiovascular disorders, diabetes, and dyslipidemia, which comprises administering an effective amount of a compound of formula (XI) as claimed in claim 14, to a patient in need thereof.

51. A method for preventing psoriasis, restenosis, atherosclerosis, malaria, immunomodulation, liver disorders, cardiovascular disorders, diabetes, and dyslipidemia, which comprises administering an effective amount of a compound of formula (XI) as claimed in claim 14, to a patient in need thereof.

52. A composition, which comprises an a compound of formula (IX), or a stereoisomer, salt, polymorph or solvate thereof

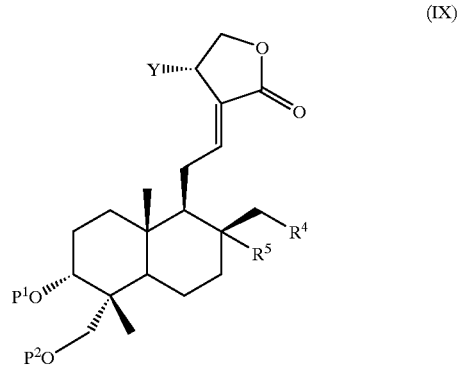

(IX)

as defined in claim 32, and a pharmaceutically acceptable carrier, diluent, excipient or solvate.

53. The composition as claimed in claim 52, in the form of a tablet, capsule, powder, syrup, solution or suspension.

54. A method for treating cancer, psoriasis, HSV infections, HIV infections, restenosis, atherosclerosis, viral infections, malaria, bacterial infections, immunomodulation, liver disorders, cardiovascular disorders, diabetes, dyslipidemia, and metabolic disorders, which comprises administering an effective amount of a compound of formula (IX) as claimed in claim 32, to a patient in need thereof.

55. A method for treating insulin resistance (type II diabetes), leptin resistance, impaired glucose tolerance, dyslipidemia, body weight reduction, and disorders related to syndrome X which comprises administering an effective amount of a compound of formula (IX) as claimed in claim 32 to a patient in need thereof.

56. The method according to claim 55, wherein the disorders relating to syndrome X are hypertension, obesity, insulin resistance, coronary heart disease and other cardiovascular disorders.

57. A method for preventing insulin resistance (type II diabetes), leptin resistance, impaired glucose tolerance, dyslipidemia, body weight increase, and disorders related to syndrome X which comprises administering an effective amount of a compound of formula (IX) as claimed in claim 32 to a patient in need thereof.

58. The method according to claim 57, wherein the disorders relating to syndrome X are hypertension, obesity, insulin resistance, coronary heart disease and other cardiovascular disorders.

59. A method for preventing psoriasis, restenosis, atherosclerosis, malaria, immunomodulation, liver disorders, cardiovascular disorders, diabetes, and dyslipidemia, which comprises administering an effective amount of a compound of formula (IX) as claimed in claim 32 to a patient in need thereof.

* * * * *

UNITED STATES PATENT AND TRADEMARK OFFICE
CERTIFICATE OF CORRECTION

PATENT NO.     : 6,576,662 B2
DATED          : June 10, 2003
INVENTOR(S)    : Srinivas Nanduri et al.

It is certified that error appears in the above-identified patent and that said Letters Patent is hereby corrected as shown below:

<u>Title page,</u>
Item [30], add -- June 8, 2000 (IN) .... 435/MAS/2000 --.

Signed and Sealed this

Twenty-third Day of September, 2003

JAMES E. ROGAN
*Director of the United States Patent and Trademark Office*